(12) United States Patent
Song et al.

(10) Patent No.: US 12,108,659 B2
(45) Date of Patent: Oct. 1, 2024

(54) ORGANIC ELECTROLUMINESCENT DEVICE

(71) Applicants: LG Display Co., Ltd., Seoul (KR); Material Science Co., Ltd., Seoul (KR)

(72) Inventors: Inbum Song, Seoul (KR); Seunghee Yoon, Seoul (KR); Sang-Hoon Hong, Seoul (KR); Hyun Bin Kang, Suwon-si (KR); Jaemin Ryu, Bucheon-si (KR)

(73) Assignees: LG Display Co., Ltd., Seoul (KR); Material Science Co., Ltd., Seoul (KR)

( * ) Notice: Subject to any disclaimer, the term of this patent is extended or adjusted under 35 U.S.C. 154(b) by 293 days.

(21) Appl. No.: 16/515,738

(22) Filed: Jul. 18, 2019

(65) Prior Publication Data

US 2020/0028084 A1 Jan. 23, 2020

(30) Foreign Application Priority Data

Jul. 19, 2018 (KR) .................. 10-2018-0084228
Jul. 16, 2019 (KR) .................. 10-2019-0085997

(51) Int. Cl.
*H01L 51/00* (2006.01)
*C07C 211/61* (2006.01)
(Continued)

(52) U.S. Cl.
CPC .......... *H10K 85/633* (2023.02); *C07C 211/61* (2013.01); *C07D 307/91* (2013.01);
(Continued)

(58) Field of Classification Search
CPC ............ H01L 51/006; H01L 51/0061; H01L 51/008; H01L 51/0058; H01L 51/5012; H01L 51/5016; H01L 51/5278; H01L 51/5056; H01L 51/5072; H01L 51/0055; H01L 51/0054; H01L 51/0073; H01L 27/3244; H01L 51/5024; H01L 51/0032;
(Continued)

(56) References Cited

U.S. PATENT DOCUMENTS 10,686,141 B2 6/2020 Hatakeyama et al.
2003/0049489 A1* 3/2003 Hatwar .................. H10K 50/11
313/506
(Continued)

FOREIGN PATENT DOCUMENTS

CN 102203212 A 9/2011
CN 107793441 A 3/2018
(Continued)

OTHER PUBLICATIONS

Korean Office Action dated Jul. 23, 2020 issued in Patent Application No. 10-2019-0085997 (5 pages).
Chinese Office Action dated Aug. 10, 2021 issued in corresponding Patent Application No. 201910654314.6 w/ English Translation (26 pages).

*Primary Examiner* — Alexander C Kollias
(74) *Attorney, Agent, or Firm* — POLSINELLI PC

(57) ABSTRACT

Disclosed is an organic electroluminescent device. More specifically, disclosed is an organic electroluminescent device comprising at least one organic layer comprising at least two dopant compounds therein. The electroluminescent device employs both of a boron-based dopant and a pyrene-based dopant to provide improved color characteristics, efficiency and lifespan.

7 Claims, 3 Drawing Sheets

(51) Int. Cl.
*C07D 307/91* (2006.01)
*C07F 5/02* (2006.01)
*C09K 11/06* (2006.01)
*H10K 85/30* (2023.01)
*H10K 85/60* (2023.01)
*H10K 50/11* (2023.01)
*H10K 50/15* (2023.01)
*H10K 50/16* (2023.01)
*H10K 50/19* (2023.01)
*H10K 101/10* (2023.01)

(52) U.S. Cl.
CPC ............ *C07F 5/027* (2013.01); *C09K 11/06* (2013.01); *H10K 85/322* (2023.02); *H10K 85/636* (2023.02); *C07C 2603/50* (2017.05); *C07C 2603/52* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 50/15* (2023.02); *H10K 50/16* (2023.02); *H10K 50/19* (2023.02); *H10K 85/622* (2023.02); *H10K 85/623* (2023.02); *H10K 85/626* (2023.02); *H10K 85/6574* (2023.02); *H10K 2101/10* (2023.02)

(58) Field of Classification Search
CPC ............ C09K 11/06; C09K 2211/1007; C09K 2211/1011; C09K 2211/1014; C09K 2211/1018; C07D 307/91; C07F 5/027; C07F 7/081; C07C 211/61; C07C 2603/52; C07C 2603/50; H10K 85/622; H10K 85/322
See application file for complete search history.

(56) References Cited

U.S. PATENT DOCUMENTS

| | | | |
|---|---|---|---|
| 2004/0137270 A1* | 7/2004 | Seo | H05B 33/14 428/690 |
| 2009/0009101 A1* | 1/2009 | Kang | H01L 27/3209 315/250 |
| 2011/0156011 A1* | 6/2011 | Bin | C07C 255/58 257/40 |
| 2011/0248246 A1* | 10/2011 | Ogita | C09K 11/06 257/E51.026 |
| 2012/0056165 A1* | 3/2012 | Kawamura | C09B 57/001 252/301.16 |
| 2015/0034915 A1* | 2/2015 | Kim | H10K 85/636 257/40 |
| 2015/0053933 A1* | 2/2015 | Lee | H10K 85/654 257/40 |
| 2015/0236274 A1* | 8/2015 | Hatakeyama | H01L 51/0052 257/40 |
| 2015/0333266 A1* | 11/2015 | Ito | H01L 51/0059 257/40 |
| 2018/0301629 A1* | 10/2018 | Hatakeyama | H10K 85/657 |
| 2019/0006592 A1* | 1/2019 | Jeong | C07F 7/081 |
| 2019/0058124 A1* | 2/2019 | Hatakeyama | C09K 11/06 |
| 2020/0176679 A1* | 6/2020 | Jeong | H10K 85/322 |
| 2020/0220083 A1 | 7/2020 | Hatakeyama et al. | |

FOREIGN PATENT DOCUMENTS

| | | | |
|---|---|---|---|
| JP | 2015-111592 A | 6/2015 | |
| KR | 10-2015-0132795 A | 11/2015 | |
| KR | 10-2017-0122296 A | 11/2017 | |
| KR | 10-1876763 B1 | 7/2018 | |
| WO | WO-2017116169 A1 * | 7/2017 | ............ C07C 15/20 |
| WO | 2018/095397 A1 | 5/2018 | |

* cited by examiner

ORGANIC ELECTROLUMINESCENT DEVICE

CROSS-REFERENCE TO RELATED APPLICATION

This application claims priority from Korean Patent Application Nos. 10-2018-0084228 filed on Jul. 19, 2018, and 10-2019-0085997, filed on Jul. 16, 2019, in the Korean Intellectual Property Office, the disclosures of which are incorporated herein by reference in their entirety.

BACKGROUND

Field of the Disclosure

The present disclosure relates to an organic electroluminescent device. More specifically, the present disclosure relates to an organic electroluminescent device comprising at least one organic layer comprising at least two dopant compounds therein.

Description of the Background

A need for improved brightness, color purity, and lifespan is steadily being raised in current commercialized OLED products. In addition, a need for high-resolution and eye fatigue reduction to realize virtual reality and augmented reality is increasing.

A blue dopant currently widely used in the field of OLED has an intrinsic maximum wavelength being a short wavelength. However, the blue dopant exhibits a shoulder shape in a long wavelength. Further, the blue dopant has a broad spectrum having FWHM (full width at half maximum) of 30 nm or larger. In a front light-emitting device, light of a wavelength region other than a main wavelength of the blue dopant is optically lost due to a microcavity effect, and does not contribute to efficiency. Furthermore, the blue dopant in a white rendering device of a stack structure may not contribute to efficiency because, in order to realize high color purity, a color filter removes an upper wavelength region.

A boron-based derivative blue dopant which has been actively researched and developed recently has a light-emitting FWHM (full width at half maximum) of 25 nm or smaller. This has an advantage of minimizing the optical loss and thus obtaining a desired color characteristic and increased efficiency.

However, the boron-based derivative dopant has a relatively short lifespan as compared with the conventional dopant. Thus, this may disallow commercializing the dopant. Therefore, efforts should be made to solve the problem by increasing the lifespan while improving the color purity and lifespan.

SUMMARY

One purpose of the present disclosure is to complement shortcomings in terms of color rendering, efficiency, and lifespan of dopant materials used together with a host material in a light-emitting layer of an organic electroluminescent device, and thus to maintain both the efficiency and lifespan characteristics while implementing color characteristics required by a completed device.

The purposes of the present disclosure are not limited to the above-mentioned purposes. Other purposes and advantages of the present disclosure, as not mentioned above, may be understood from the following description and more clearly understood from the embodiments of the present disclosure. Further, it will be readily appreciated that the objects and advantages of the present disclosure may be realized by features and combinations thereof as disclosed herein.

In one implementation of the present disclosure, there is provided an organic electroluminescent device comprising an anode, a cathode, and at least one organic layer between the anode and the cathode, wherein the organic layer comprises a compound represented by Chemical Formula 1 and a compound represented by Chemical Formula 2:

[Chemical Formula 1]

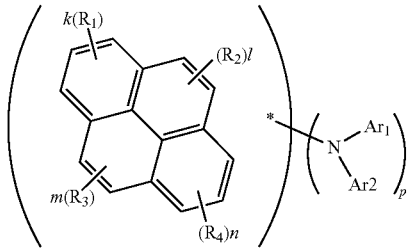

wherein, in Chemical Formula 1, $Ar_1$ and $Ar_2$ are the same or different from each other, and each of $Ar_1$ and $Ar_2$ independently represents one selected from a group consisting of a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 5 to 60 nuclear atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl group having 6 to 30 carbon atoms, and a substituted or unsubstituted aryloxy group having 6 to 30 carbon atoms, wherein each of $Ar_1$ and $Ar_2$ may be bonded to an adjacent group thereto to form a substituted or unsubstituted ring, wherein each of $R_1$ to $R_4$ independently represents a substituent selected from a group consisting of deuterium, a cyano group, a nitro group, a halogen group, a hydroxyl group, a substituted or unsubstituted alkylthio group having 1 to 4 carbon atoms, a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 5 to 60 nuclear atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl groups having 6 to 30 carbon atoms, and a substituted or unsubstituted aryloxy groups having 6 to 30 carbon atoms, wherein each of $R_1$ to $R_4$ may be bonded to an adjacent group thereto to form a substituted or unsubstituted ring, wherein * indicates a site at which bonding occurs,
wherein p is independently an integer of 1 to 4,
wherein each of k, l, m and n is independently an integer of 0 to 2,

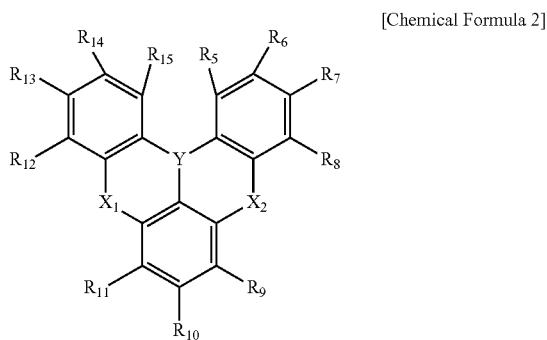

[Chemical Formula 2]

wherein in Chemical Formula 2, Y is B, N, P=O or P=S,
wherein $X_1$ and $X_2$ are the same or different from each other, wherein each of $X_1$ and $X_2$ independently represents one selected from a group consisting of O, S, Se, $CR_{16}R_{17}$ and $NR_{18}$,
wherein $R_5$ to $R_{18}$ are the same or different from each other, wherein each of $R_5$ to $R_{18}$ independently represents one selected from a group consisting of hydrogen, deuterium, a cyano group, a nitro group, a halogen group, a hydroxyl group, a substituted or unsubstituted alkylthio group having 1 to 4 carbon atoms, a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 5 to 60 nuclear atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl groups having 6 to 30 carbon atoms, and a substituted or unsubstituted aryloxy group having 6 to 30 carbon atoms, wherein each of $R_5$ to $R_{18}$ may be bonded to an adjacent group thereto to form a substituted or unsubstituted ring, wherein in Chemical Formula 1 and Chemical Formula 2, each of $R_1$ to $R_{18}$, $Ar_1$ and $Ar_2$ is independently substituted with at least one substituent selected from a group consisting of deuterium, a cyano group, a nitro group, a halogen group, a hydroxyl group, an alkyl group having 1 to 30 carbon atoms, a cycloalkyl group having 3 to 30 carbon atoms, an alkenyl group having 2 to 30 carbon atoms, an alkynyl group having 2 to 24 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having from 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms, and an aryloxy group having 6 to 30 carbon atoms, wherein when the at least one substituent includes a plurality of substituents, the plurality of substituents are the same or different from each other.

In accordance with the present disclosure, the electroluminescent device employs both of the boron-based and pyrene-based dopants to provide improved color characteristics, efficiency and lifespan.

DETAILED DESCRIPTION

Figure 1:
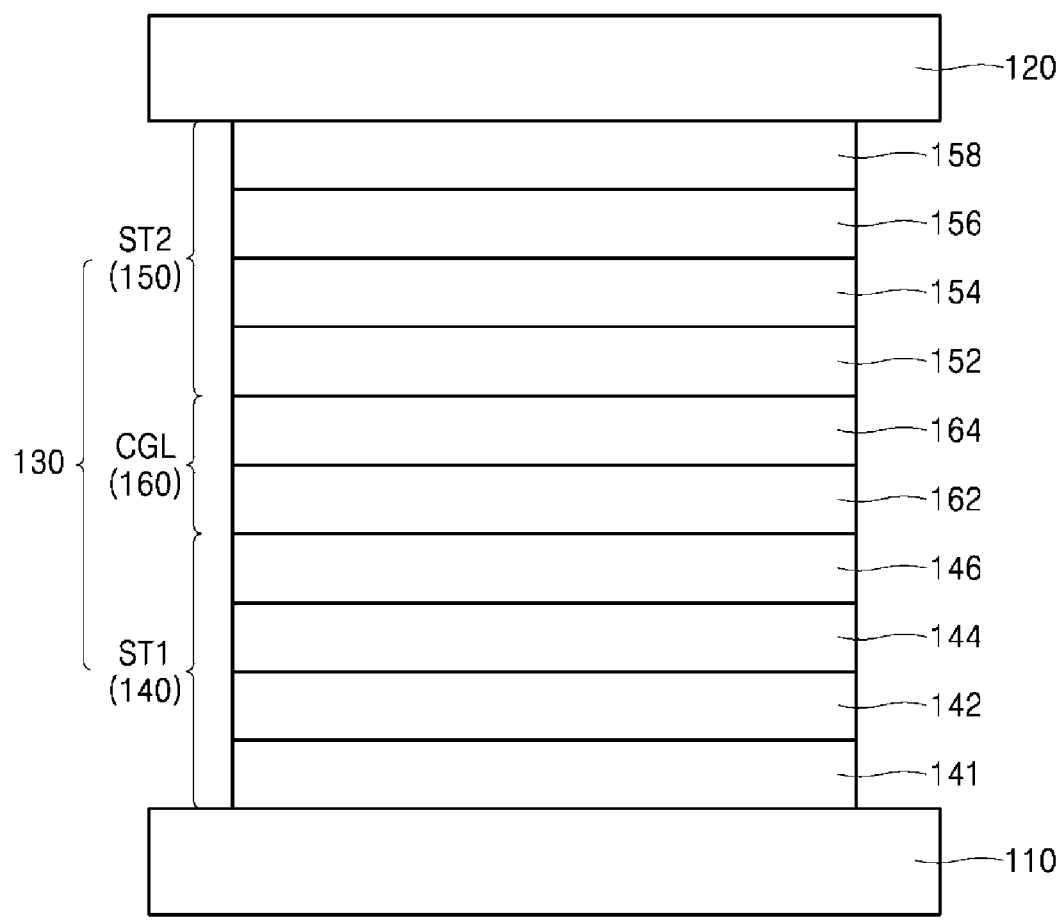
FIG. 1 shows a schematic cross-sectional view of an organic electroluminescent device having a tandem structure having two light emission sub-stacks and comprising a compound represented by Chemical Formula 1 according to one embodiment of the present disclosure.

Embodiments of the present disclosure are provided to more fully describe the present disclosure to those skilled in the art. The following embodiments may be modified in various different forms. The scope of the present disclosure is not limited to the following embodiments. Rather, these embodiments are provided so that the present disclosure will be more thorough and complete and are provided to fully convey ideas of the present disclosure to those skilled in the art.

Generally, a light-emitting layer in an OLED device has a structure in which a small quantity of dopants having a high luminous efficiency are doped into a host in which a charge conduction and an exciton occur.

The excitons occurring in the host are transferred to the dopants using Forster or Dexter transition, such that the dopants emit light.

According to the present disclosure, boron type dopants with excellent color characteristic and efficiency, and conventional pyrene type dopants are used together to realize excellent lifespan and color characteristic and efficiency of a completed device.

The color characteristic is ultimately influenced by energy transfer to a second dopant emitting light from a host and a first dopant. That is, an energy absorption wavelength band of the borne based dopant used as the second dopant is very close to a light-emitting wavelength band. Thus, the energy absorption wavelength band of the borne based dopant considerably overlaps the light-emitting wavelength of the host and an intrinsic light-emitting wavelength band of the first dopant having a maximum emission wavelength similar to that of the second dopant. Thus, the sufficient energy transfer to the second dopant occurs so that the luminescence mainly occurs from the boron-based dopant as the second dopant.

Charge conduction acting as a hole trap in the light-emitting layer and lifespan degradation of the dopants due to repetition of energy transfer may be mitigated when roles of the dopants are divided between the first and second dopants.

In one implementation of the present disclosure, there is provided an organic electroluminescent device comprising an anode, a cathode, and at least one organic layer between the anode and the cathode, wherein the organic layer comprises a compound represented by Chemical Formula 1 and a compound represented by Chemical Formula 2:

[Chemical Formula 1]

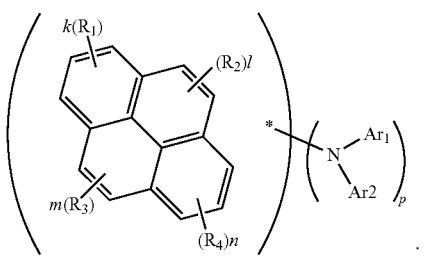

In Chemical Formula 1, $Ar_1$ and $Ar_2$ are the same or different from each other, and each of $Ar_1$ and $Ar_2$ independently represents one selected from a group consisting of a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 5 to 60 nuclear atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl group having 6 to 30 carbon atoms, and a substituted or unsubstituted aryloxy group having 6 to 30 carbon atoms, wherein each of $Ar_1$ and $Ar_2$ may be bonded to an adjacent group thereto to form a substituted or unsubstituted ring.

Each of $Ar_1$ and $Ar_2$ may be bonded to an adjacent group thereto, more specifically, be bonded to an adjacent group thereto, to form a substituted or unsubstituted ring having 5 to 12 nuclear atoms.

Each of $R_1$ to $R_4$ independently represents a substituent selected from a group consisting of deuterium, a cyano group, a nitro group, a halogen group, a hydroxyl group, a substituted or unsubstituted alkylthio group having 1 to 4 carbon atoms, a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 5 to 60 nuclear atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl groups having 6 to 30 carbon atoms, and a substituted or unsubstituted aryloxy groups having 6 to 30 carbon atoms, wherein each of $R_1$ to $R_4$ may be bonded to an adjacent group thereto to form a substituted or unsubstituted ring.

Each of $R_1$ to $R_4$ may be bonded to an adjacent group thereto, more specifically, be bonded to an adjacent group thereto, to form a substituted or unsubstituted ring having 5 to 12 nuclear atoms.

* indicates a site at which bonding occurs. The bonding to a framework of pyrene may occur.

The p is independently an integer of 1 to 4.

Each of k, l, m and n is independently an integer of 0 to 2.

[Chemical Formula 2]

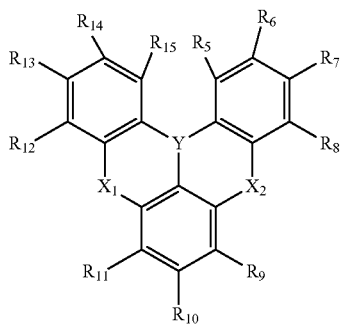

wherein in Chemical Formula 2, Y is B, N, P=O or P=S.

$X_1$ and $X_2$ are the same or different from each other, wherein each of $X_1$ and $X_2$ independently represents one selected from a group consisting of O, S, Se, $CR_{16}R_{17}$ and $NR_{18}$.

$R_5$ to $R_{18}$ are the same or different from each other, wherein each of $R_5$ to $R_{18}$ independently represents one selected from a group consisting of hydrogen, deuterium, a cyano group, a nitro group, a halogen group, a hydroxyl group, a substituted or unsubstituted alkylthio group having 1 to 4 carbon atoms, a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 5 to 60 nuclear atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl groups having 6 to 30 carbon atoms, and a substituted or unsubstituted aryloxy group having 6 to 30 carbon atoms, wherein each of $R_5$ to $R_{18}$ may be bonded to an adjacent group thereto to form a substituted or unsubstituted ring.

Each of $R_5$ to $R_{18}$ may be bonded to an adjacent group thereto, more specifically, be bonded to an adjacent group thereto, to form a substituted or unsubstituted ring having 5 to 12 nuclear atoms.

In Chemical Formula 1 and Chemical Formula 2, each of $R_1$ to $R_{18}$, $Ar_1$ and $Ar_2$ is independently substituted with at least one substituent selected from a group consisting of deuterium, a cyano group, a nitro group, a halogen group, a hydroxyl group, an alkyl group having 1 to 30 carbon atoms, a cycloalkyl group having 3 to 30 carbon atoms, an alkenyl group having 2 to 30 carbon atoms, an alkynyl group having 2 to 24 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having from 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms, and an aryloxy group having 6 to 30 carbon atoms, wherein when the at least one substituent includes a plurality of substituents, the plurality of substituents are the same or different from each other.

The organic layer may include a light-emitting layer.

In one implementation of the present disclosure, the organic electroluminescent device includes a light-emitting layer that includes the compound represented by Chemical Formula 1 as a first dopant and the compound represented by Chemical Formula 2 as a second dopant. The light-emitting layer uses both the first dopant and the second dopant to achieve color characteristic and efficiency resulting from the second dopant emitting light while improving the lifespan characteristic.

In one implementation of the present disclosure, in Chemical Formula 1, p may be 2.

Specifically, the compound represented by Chemical Formula 1 may include a compound represented by Chemical Formula 3.

[Chemical Formula 3]

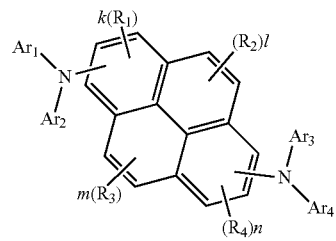

In Chemical Formula 3, each of $R_1$ to $R_4$, $Ar_1$, $Ar_2$, k, l, m and n is as defined with reference to Chemical Formula 1. $Ar_3$ and $Ar_4$ are as defined with reference to $Ar_1$ and $Ar_2$. Particularly, in Chemical Formula 3, each of $R_1$ to $R_4$ independently represents one selected from a group consisting of hydrogen, cyano group, methyl, ethyl, isopropyl, trimethylsilyl (TMS), dimethylamino group, phenyl, biphenyl, naphthyl, anthracenyl, phenanthryl, pyrenyl, or bonds to an adjacent group thereto to form a substituted or unsubstituted ring; and each of $Ar_1$ to $Ar_4$ independently represents a phenyl unsubstituted or substituted by at least one substituent selected from the group consisting of deuterium, MeO—, methyl, t-butyl, $CF_3$—, a halogen group, —OH, isopropyl and trimethylsilyl; biphenyl; naphthyl; 9,9-dimethylfluorenyl; pyridinyl; dibenzothiophenyl; dibenzofuranyl or phenyl benzofuranyl.

Specifically, the compound represented by Chemical Formula 1 may include one of following compounds 1-1 to 1-110:

1-1

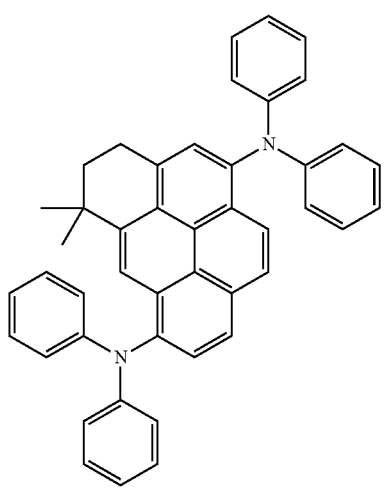

1-2
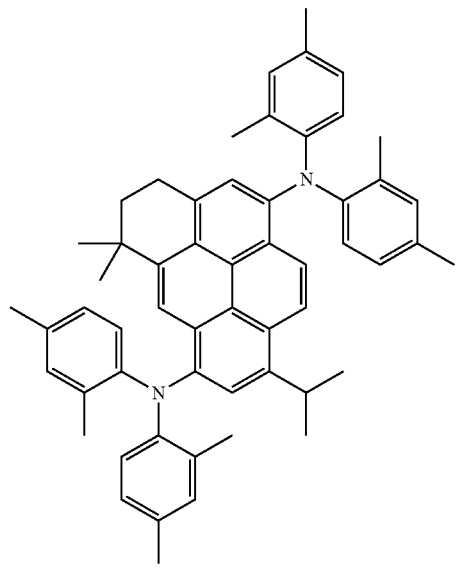
1-3
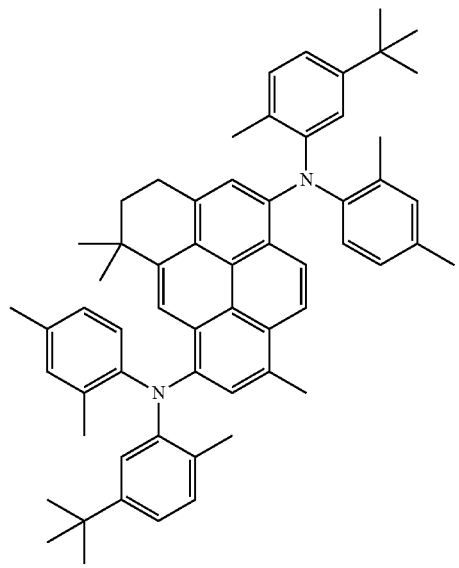
1-4
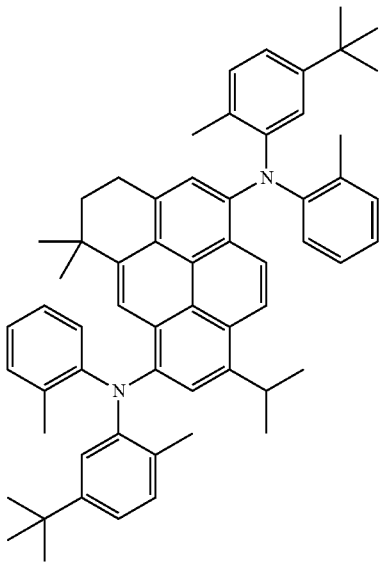
1-5
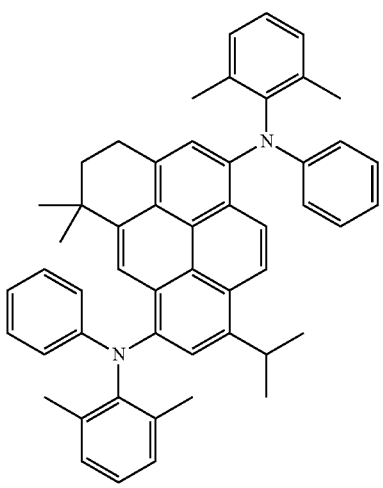
1-6
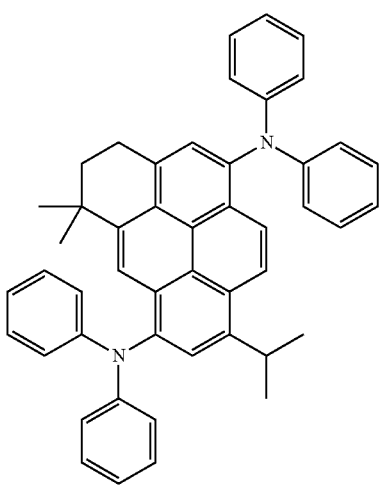

1-7
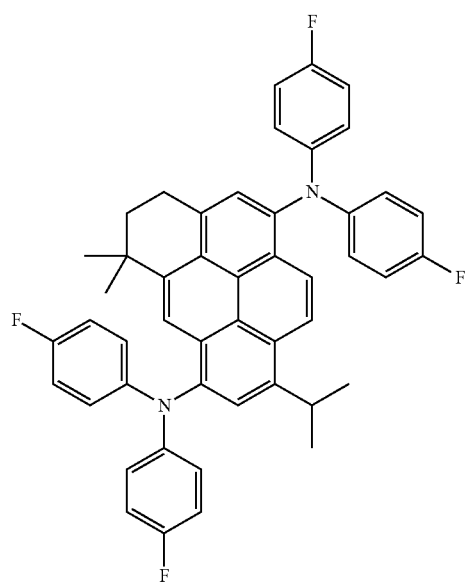
1-9
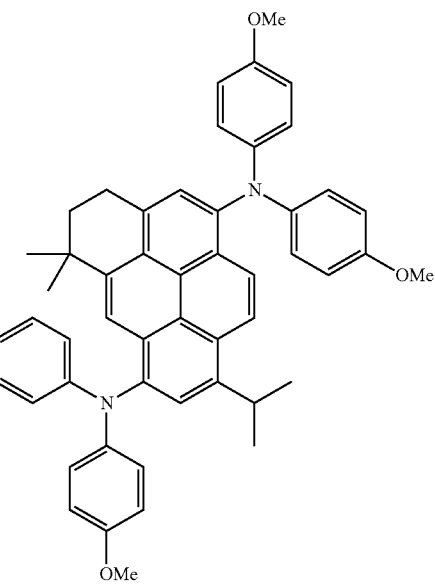
1-8
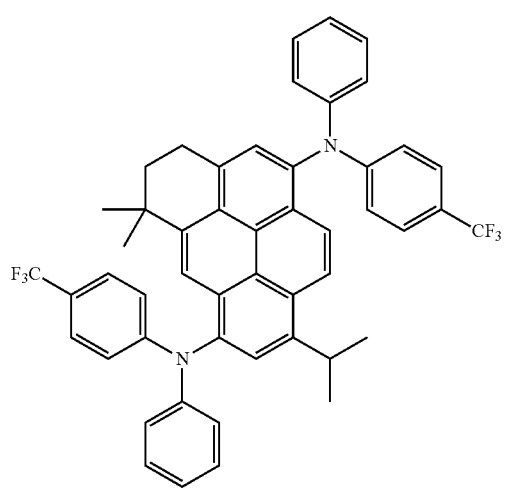
1-10
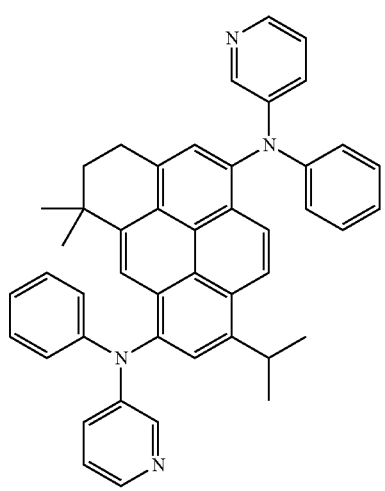

1-11
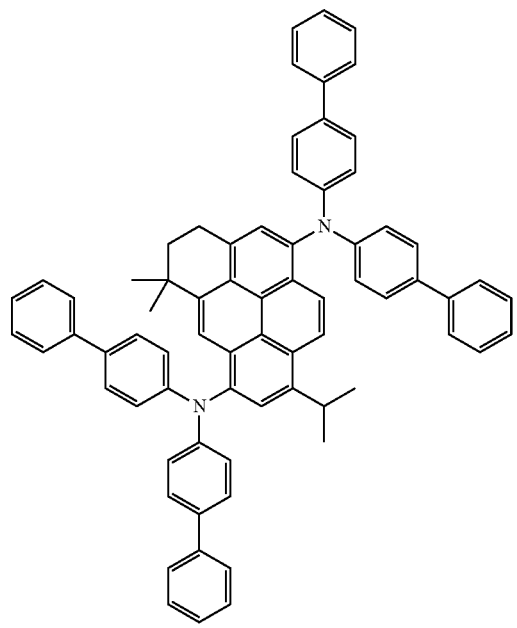
1-13
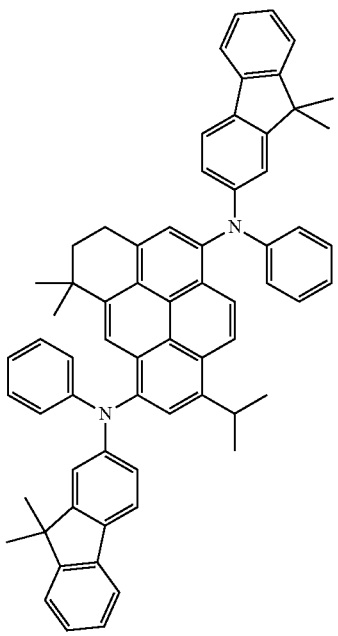
1-12
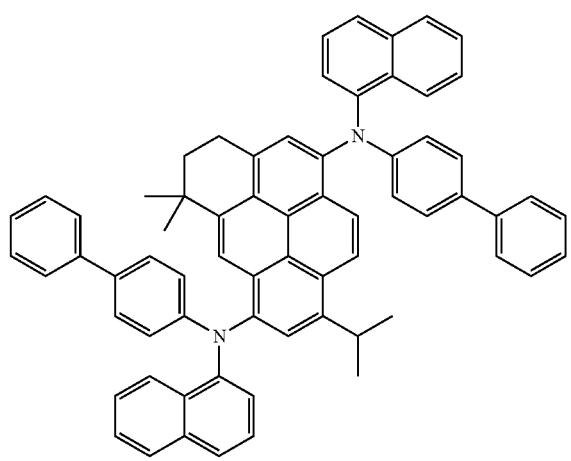
1-14
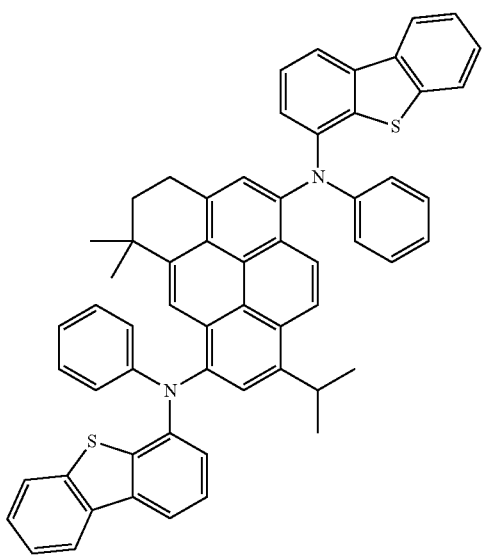

1-15
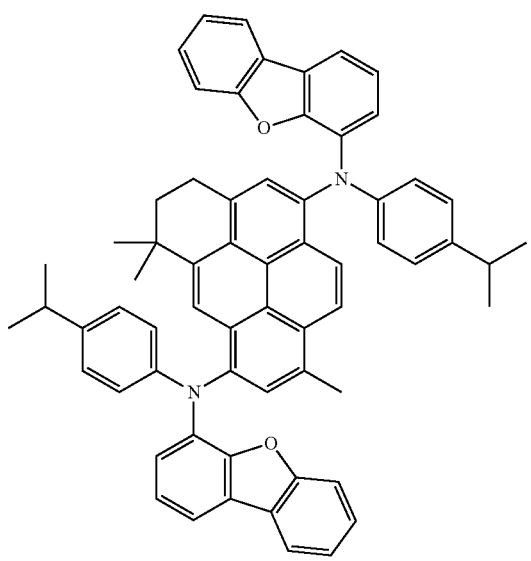
1-16
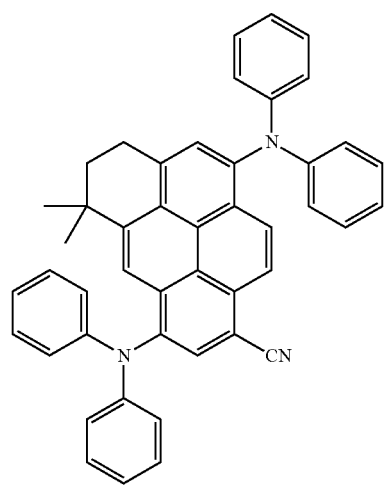
1-17
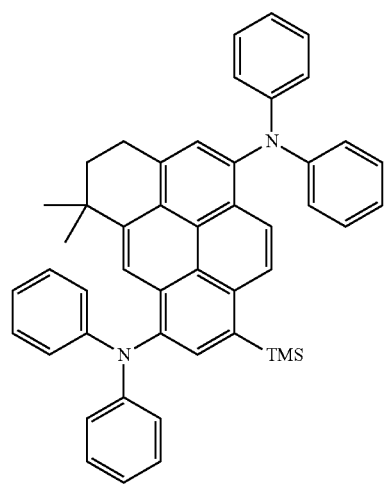
1-18
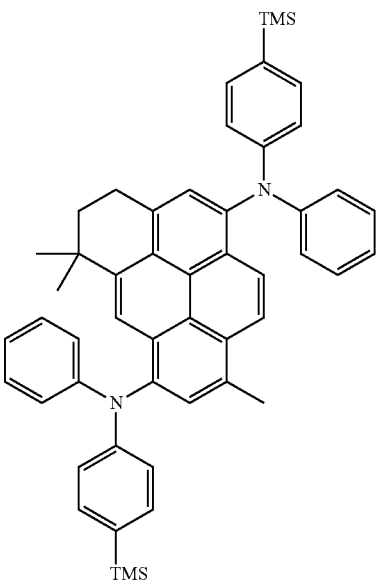
1-19
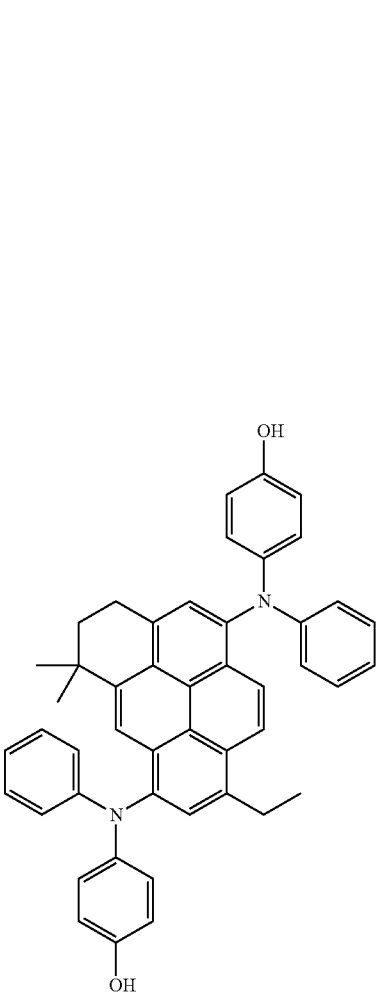

1-20
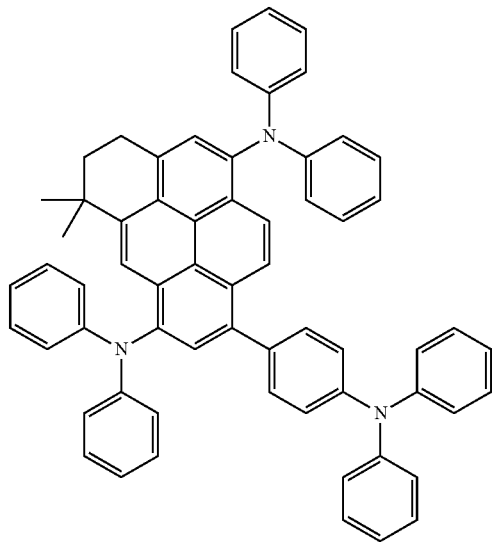
1-21
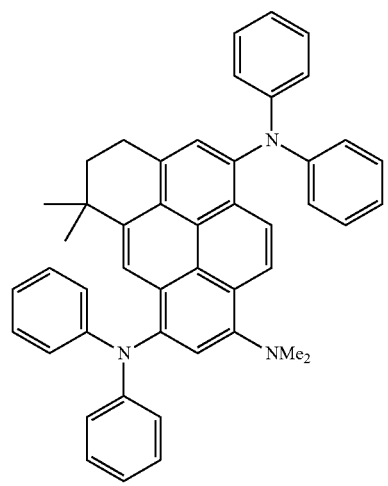
1-22
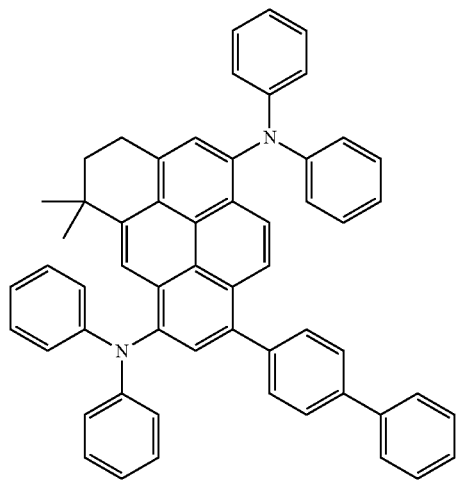
1-23
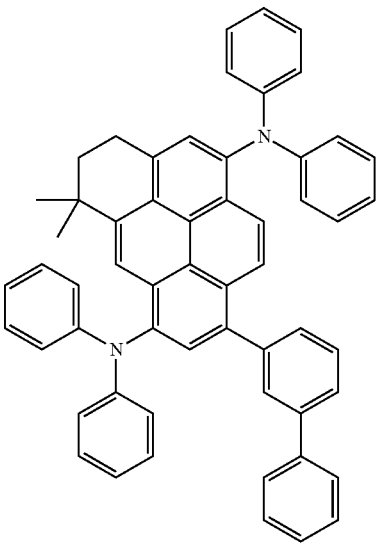
1-24
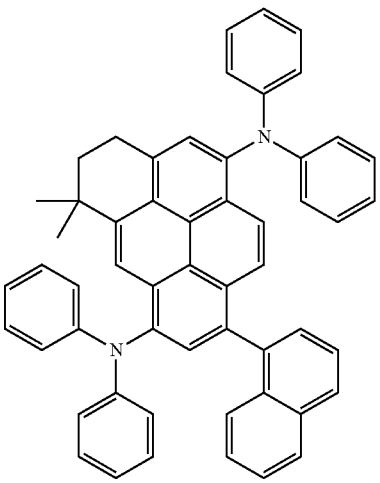
1-25
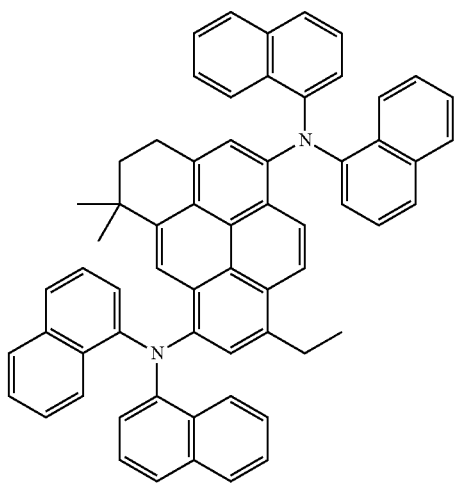

1-26
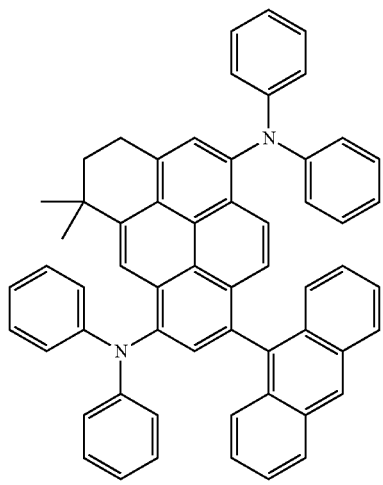
1-27
1-28
1-29
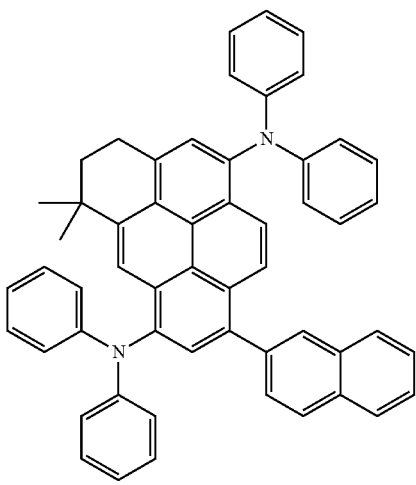
1-30
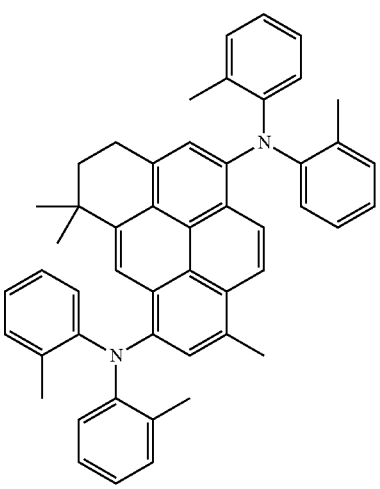
1-31
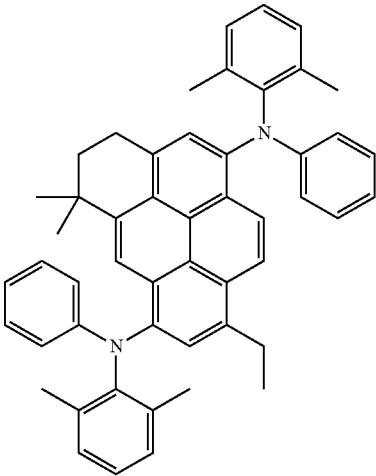

-continued
1-32
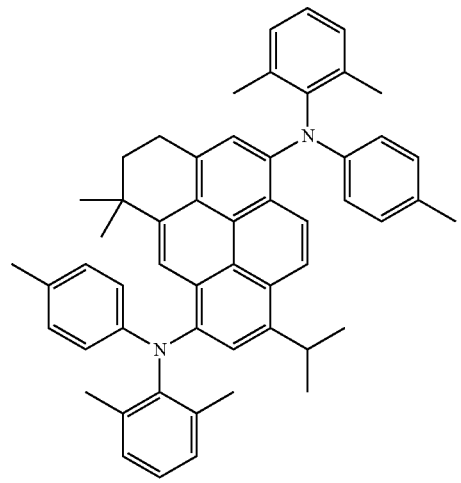
1-33
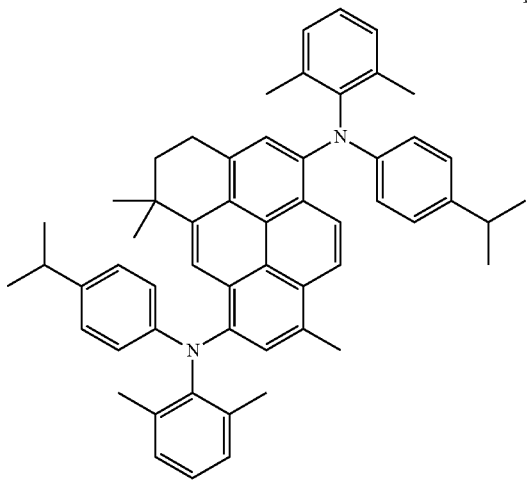
1-34
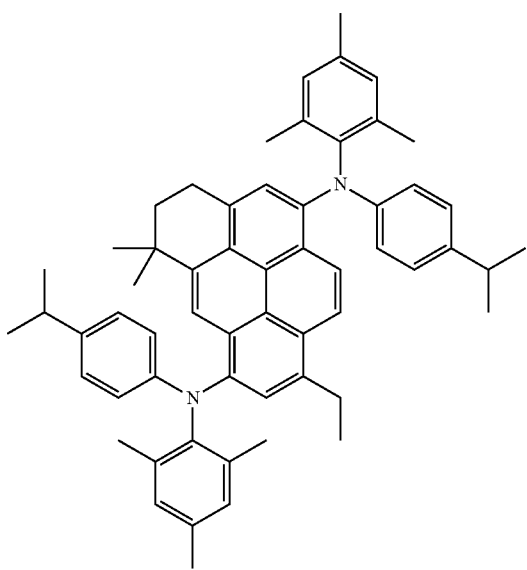
-continued
1-35
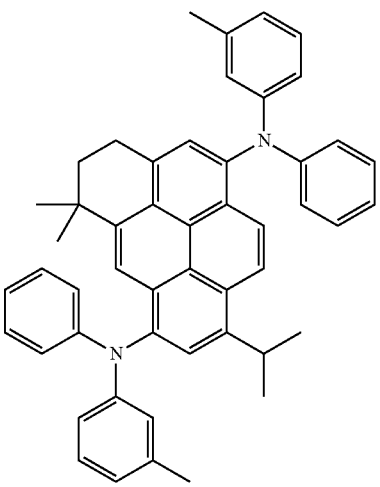
1-36
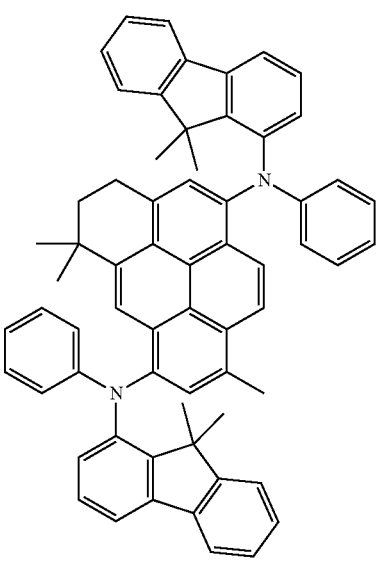
1-37
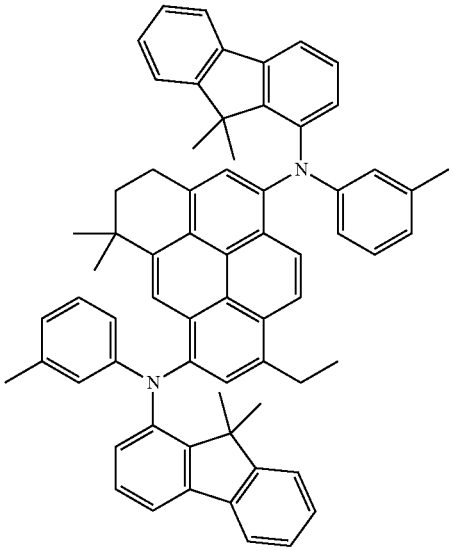

1-38
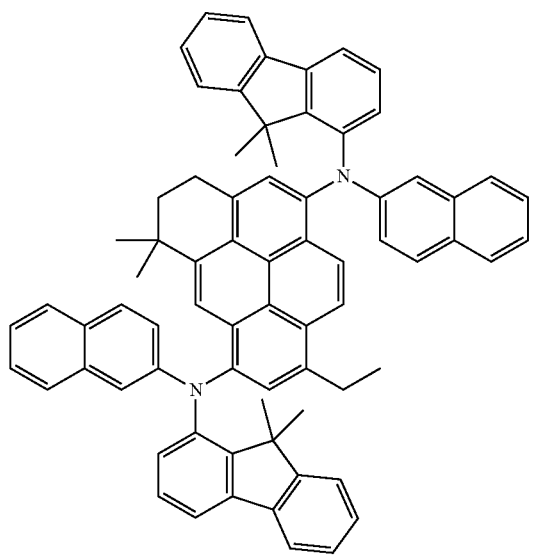
1-39
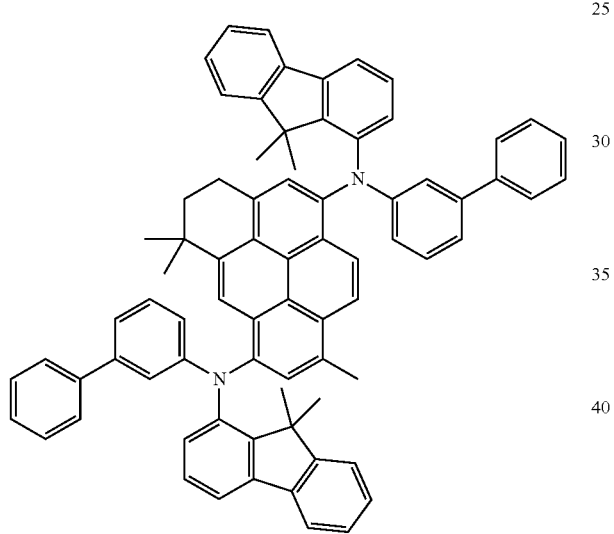
1-40
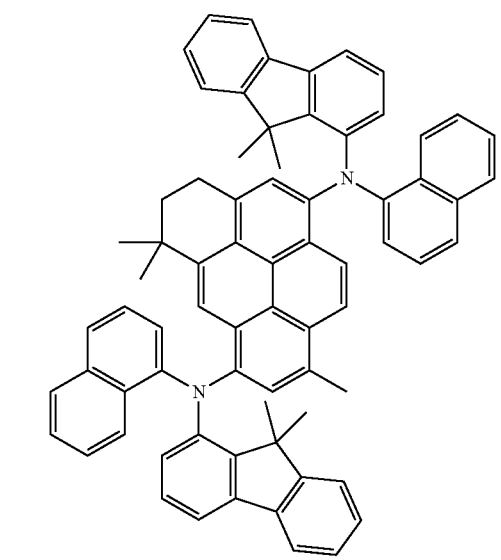
1-41
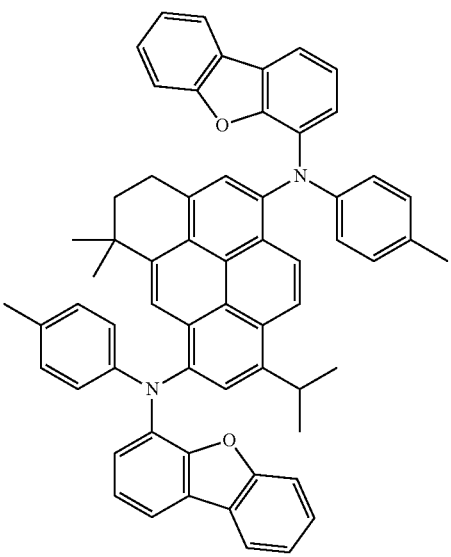
1-42
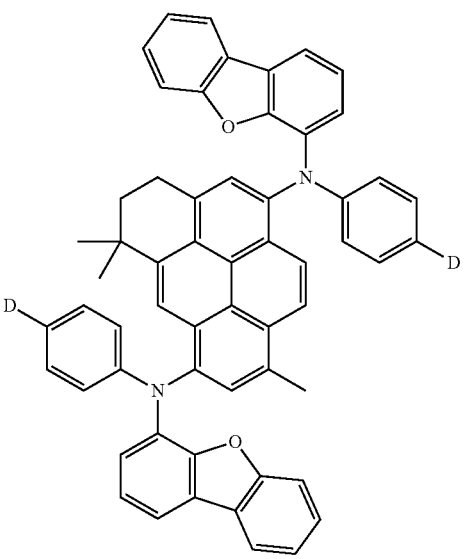
1-43
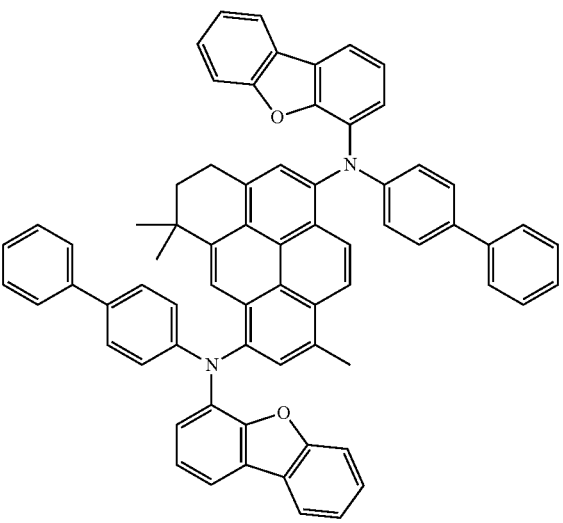

1-44
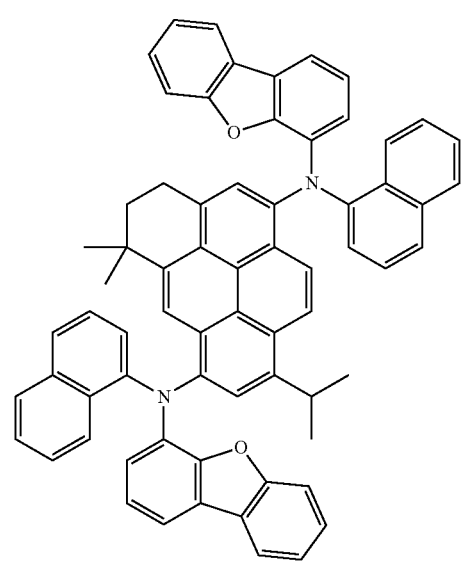
1-45
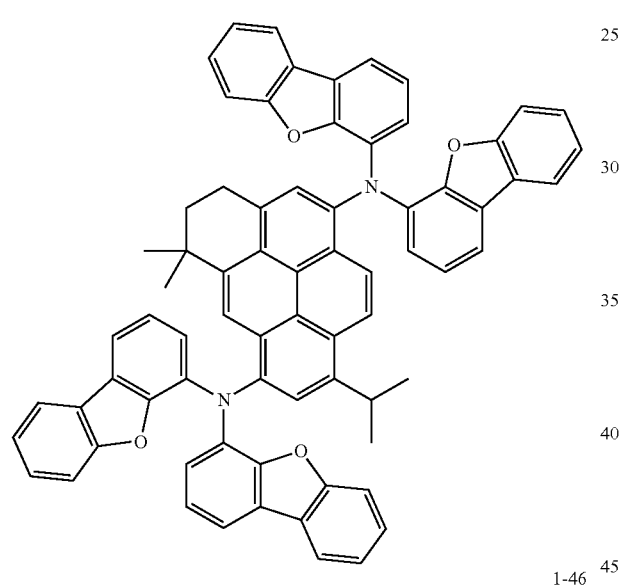
1-46
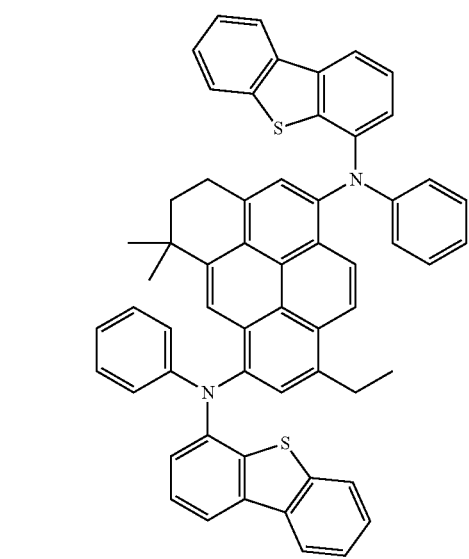
1-47
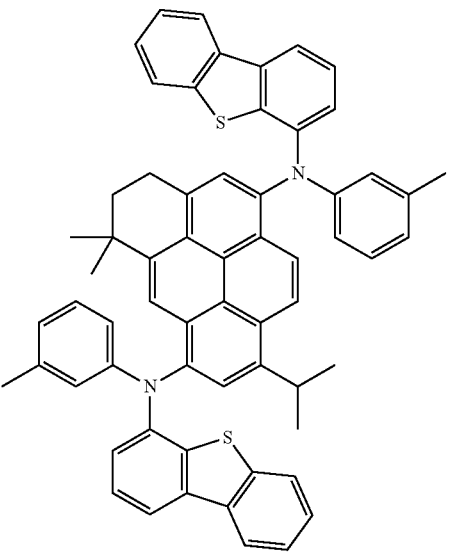
1-48
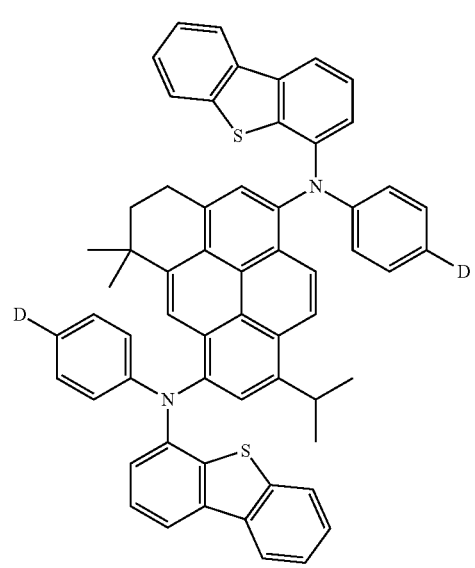
1-49
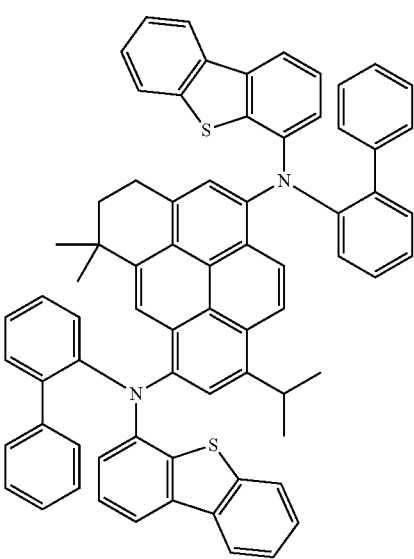

1-50
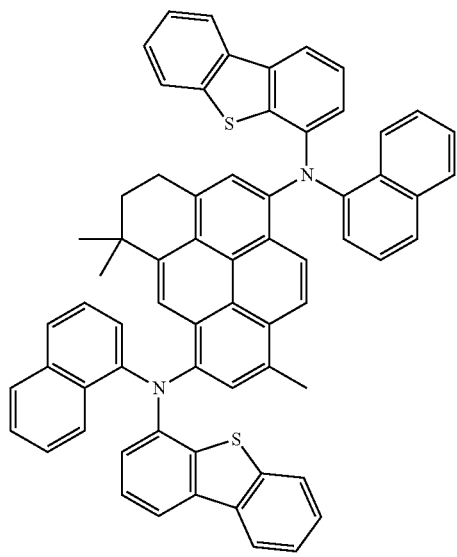
1-51
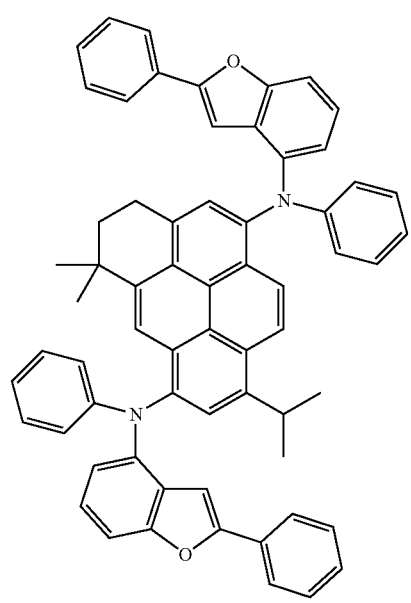
1-52
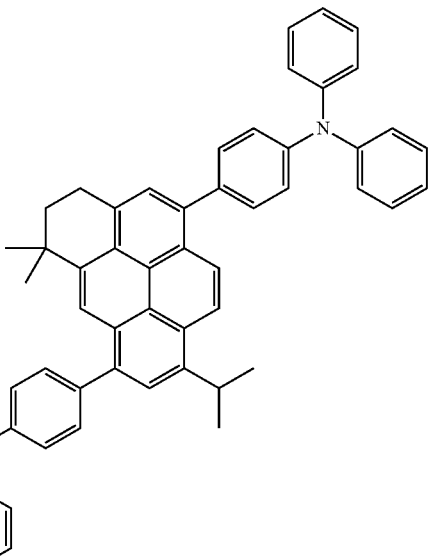
1-53

1-54
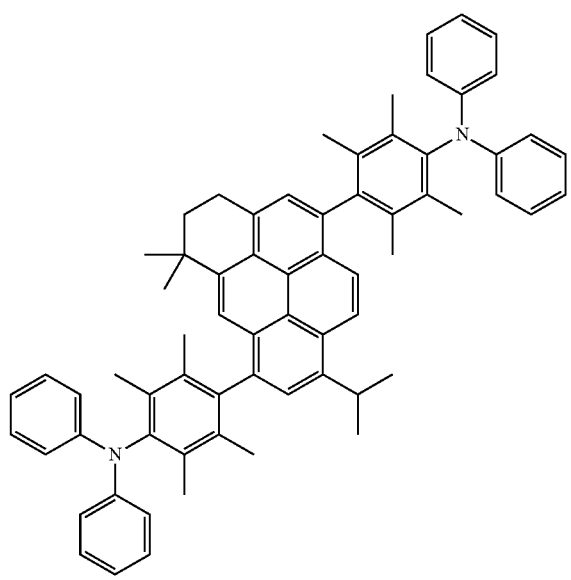
1-55
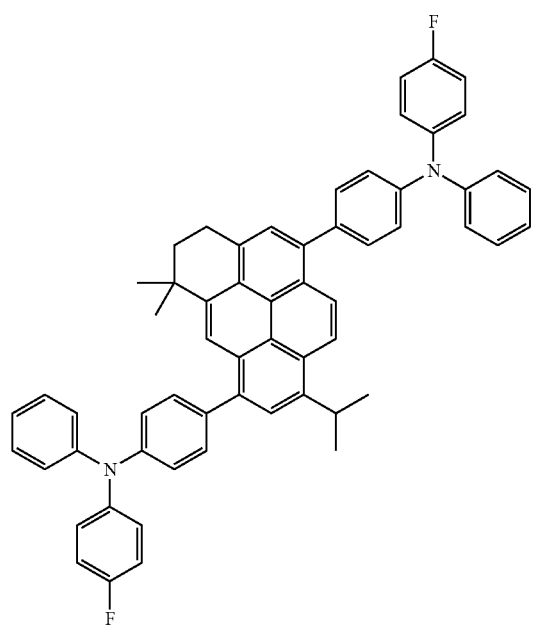
1-56
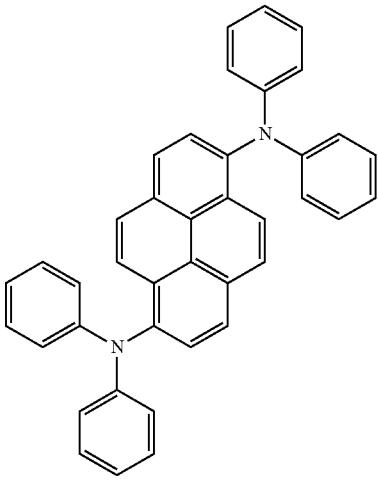
1-57
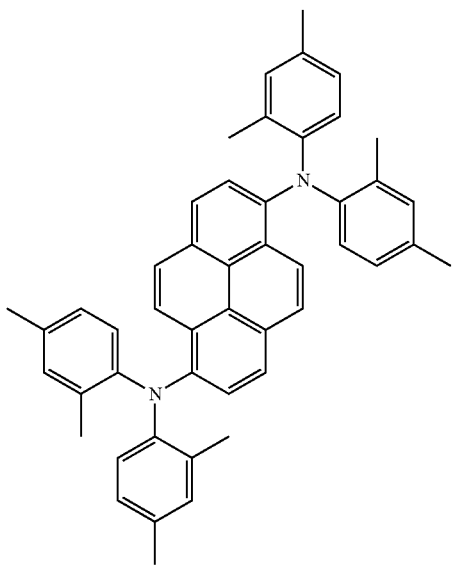
1-58
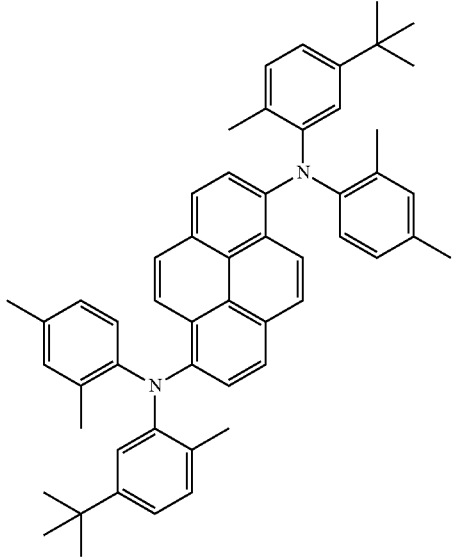

1-59
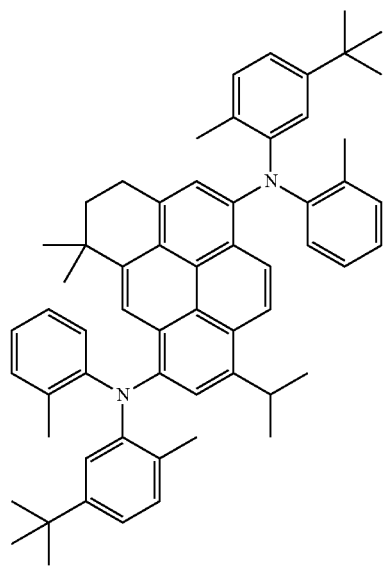
1-60
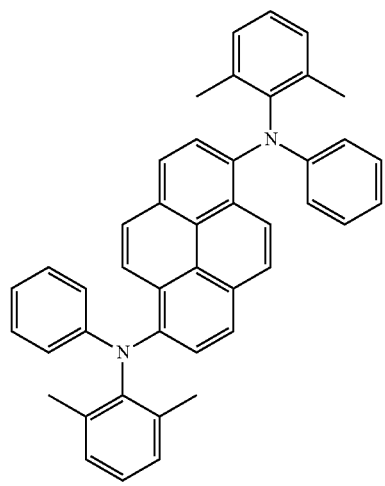
1-61
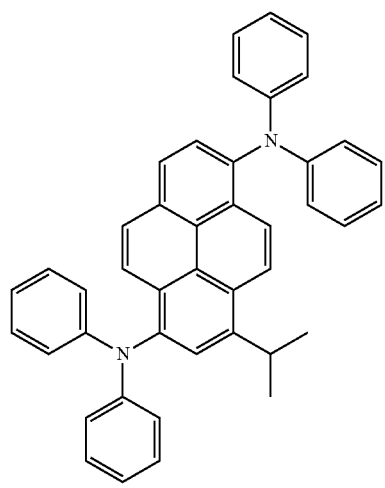
1-62
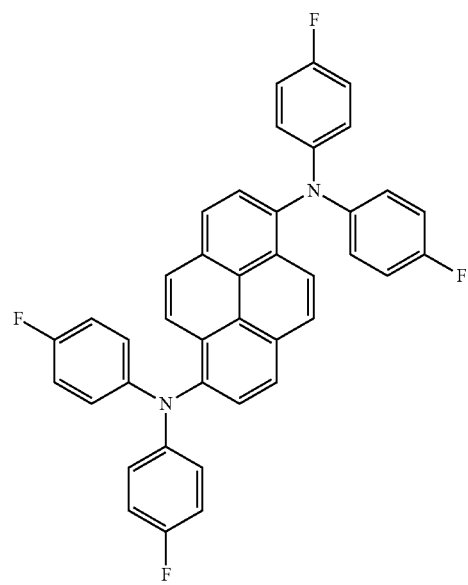
1-63
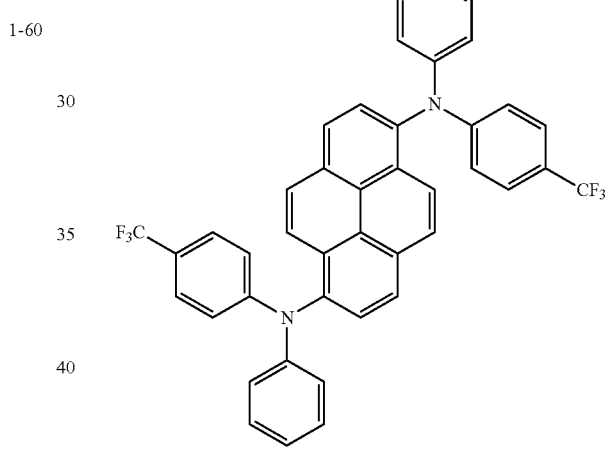
1-64
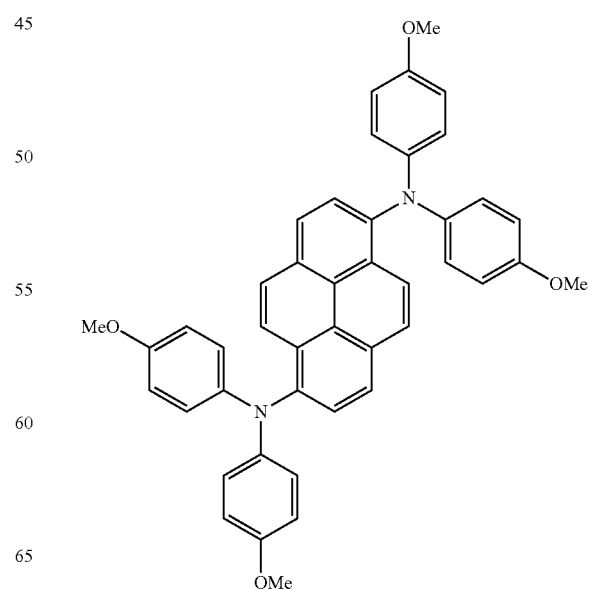

1-65
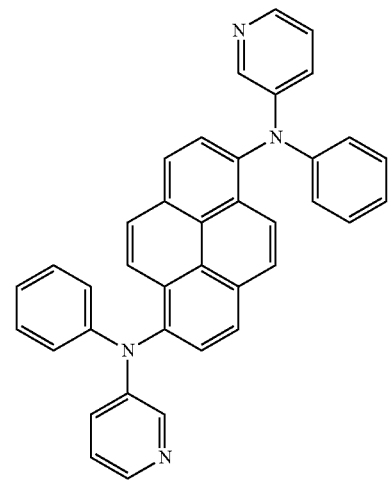
1-66
1-68
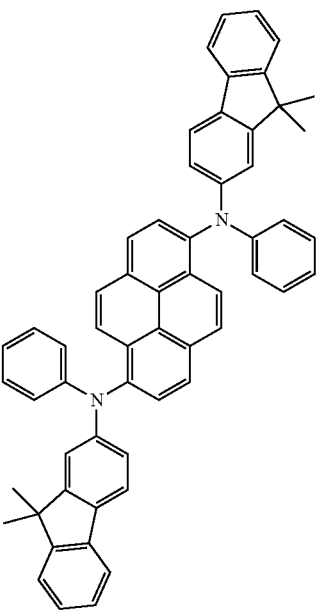
1-67
1-69
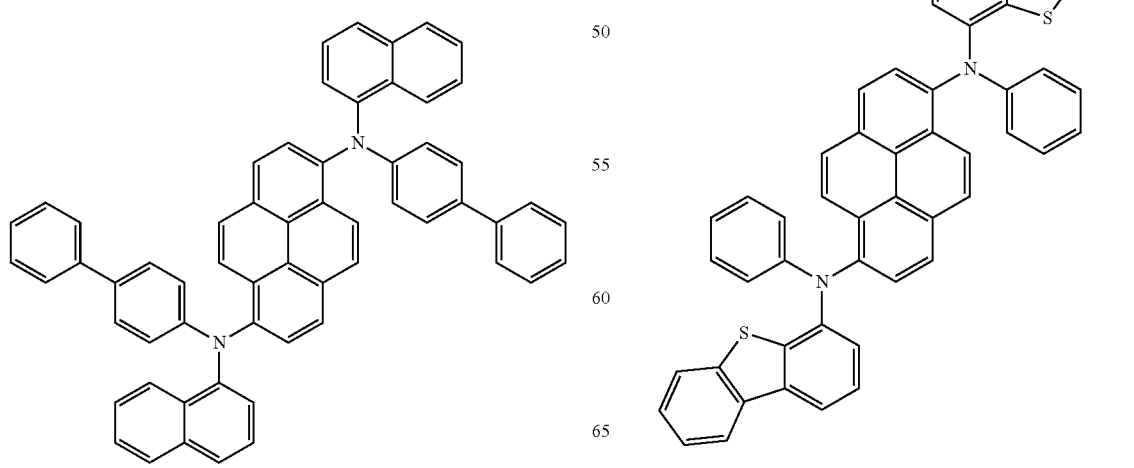

1-70
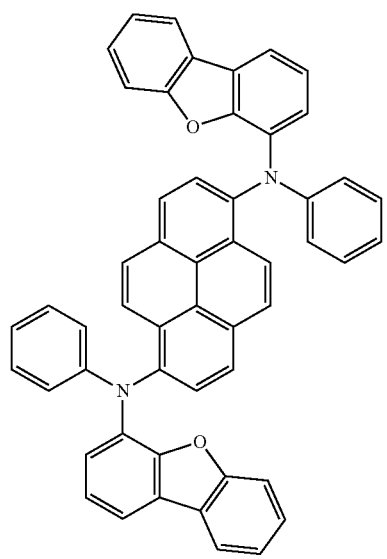
1-71
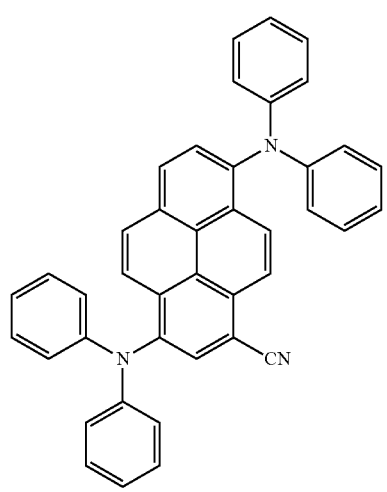
1-72
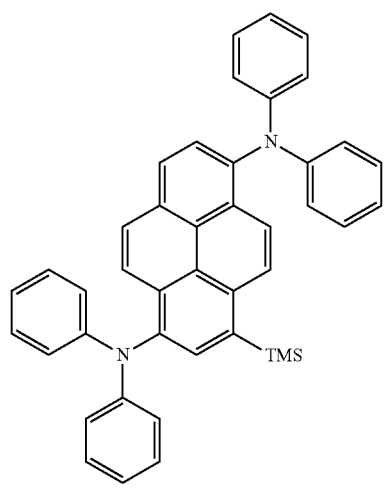
1-73
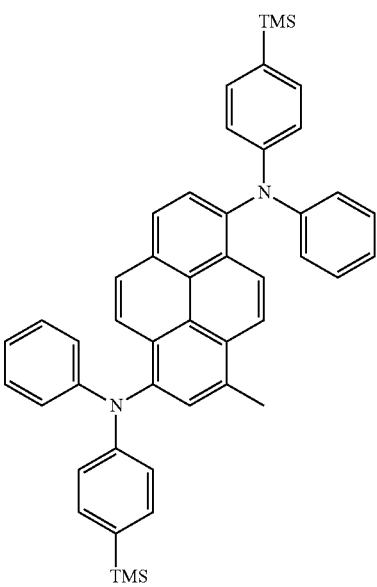
1-74
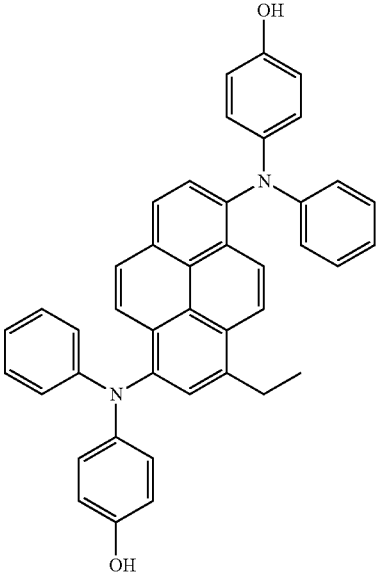

1-75
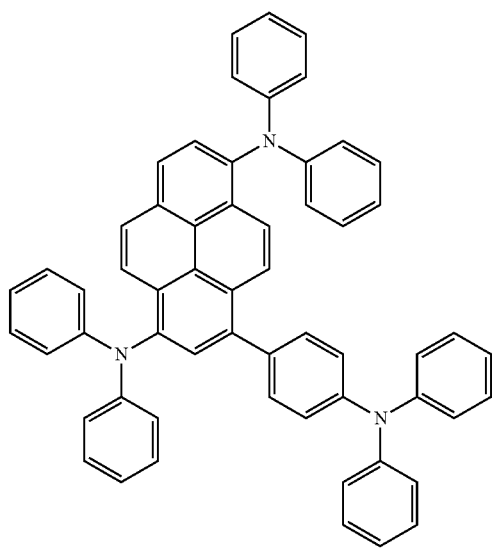
1-76
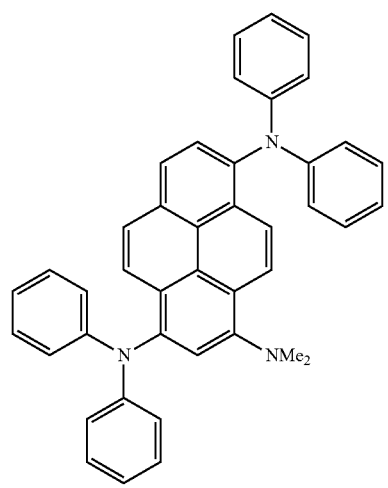
1-77
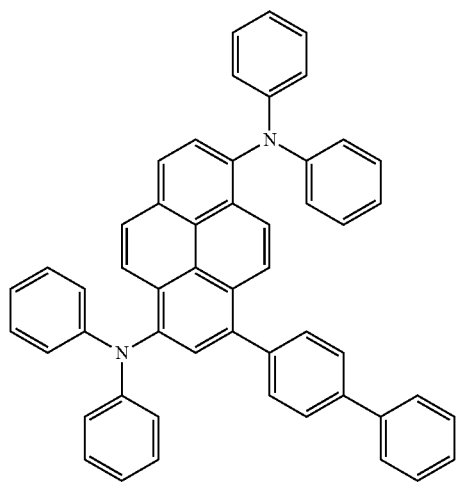
1-78
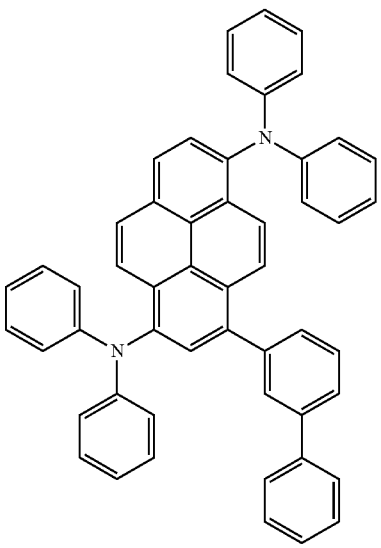
1-79
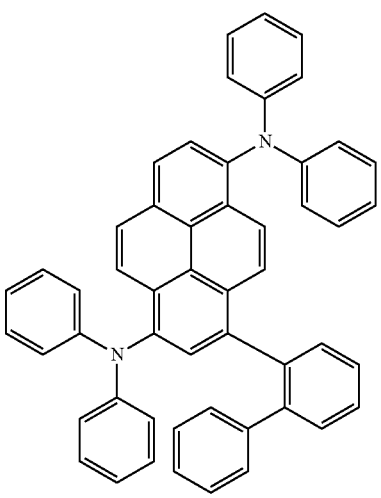
1-80
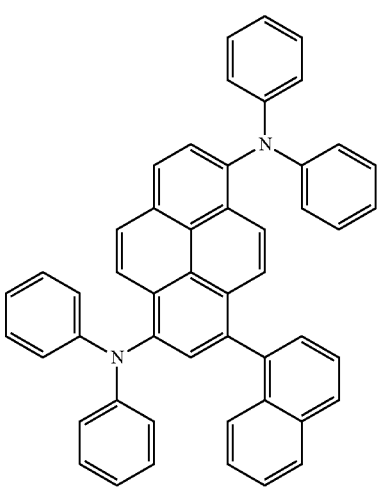

1-81
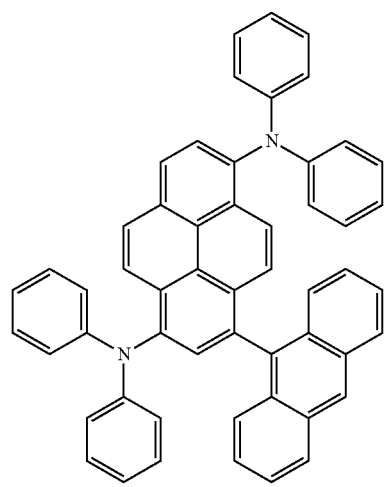
1-82
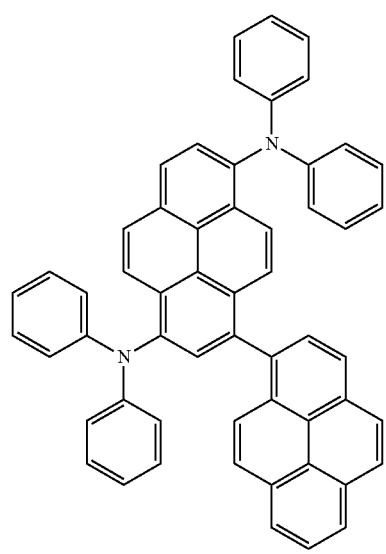
1-83
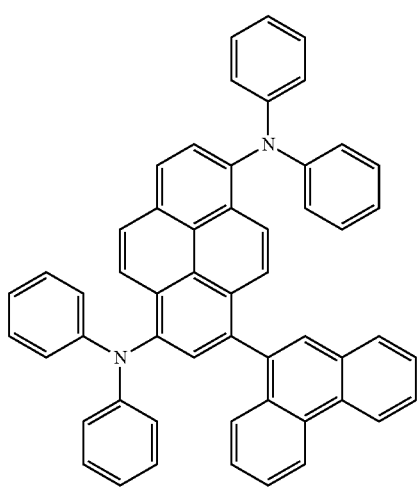
1-84
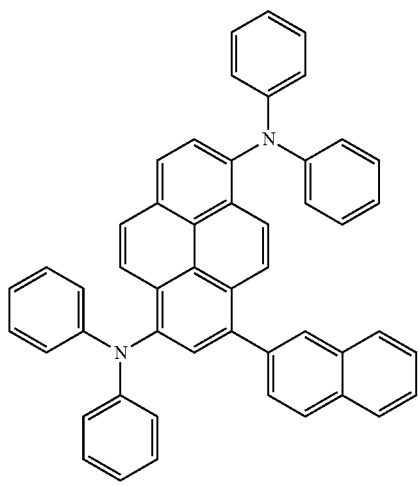
1-85
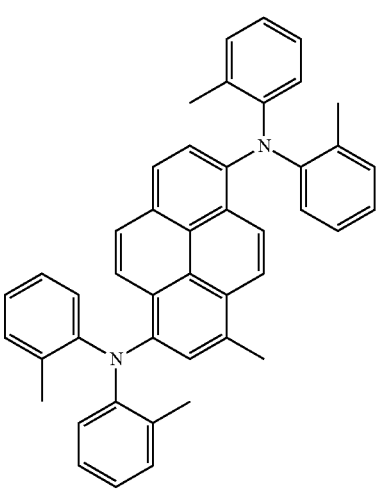
1-86
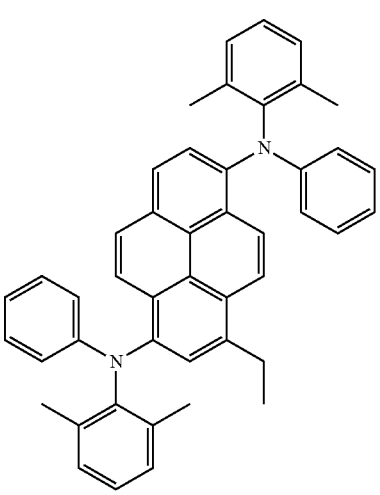

1-87
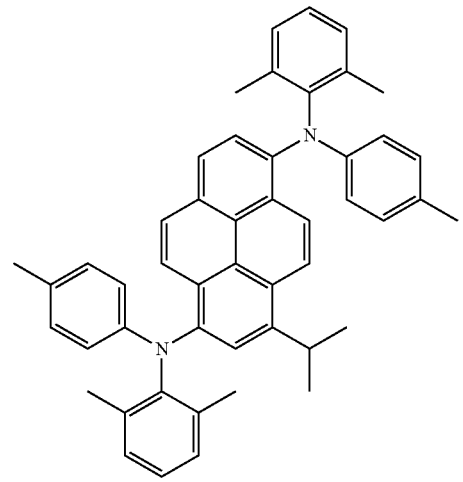
1-88
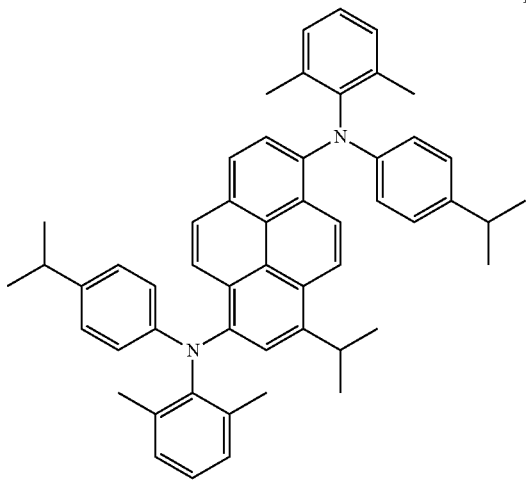
1-89
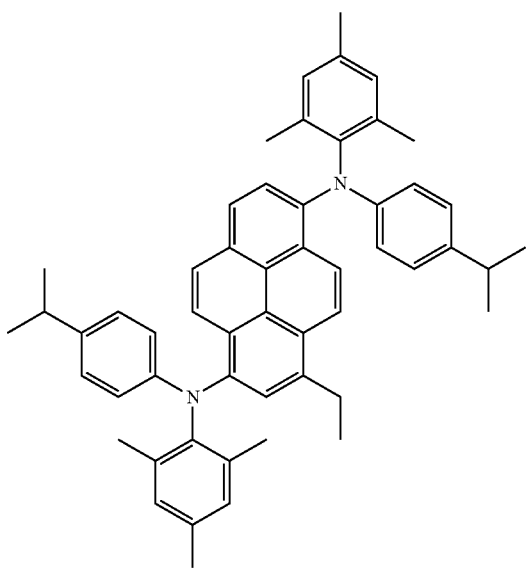
1-90
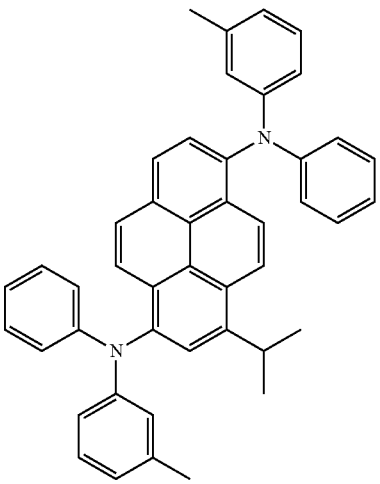
1-91
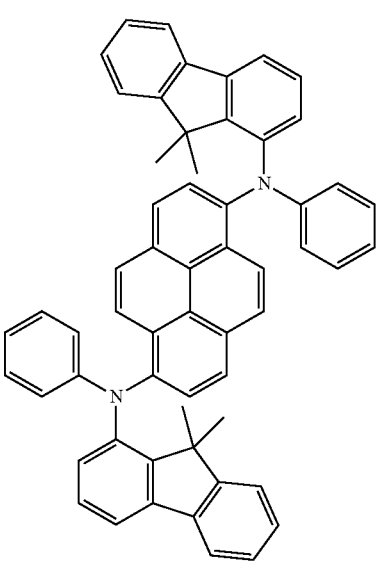
1-92
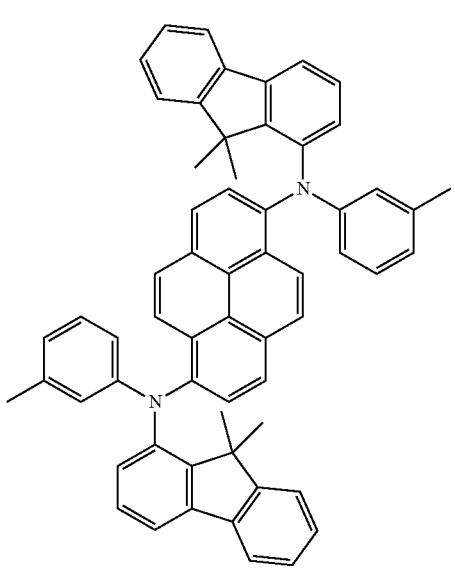

1-93
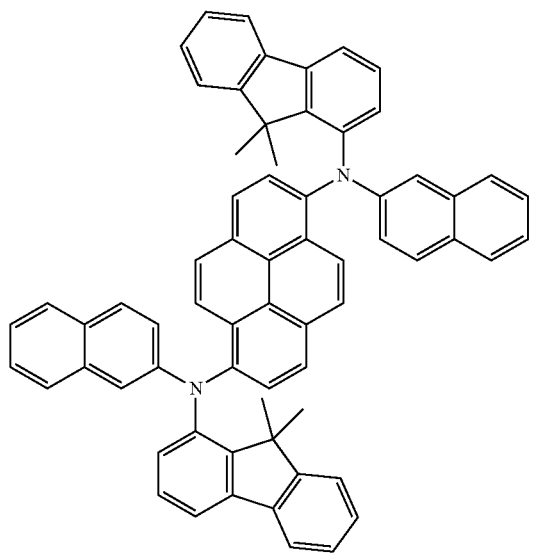
1-94
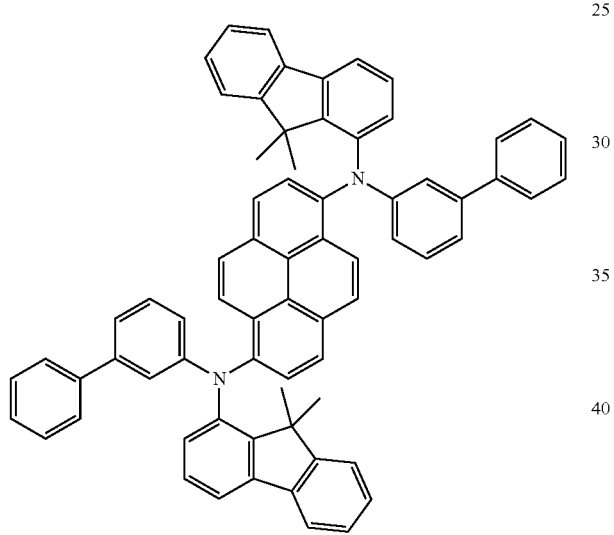
1-95
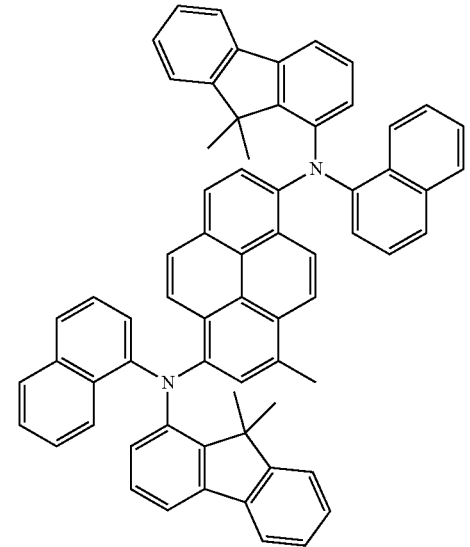
1-96
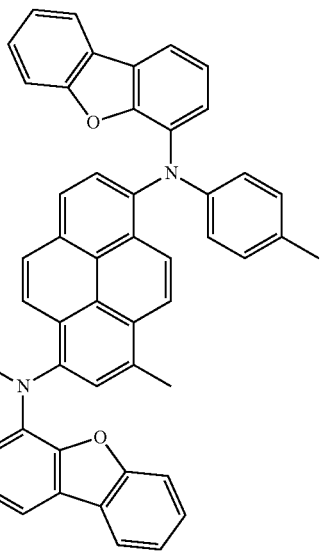
1-97
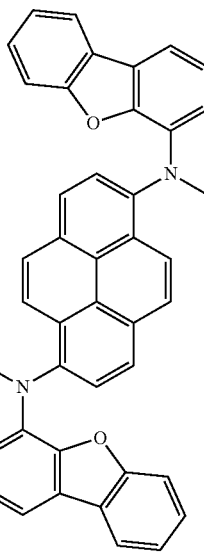
1-98
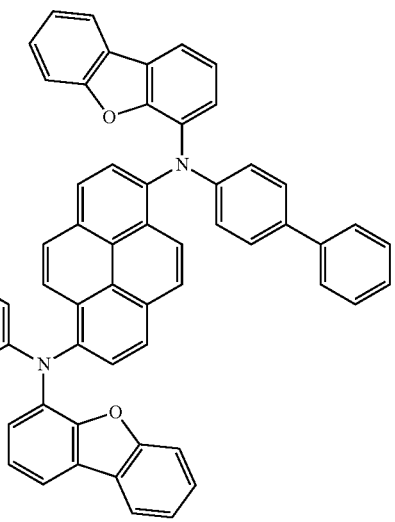

1-99
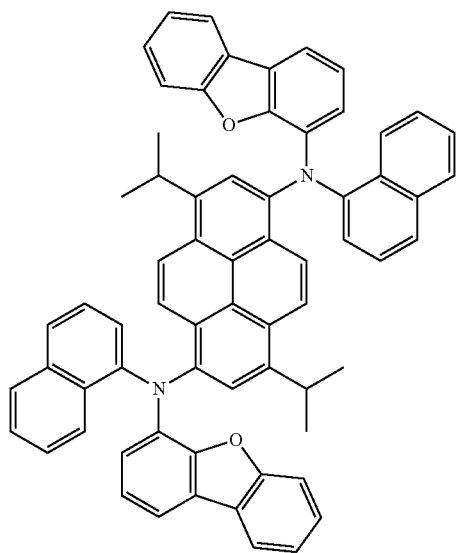
1-101
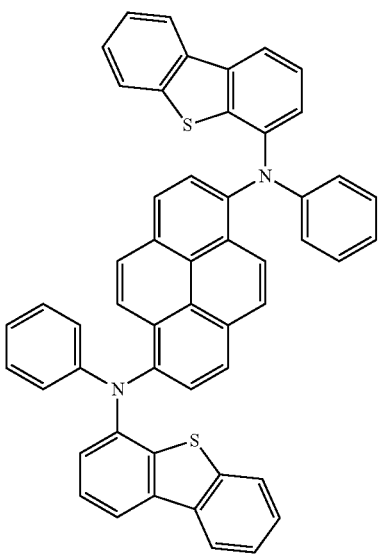
1-100
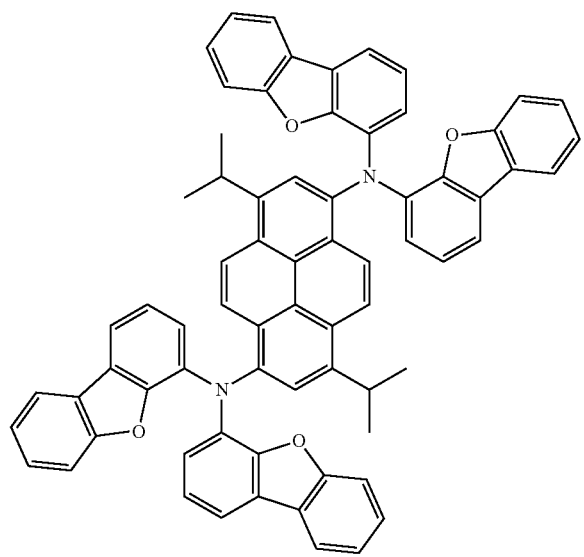
1-102
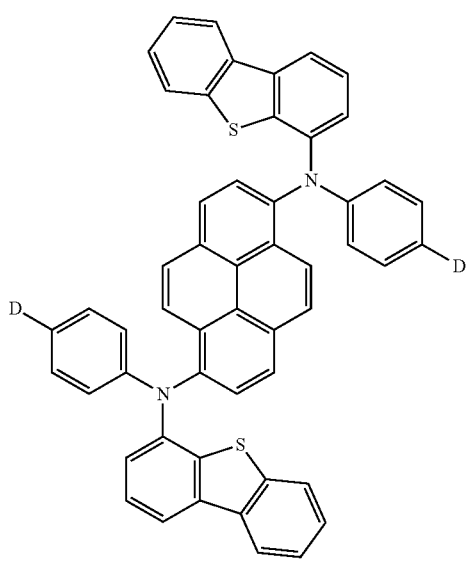

1-103
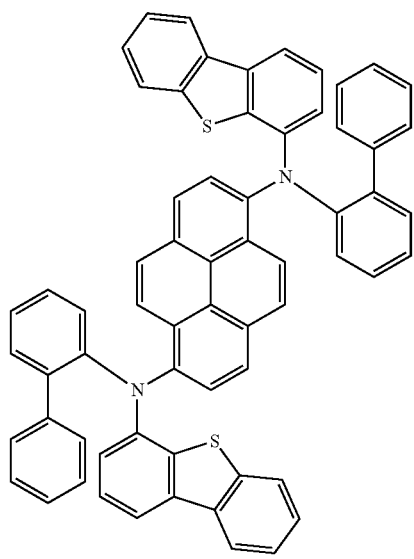
1-105
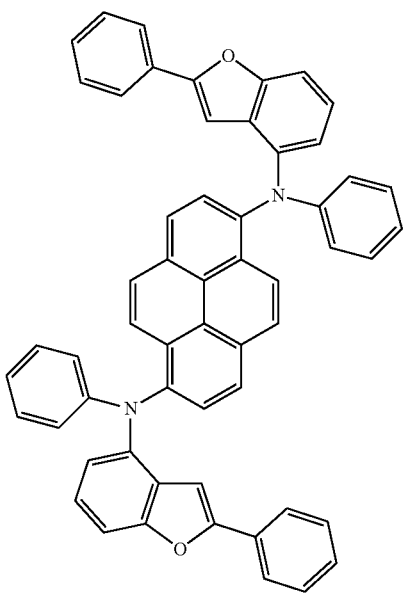
1-106
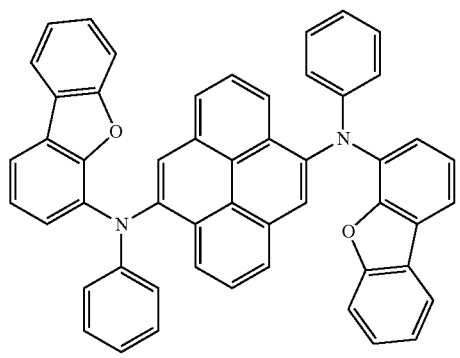
1-104
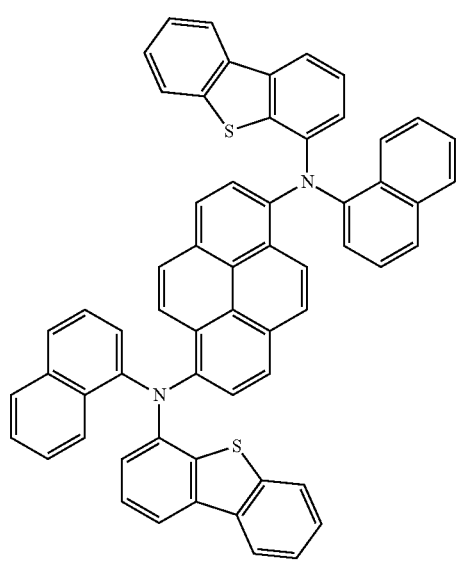
1-107
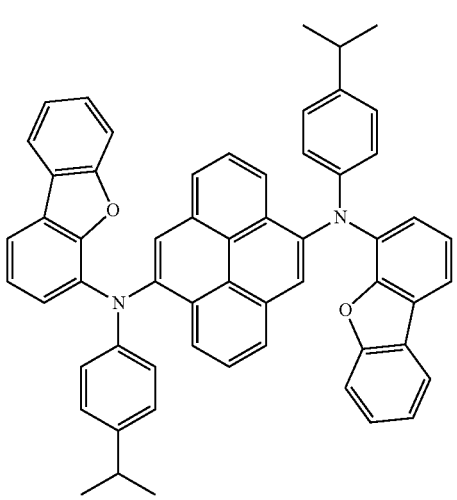

-continued 1-108

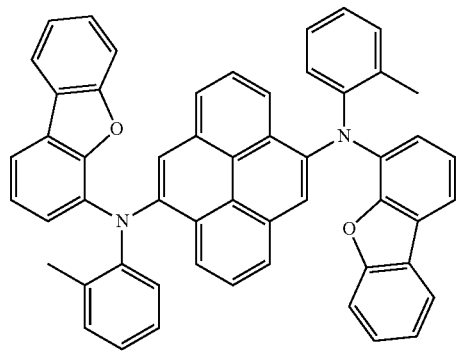

1-109

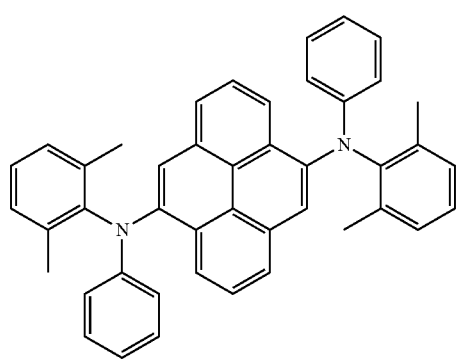

1-110

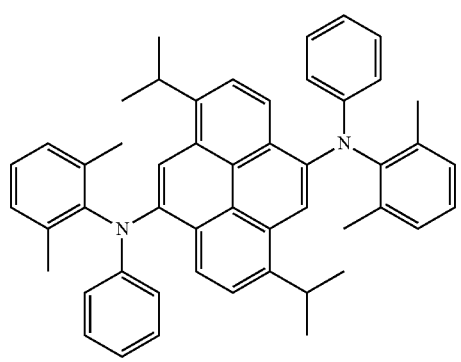

In one implementation of the present disclosure, the compound represented by Chemical Formula 2 may include a compound represented by Chemical Formula 4.

[Chemical Formula 4]

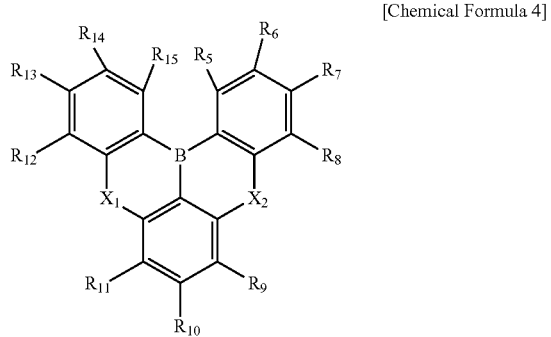

In Chemical Formula 4, each of $X_1$ and $X_2$ is independently selected from a group consisting of O and $NR_{18}$. $R_5$ to $R_{15}$ and $R_{18}$ are the same as defined with reference to Chemical Formula 2.

Particularly, in Chemical Formula 4, each of $X_1$ and $X_2$ independently represents $NR_{18}$, and $R_{18}$ independently represents an unsubstituted or substituted phenyl, naphthyl, biphenyl or terphenyl.

Specifically, the compound represented by Chemical Formula 2 may include one selected from a group consisting of following compounds 2-1 to 2-85:

2-1

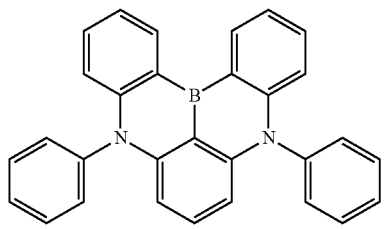

2-2

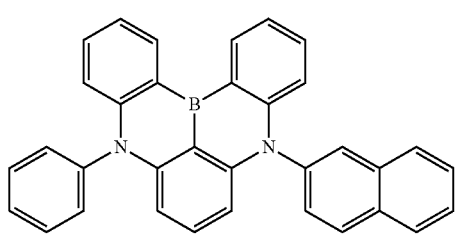

2-3

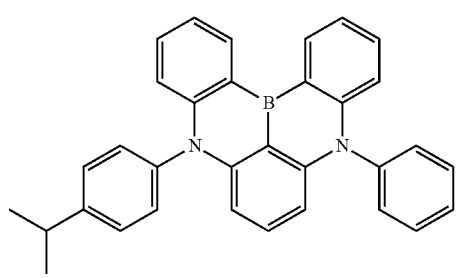

2-4

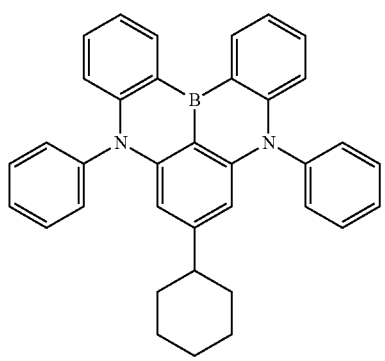

2-5
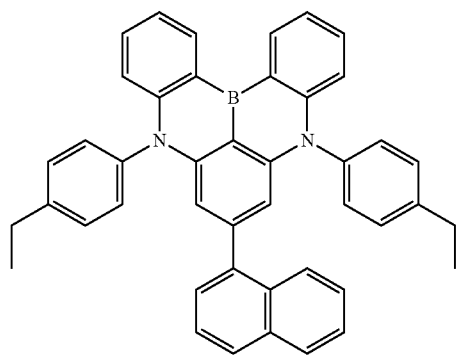
2-6
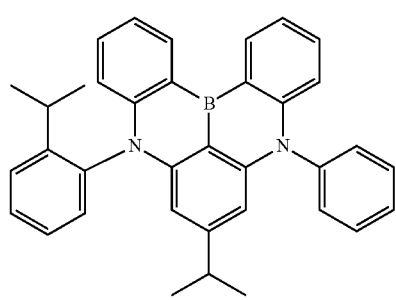
2-7
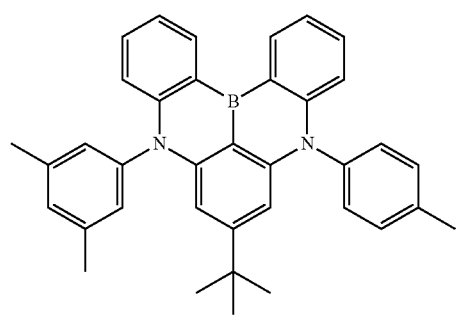
2-8
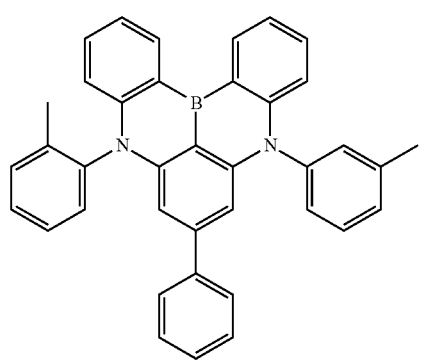
2-9
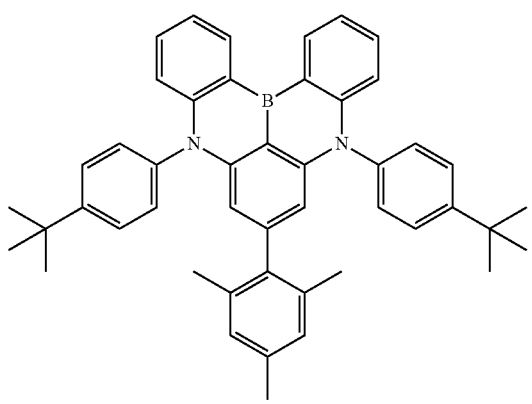
2-10
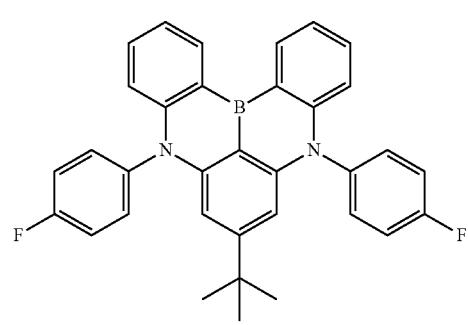
2-11
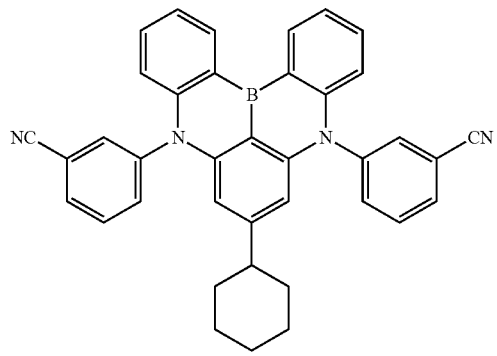
2-12
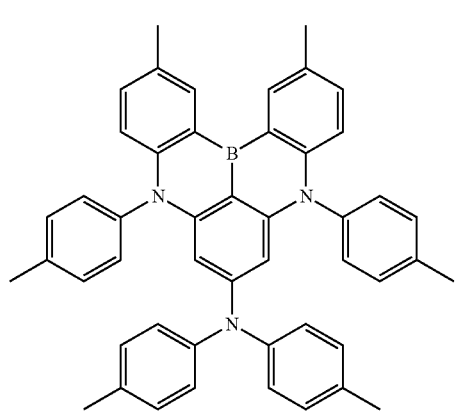

-continued
2-13
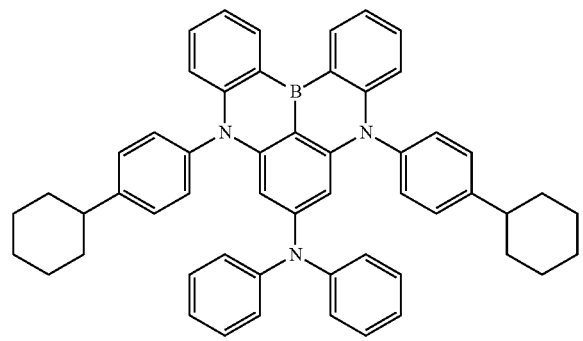
2-17
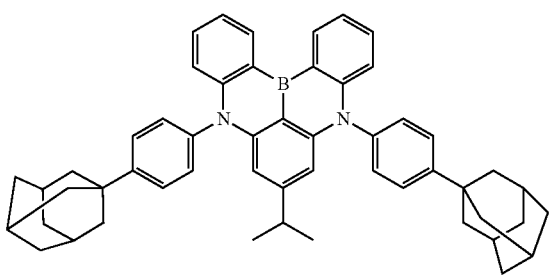
2-14
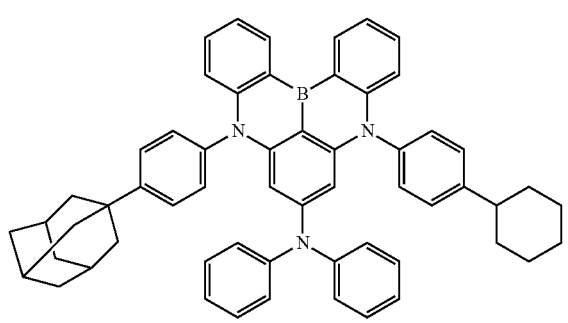
2-18
2-15
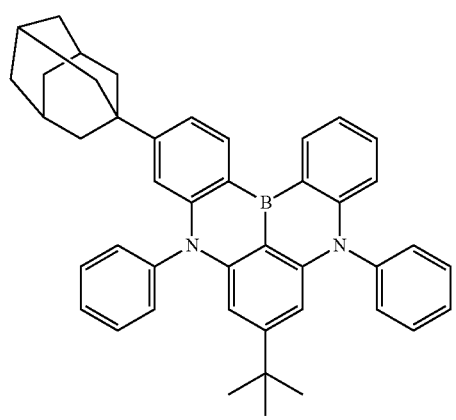
2-19
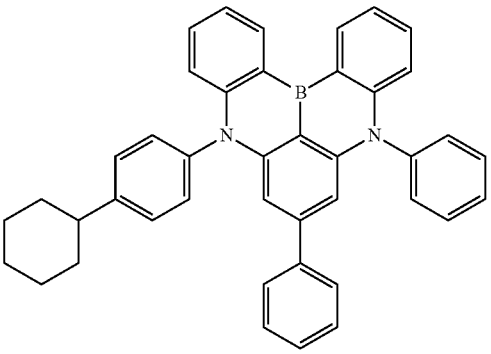
2-16
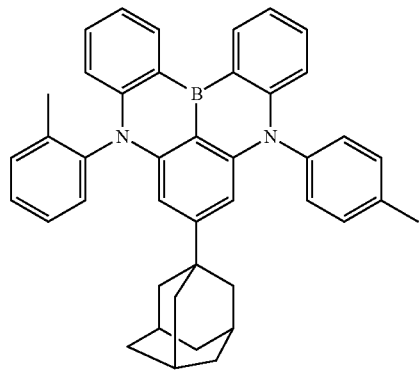
2-20

-continued
2-16
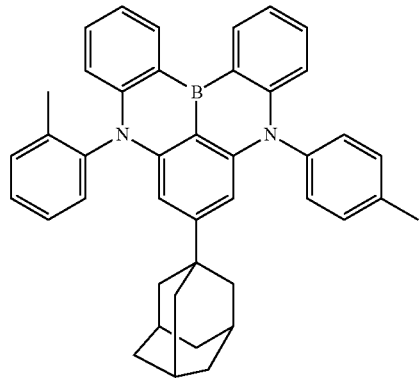
2-17
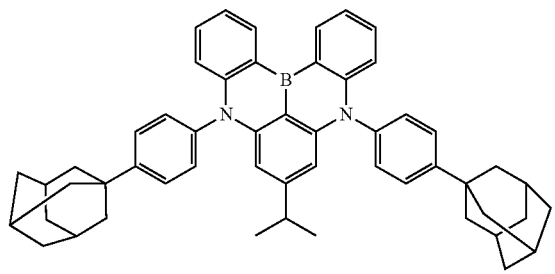
2-18
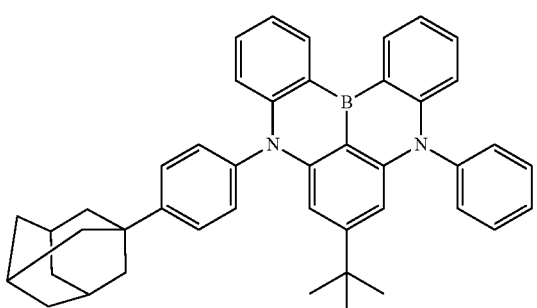
2-19
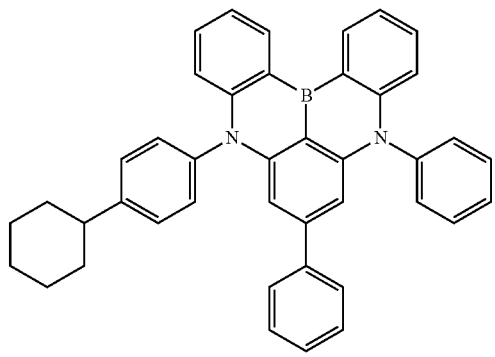
-continued
2-20
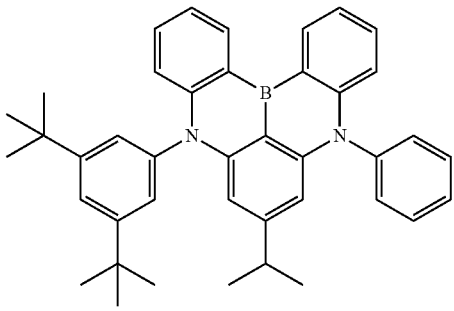
2-21
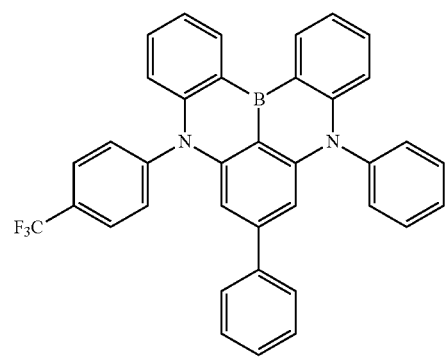
2-22
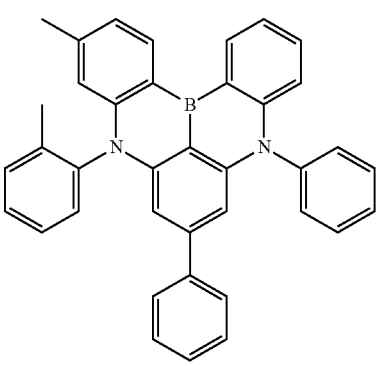
2-23
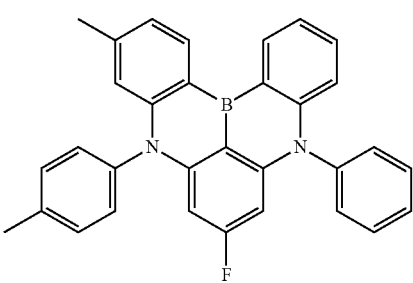

2-24
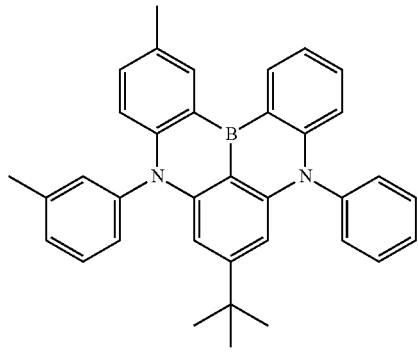
2-28
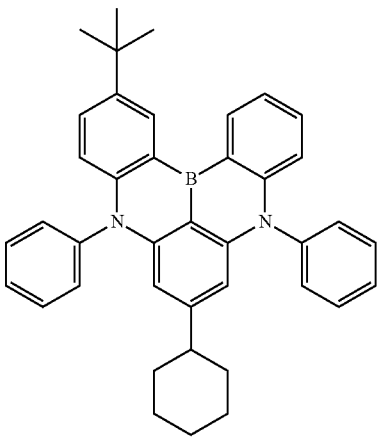
2-25
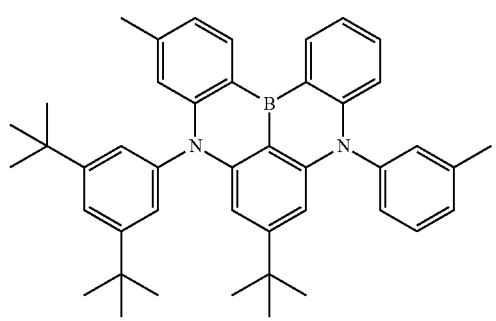
2-29
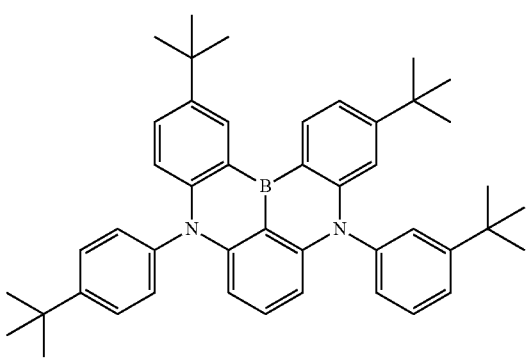
2-26
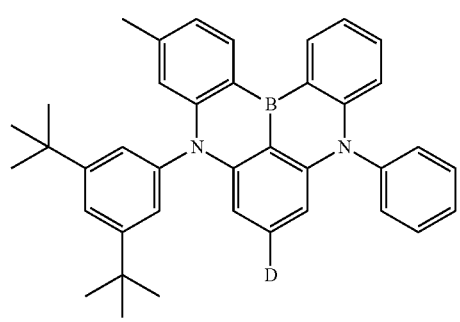
2-27
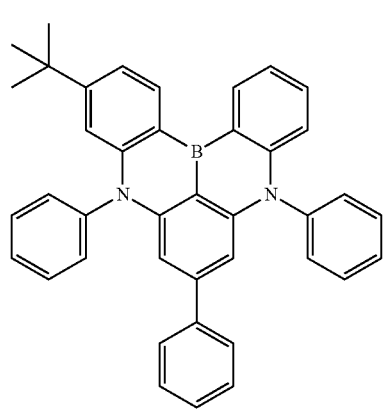
2-30
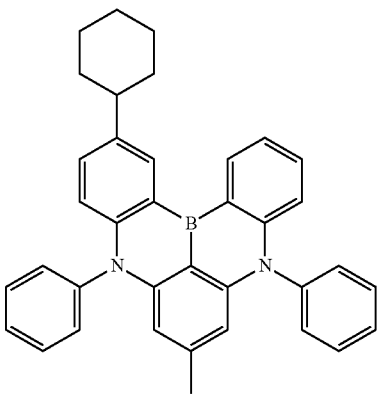

-continued
2-31
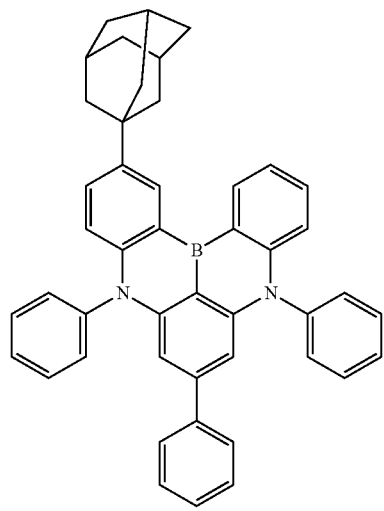
2-32
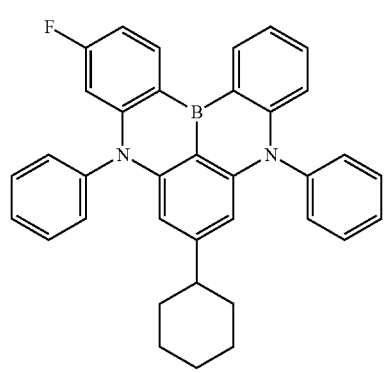
2-33
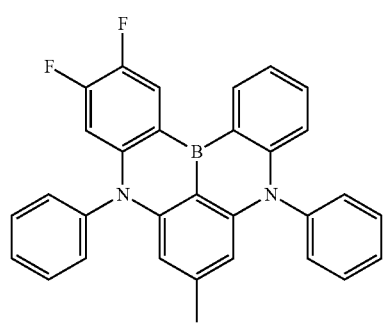
2-34
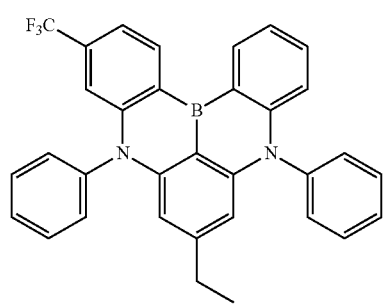
-continued
2-35
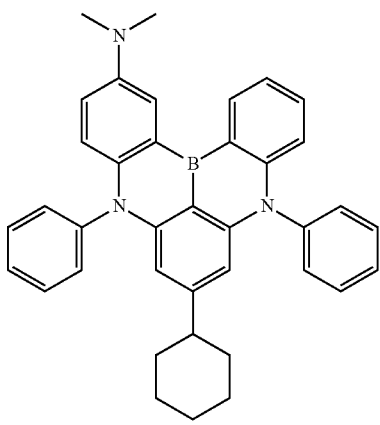
2-36
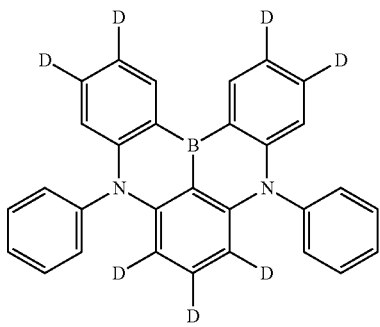
2-37
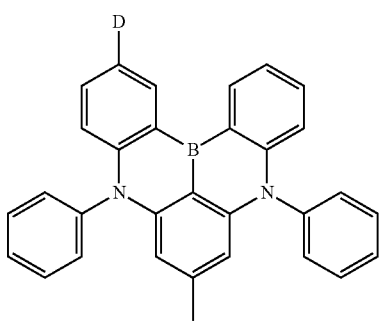
2-38
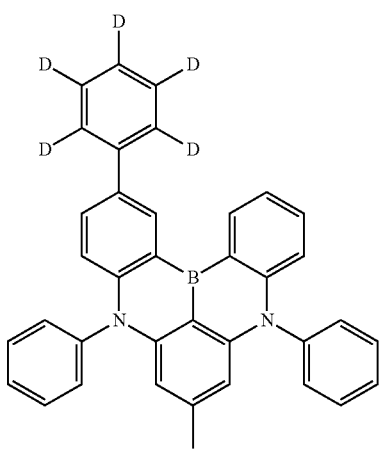

2-39
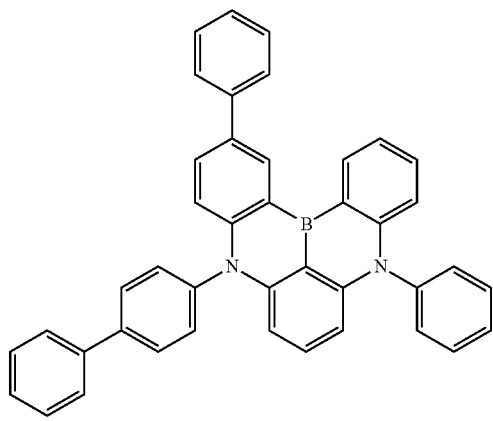
2-40
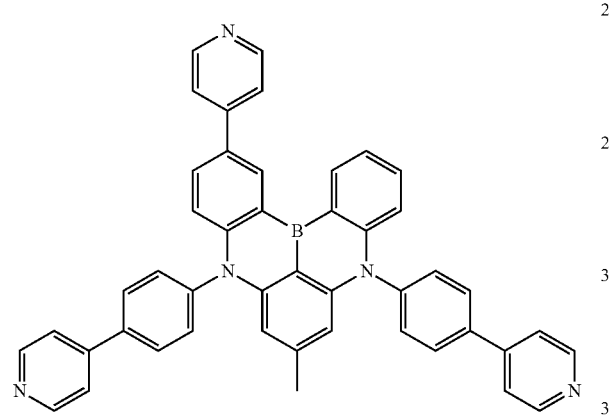
2-41
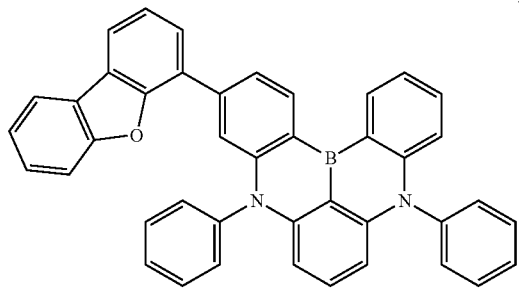
2-42
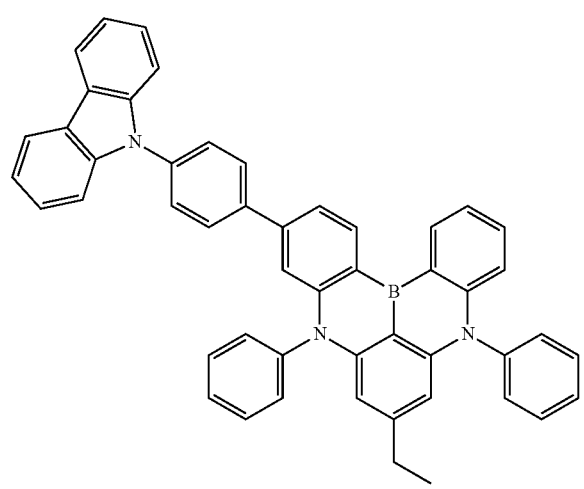
2-43
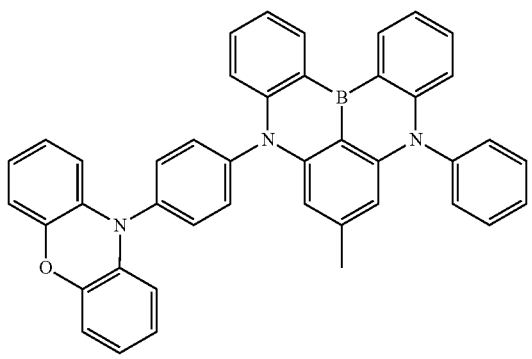
2-44
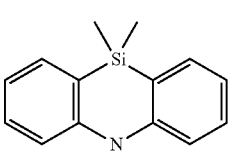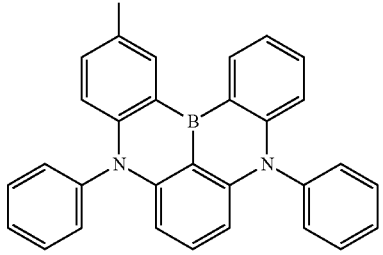
2-45
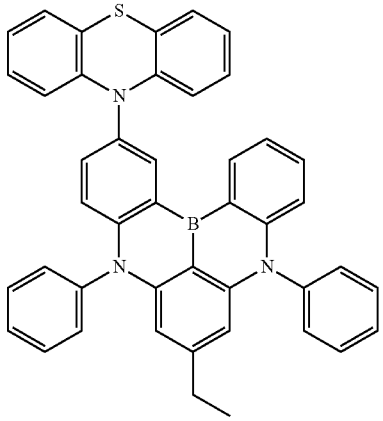
2-46
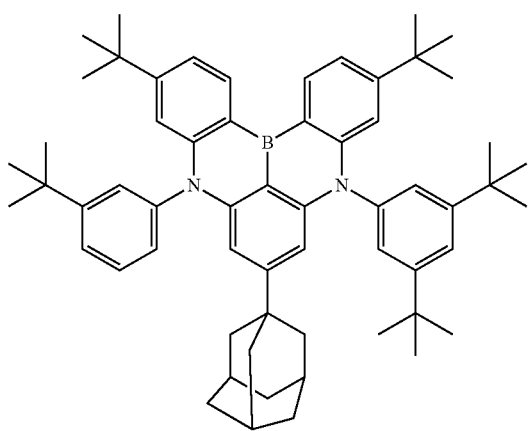

2-47
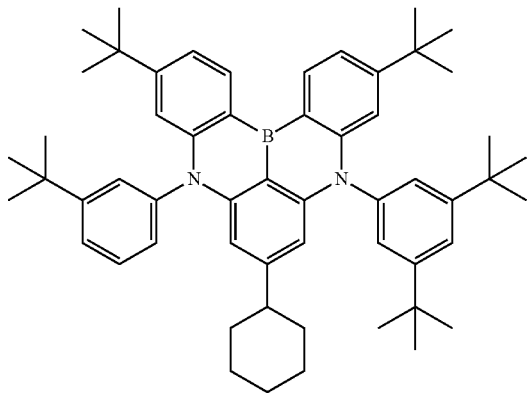
2-48
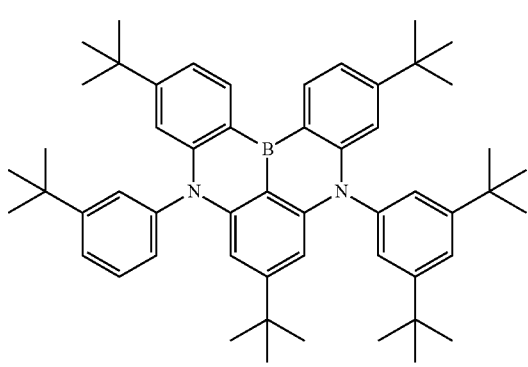
2-49
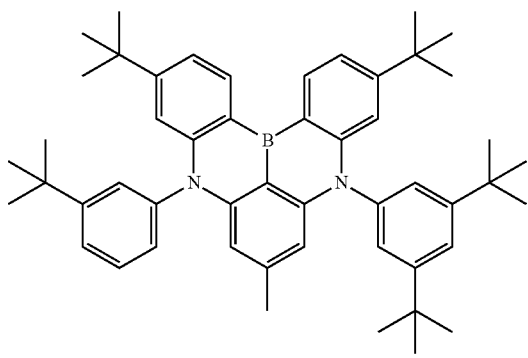
2-51
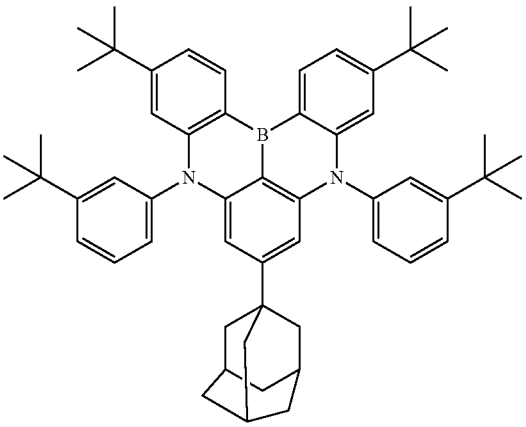
2-52
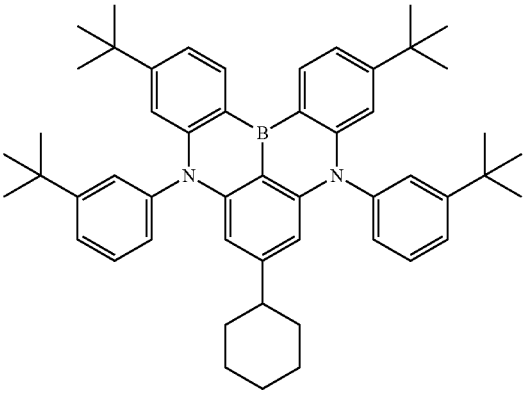
2-53
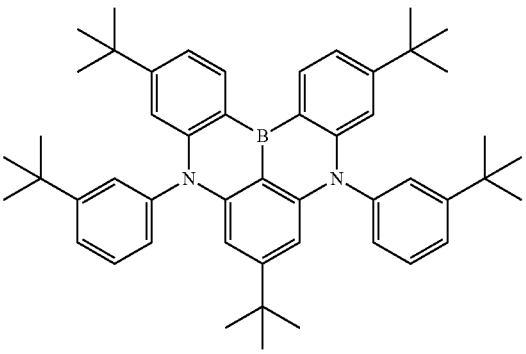
2-50

2-54
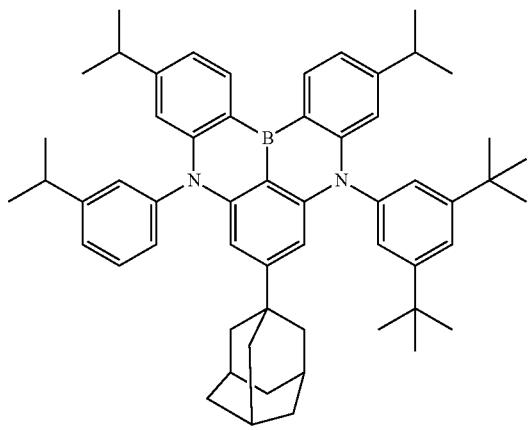
2-55
2-56
2-57
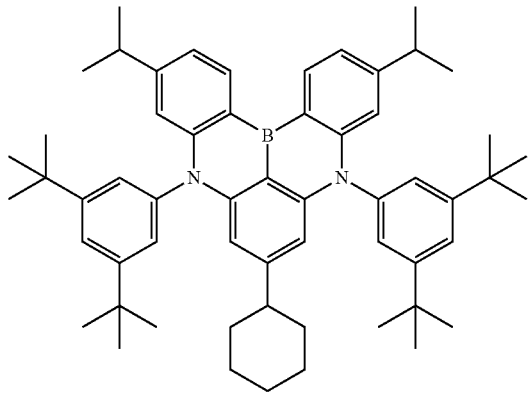
2-58
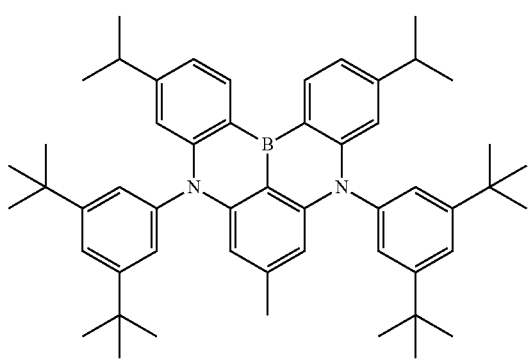
2-59
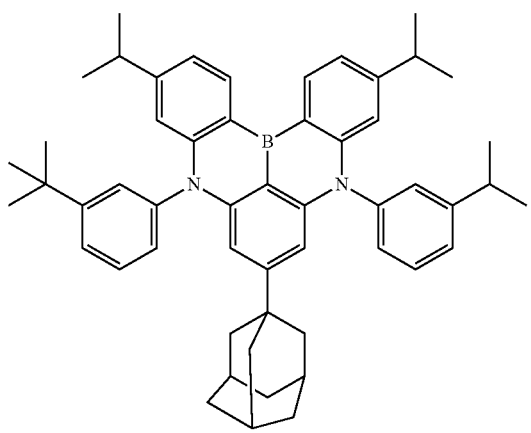
2-60
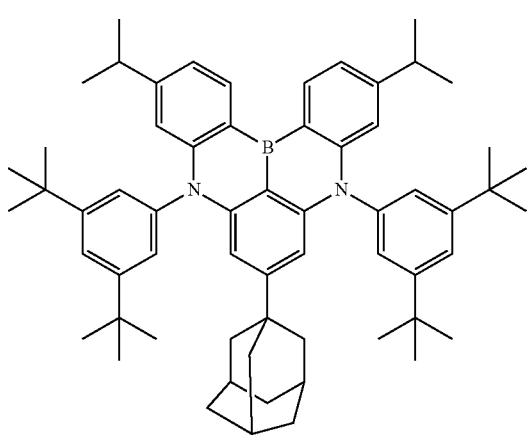

67
-continued
2-61
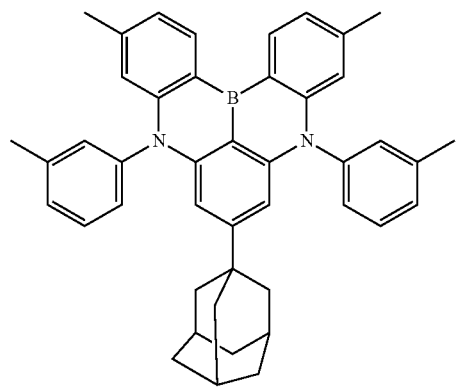
2-62
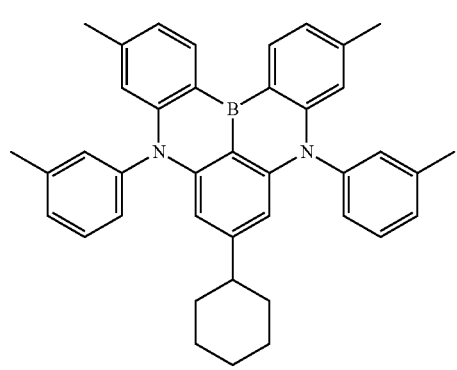
2-63
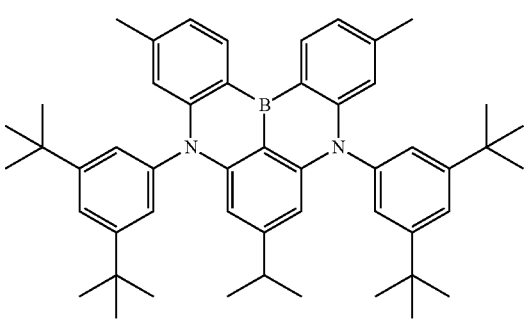
2-64
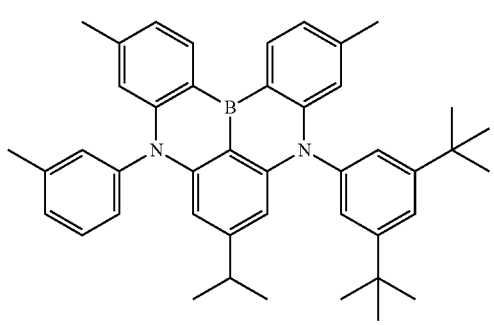
68
-continued
2-65
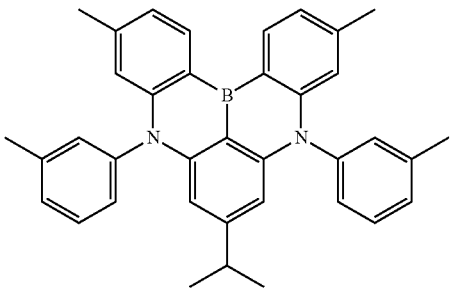
2-66
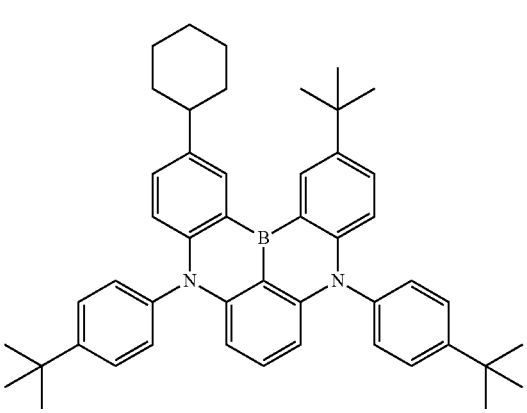
2-67
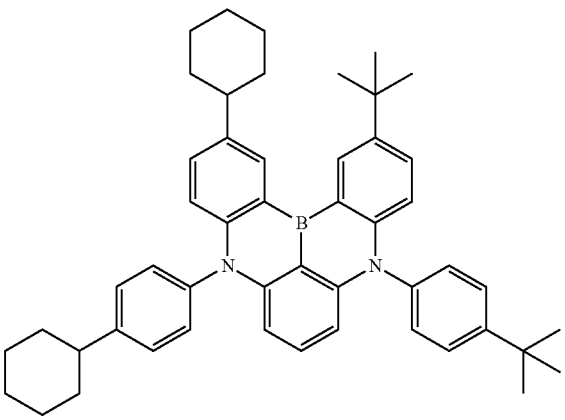
2-68
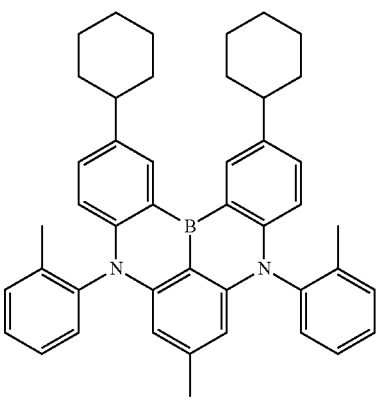

2-69
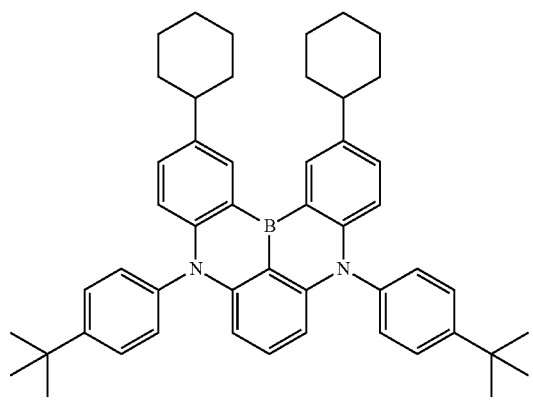
2-70
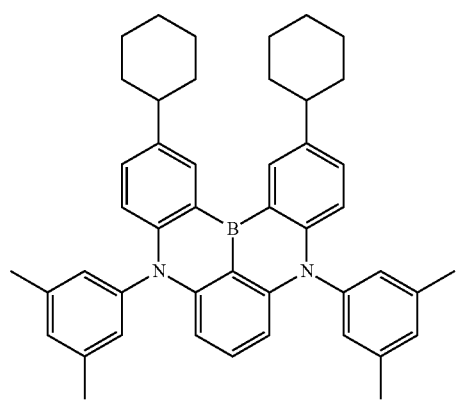
2-71
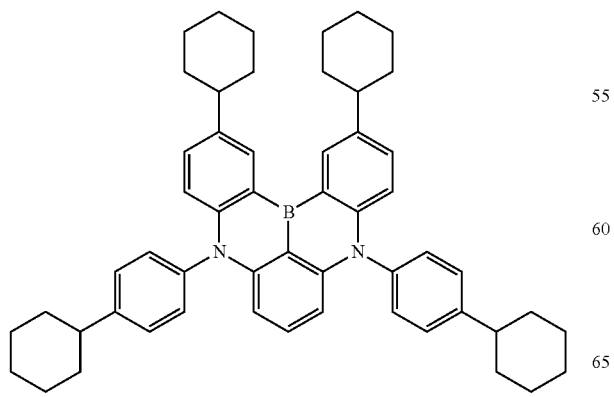
2-72
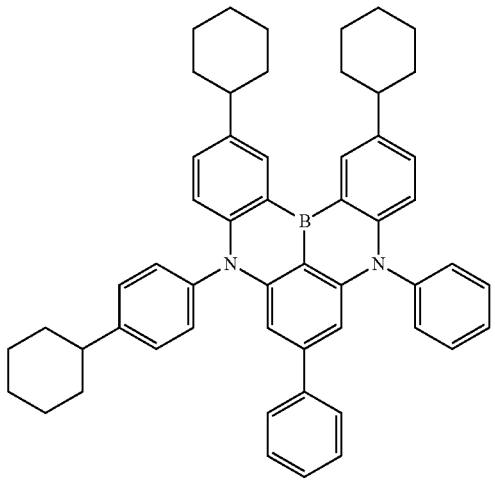
2-73
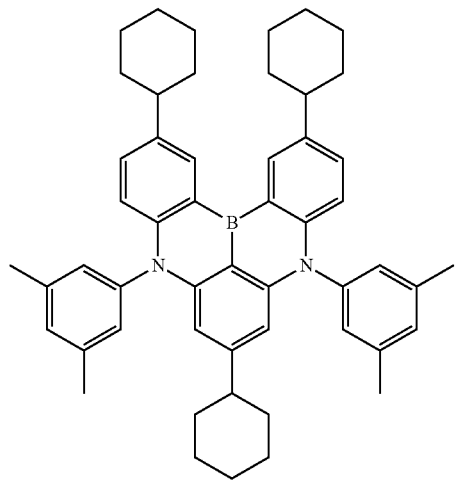
2-74
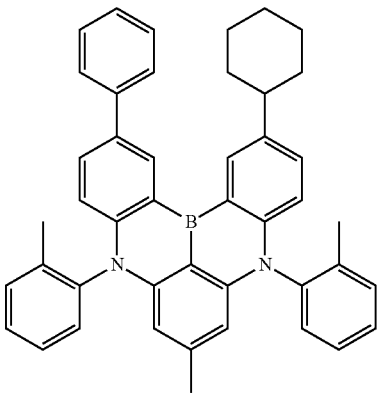

-continued
2-75
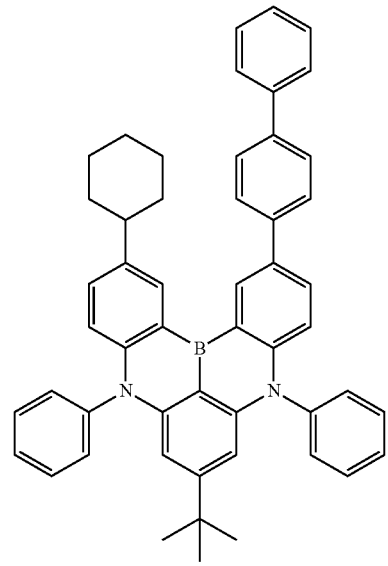
2-76
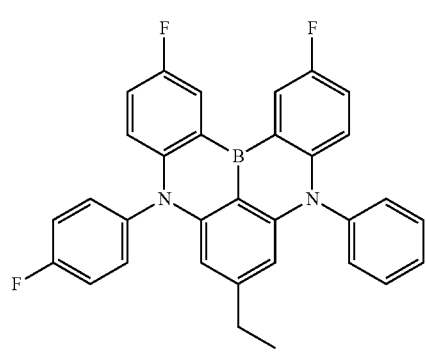
2-77
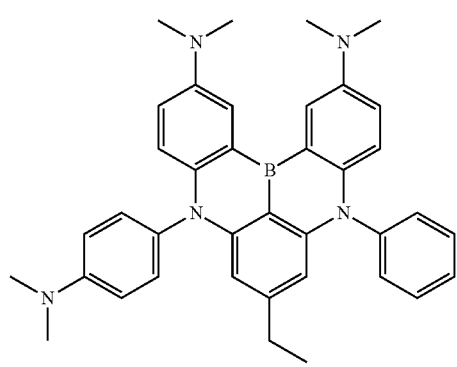
2-78
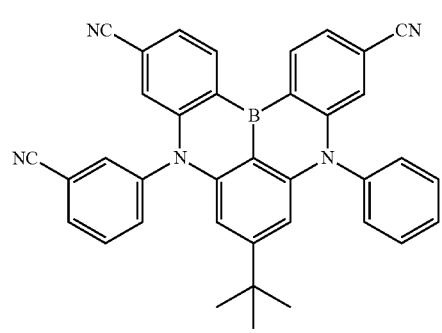
-continued
2-79
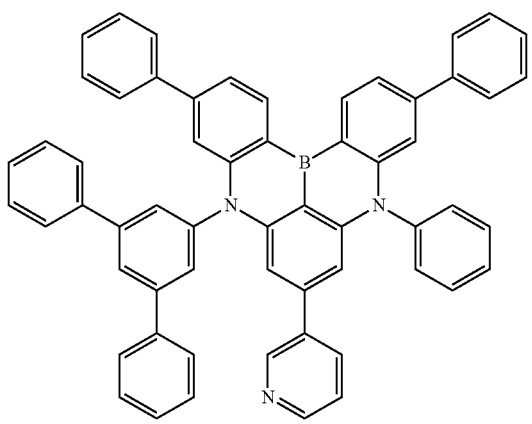
2-80
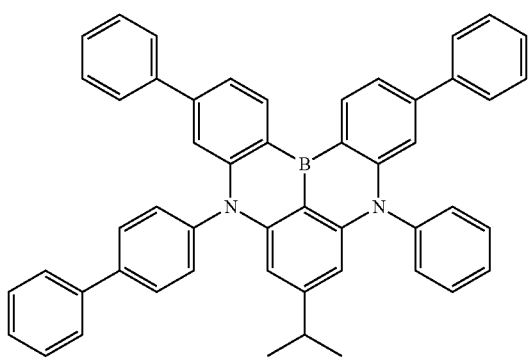
2-81
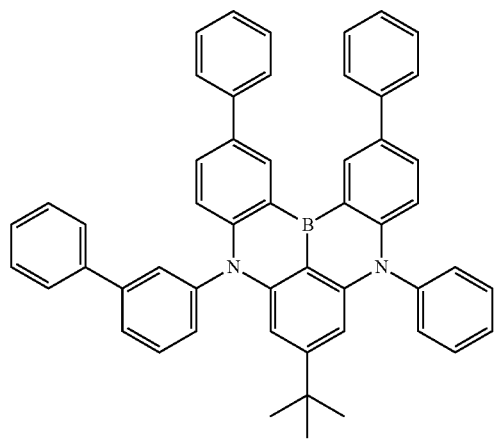

2-82
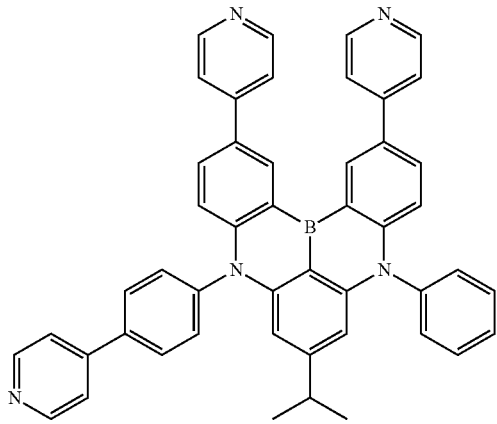

2-83
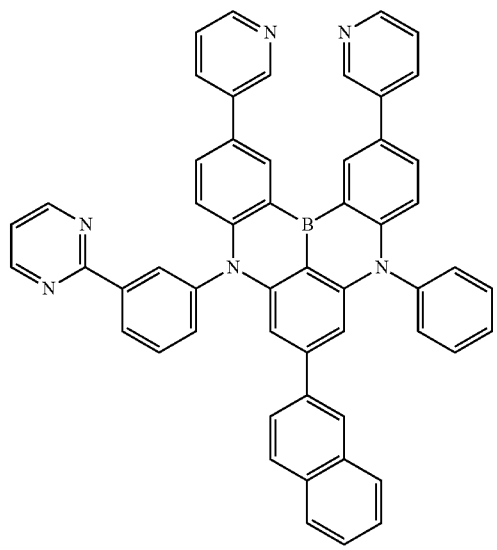

2-84
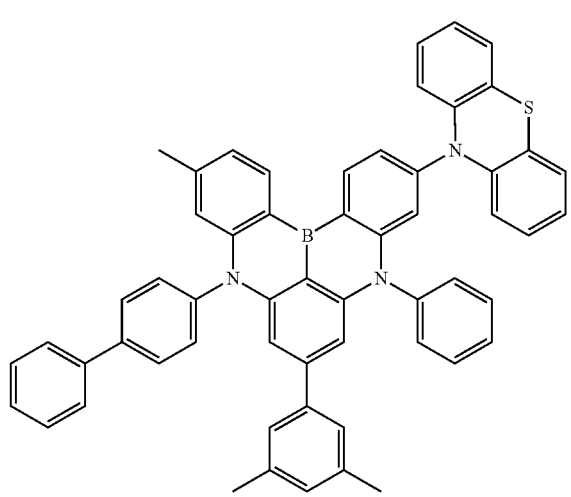

2-85
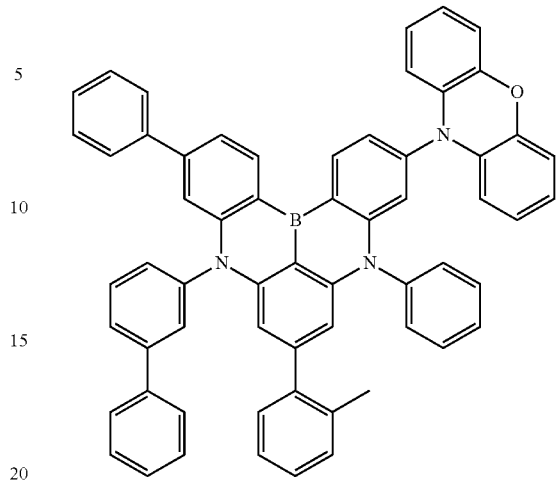

In one implementation, a content of each of the first dopant including the compound represented by Chemical Formula 1 and the second dopant including the compound represented by Chemical Formula 2 is preferably in a range of 0.01 to 20 wt %, more preferably, 0.5 to 10 wt %, based on a total weight of the organic light-emitting layer. When the content exceeds 20% by weight, a concentration of the dopants is too high such that the luminous efficiency may be lowered.

A ratio between weights of the first dopant and the second dopant is preferably in a range of 1:9 to 9:1, more preferably, in a range of 3:7 to 7:3.

The light-emitting layer may include a host in addition to the first dopant and the second dopant.

The light-emitting layer may emit blue (B) light.

The host material may be any host material known to be used in a blue light-emitting layer, such as anthracene and its derivatives, pyrene and its derivatives and perylene and its derivatives.

According to one preferred implementation of the present disclosure, there is provided an organic electroluminescent device comprising a first electrode; a second electrode facing away from the first electrode; and at least one organic layer interposed between the first electrode and the second electrode, wherein the at least one organic layer comprises one or more compounds of Chemical Formula 1 and one or more compounds of Chemical Formula 2.

Further, the organic layer according to the present disclosure defines one selected from a group consisting of a hole-injecting layer, a hole-transporting layer, an electron-blocking layer, a light-emitting layer, a hole-blocking layer, an electron-transporting layer and an electron-injecting layer.

Furthermore, the organic layer in accordance with the present disclosure defines a light-emitting layer, wherein the light-emitting layer comprises a compound of Chemical Formula 1 as a host material.

The organic electroluminescent device may include a vertical stack of an anode, a hole-injecting layer (HIL), a hole-transporting layer (HTL), a light-emitting layer (EML), an electron-transporting layer (ETL) and an electron-injecting layer (EIL) in this order. The device may further include an electron-blocking layer (EBL) and a hole-blocking layer (HBL) to enhance the light-emitting efficiency of the light-emitting layer, wherein the electron-blocking layer (EBL) and hole-blocking layer (HBL) sandwich the light-emitting layer (EML) therebetween.

Specifically, the organic electroluminescent device may further include an additional organic layer between the first electrode and the light-emitting layer or between the light-emitting layer and the second electrode, wherein the additional organic layer defines at least one selected from a group consisting of a hole-injecting layer, a hole-transporting layer, an electron-blocking layer, a light-emitting layer, a hole-blocking layer, an electron-transporting layer and an electron-injecting layer.

Further, when the device is embodied as a tandem organic electroluminescent device, a single light emission unit may be composed of a stack of at least two light emission layers and a charge generation layer (CGL) therebetween. The organic electroluminescent device may include two or more stacks on a substrate, wherein each stack includes a vertical stack of a first electrode and a second electrode facing away from each other, and a light-emitting layer disposed between the first and second electrodes to emit a specific light beam. The light-emitting layer coupled to a charge-generating layer (CGL) composed of an N-type charge-generating layer and a P-type charge-generating layer may render blue, yellow, green or red.

In one implementation of the present disclosure, there is provided an organic electroluminescent device comprising a first light emission sub-stack for rendering a first color and a second light emission sub-stack stacked on the first light emission sub-stack for rendering the second color. At least one of the first light emission sub-stack and the second light emission sub-stack comprises blue dopant material. The blue dopant material includes the compound represented by Chemical Formula 1 and the compound represented by Chemical Formula 2.

[Chemical Formula 1]

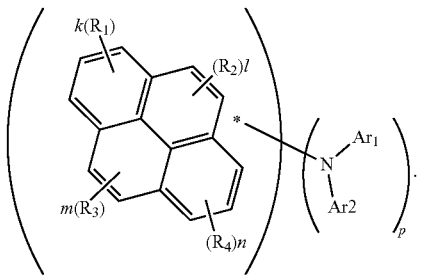

In Chemical Formula 1, $Ar_1$ and $Ar_2$ are the same or different from each other, and each of $Ar_1$ and $Ar_2$ independently represents one selected from a group consisting of a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 5 to 60 nuclear atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl group having 6 to 30 carbon atoms, and a substituted or unsubstituted aryloxy group having 6 to 30 carbon atoms, wherein each of $Ar_1$ and $Ar_2$ may be bonded to an adjacent group thereto to form a substituted or unsubstituted ring.

Each of $Ar_1$ and $Ar_2$ may be bonded to an adjacent group thereto, more specifically, be bonded to an adjacent group thereto, to form a substituted or unsubstituted ring having 5 to 12 nuclear atoms.

Each of $R_1$ to $R_4$ independently represents a substituent selected from a group consisting of deuterium, a cyano group, a nitro group, a halogen group, a hydroxyl group, a substituted or unsubstituted alkylthio group having 1 to 4 carbon atoms, a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 5 to 60 nuclear atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl groups having 6 to 30 carbon atoms, and a substituted or unsubstituted aryloxy groups having 6 to 30 carbon atoms, wherein each of $R_1$ to $R_4$ may be bonded to an adjacent group thereto to form a substituted or unsubstituted ring.

Each of $R_1$ to $R_4$ may be bonded to an adjacent group thereto, more specifically, be bonded to an adjacent group thereto, to form a substituted or unsubstituted ring having 5 to 12 nuclear atoms.

* indicates a site at which bonding occurs. The bonding to a framework of pyrene may occur.

The p is independently an integer of 1 to 4.

Each of k, l, m and n is independently an integer of 0 to 2.

[Chemical Formula 2]

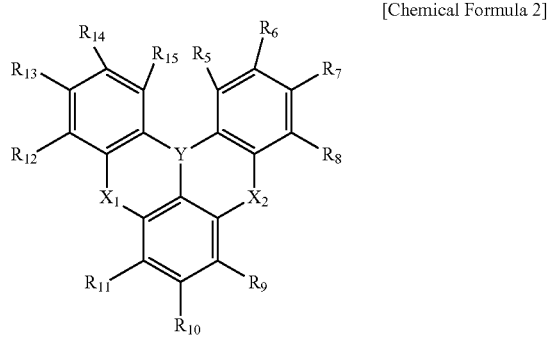

wherein in Chemical Formula 2, Y is B, N, P=O or P=S.

$X_1$ and $X_2$ are the same or different from each other, wherein each of $X_1$ and $X_2$ independently represents one selected from a group consisting of O, S, Se, $CR_{16}R_{17}$ and $NR_{18}$.

$R_5$ to $R_{18}$ are the same or different from each other, wherein each of $R_5$ to $R_{18}$ independently represents one selected from a group consisting of hydrogen, deuterium, a cyano group, a nitro group, a halogen group, a hydroxyl group, a substituted or unsubstituted alkylthio group having 1 to 4 carbon atoms, a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 5 to 60 nuclear atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl groups having 6 to 30 carbon atoms, and a substituted or unsubstituted aryloxy group having 6 to 30 carbon atoms, wherein each of $R_5$ to $R_{18}$ may be bonded to an adjacent group thereto to form a substituted or unsubstituted ring.

Each of $R_5$ to $R_{18}$ may be bonded to an adjacent group thereto, more specifically, be bonded to an adjacent group thereto, to form a substituted or unsubstituted ring having 5 to 12 nuclear atoms.

In Chemical Formula 1 and Chemical Formula 2, each of $R_1$ to $R_{18}$, $Ar_1$ and $Ar_2$ is independently substituted with at least one substituent selected from a group consisting of deuterium, a cyano group, a nitro group, a halogen group, a hydroxyl group, an alkyl group having 1 to 30 carbon atoms, a cycloalkyl group having 3 to 30 carbon atoms, an alkenyl group having 2 to 30 carbon atoms, an alkynyl group having 2 to 24 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having from 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms, and an aryloxy group having 6 to 30 carbon atoms, wherein when the at least one substituent includes a plurality of substituents, the plurality of substituents are the same or different from each other.

Details of the compound represented by Chemical Formula 1 and the compound represented by Chemical Formula 2 are the same as described above.

In one implementation, the first light emission sub-stack sequentially includes a first hole transport layer, a first light-emitting layer, and a first electron transport layer. The second light emission sub-stack sequentially includes a second hole transport layer, a second light-emitting layer and a second electron transport layer. At least one of the first light-emitting layer and the second light-emitting layer may include the blue dopant material.

FIG. 1 is a schematic cross-sectional view of a tandem organic electroluminescent device having two light emission sub-stacks according to an exemplary first embodiment of the present disclosure. As shown in FIG. 1, the organic electroluminescent device 100 according to the first embodiment of the present disclosure has a first electrode 110 and a second electrode 120 facing away from each other, and an organic light-emitting stack 130 positioned between the first electrode 110 and the second electrode 120. The organic light-emitting stack 130 comprises a first light emission sub-stack (ST1) 140 located between the first electrode 110 and the second electrode 120 and comprising a first light-emitting layer 144; a second light emission sub-stack (ST2) 150 located between the first light emission sub-stack 140 and the second electrode 120 and comprising a second light-emitting layer 154; and a charge-generating layer (CGL) 160 disposed between the first and second light emission sub-stacks 140 and 150.

The first electrode 110 acts as an anode for injecting holes. The first electrode 110 may be made of a conductive material with a high work function, for example, indium-tin-oxide (ITO), indium-zinc-oxide (IZO), and zinc-oxide (ZnO). The second electrode 120 acts as a cathode for injecting electrons. The second electrode 120 may be made of a conductive material having a low work function, for example, aluminum (Al), magnesium (Mg), and aluminum-magnesium alloy (AlMg).

The first light emission sub-stack 140 includes a vertical stack of a hole-injecting layer 141 located between the first electrode 110 and first light-emitting layer 144, a first hole-transporting layer 142 located between the hole-injecting layer 141 and the first light-emitting layer 144, and a first electron-transporting layer 146 located between first light-emitting layer 144 and charge-generating layer 160.

The hole-injecting layer 141 improves properties of an interface between the first electrode 110 as an inorganic layer and the first hole-transporting layer 142 as an organic layer. In one example, the hole-injecting layer 141 may comprise at least one selected from a group consisting of 4,4',4''-tris(3-methylphenylphenylamino)triphenylamine (MTDATA), copper phthalocyanine (CuPc), Tris(4-carbazoyl-9-yl-phenyl)amine (TCTA), N,N'-diphenyl-N,N'-bis(1-naphthyl)-1,1'-biphenyl-4,4''-diamine (NPB; NPD), 1,4,5,8,9,11-hexaazatriphenylenehexacarbonitrile (HATCN), 1,3,5-tris[4-(diphenylamino)phenyl]benzene (TDAPB), poly(3,4-ethylenedioxythiophene)polystyrene sulfonate (PEDOT/PSS), 2,3,5,6-tetrafluoro-7,7,8,8-tetracyanoquinodimethane (F4-TCNQ), and/or N-(biphenyl-4-yl)-9,9-dimethyl-N-(4-(9-phenyl-9H-carbazol-3-yl)phenyl)-9H-fluoren-2-amine.

In one example, a thickness of the hole-injecting layer 141 may be in a range of 1 to 150 nm. When the thickness of the hole-injecting layer 141 is greater than or equal to 1 nm, the hole injection characteristics may be improved. When the thickness is 150 nm or smaller, a problem of an increase in the driving voltage due to an increase in the thickness of the hole-injecting layer 141 may be prevented. The hole-injecting layer 141 may be omitted depending on a structure and properties of the organic electroluminescent device.

The first hole-transporting layer 142 is located between the hole-injecting layer 141 and the first light-emitting layer 144. The first light-emitting layer 144 is located between the first hole-transporting layer 142 and the first electron-transporting layer 146. The first electron-transporting layer 146 is located between the first light-emitting layer 144 and the charge-generating layer 160.

The second light emission sub-stack 150 includes a vertical stack of a second hole-transporting layer 152, a second light-emitting layer 154, a second electron-transporting layer 156, and an electron-injecting layer 158 in this order. The second hole-transporting layer 152 is located between the charge-generating layer 160 and the second light-emitting layer 154. The second light-emitting layer 154 is located between the second hole-transporting layer 152 and the second electrode 120. Further, the second electron-transporting layer 156 is located between the second light-emitting layer 154 and the second electrode 120. The electron-injecting layer 158 is located between the second electron-transporting layer 156 and the second electrode 120.

In one example, each of the first and second hole-transporting layers 142 and 152 may comprise at least one selected from a group consisting of N,N'-diphenyl-N,N'-bis(3-methylphenyl)-1,1'-biphenyl-4,4'-diamine (TPD), NPD, MTDATA, 1,3-bis(N-carbazolyl)benzene (mCP), CuPC, TCTA, tris(trifluorovinyl ether)-tris(4-carbazoyl-9-yl-phenyl)amine (TFV-TCTA), tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, tri-p-tolylamine, N-[1,1'-biphenyl]-4-yl-9,9-dimethyl-N-[4-(9-phenyl-9H-carbazol-3-yl)phenyl]-amine), 4,4'-bis(N-carbazolyl)-1,1'-biphenyl (CBP) and/or 1,1-bis(4-(N,N'-di(p-tolyl)amino)phenyl)cyclohexane (TAPC).

Each of the first hole-transporting layer 142 and the second hole-transporting layer 152 may have a thickness of 1 to 150 nm. In this connection, when the thickness of each of the first and second hole-transporting layers 142 and 152 is 1 nm or greater, the hole transporting property may be improved. When the thickness is 150 nm or smaller, the problem of the increase in a driving voltage due to an increase in the thickness of each of the first and second hole-transporting layers 142 and 152 may be prevented. The first hole-transporting layer 142 and the second hole-transporting layer 152 may be made of the same material or may be made of different materials.

In one exemplary embodiment, each of the first and second light-emitting layers 144 and 154 may comprise a host and dopants doped into the host. The first and second light-emitting layers 144, 154 may render different colors. The dopant material may be added in a content of about 1 to 30% by weight based on a weight of the host material.

In one example, one of the first light-emitting layer 144 and the second light-emitting layer 154 may render blue (B) and comprise a first dopant represented by Chemical Formula 1, and a second dopant represented by Chemical Formula 2.

The other of the first light-emitting layer 144 and the second light-emitting layer 154 may render blue (B), red (R), green (G), yellow (Y) or yellow-green (YG). In one exemplary embodiment, the first light-emitting layer 144 may render blue (B), while the second light-emitting layer 154 may render green (G), yellow-green (YG), yellow (Y) or orange (0) having a longer wavelength than blue.

In one example, one of the first light-emitting layer 144 and the second light-emitting layer 154 renders blue (B). In this case, one of the first light-emitting layer 144 and the second light-emitting layer 154 may comprise at least one fluorescent host material selected from a group consisting of anthracene and its derivatives, pyrene and its derivatives, and perylene and its derivatives, a first dopant represented by Chemical Formula 1, and a second dopant represented by Chemical Formula 2.

The blue light-emitting host material may include at least one selected from a group consisting of 4,4'-bis(2,2'-diphenylvinyl)-1,1'-biphenyl (DPVBi), 9,10-di-(2-naphtyl)anthracene (ADN), 2,5,8,11-(tetra-t-butylperylene (TBADN), 2-tert-butyl-9,10-di(2-naphthyl)anthracene, 2-methyl-9,10-di(2-naphtyl)anthracene (MADN), and/or 2,2',2"-(1,3,5-benzinetriyl)-tris(1-phenyl-1-H-benzimidazole (TBPi).

When the other of the first light-emitting layer 144 and the second light-emitting layer 154 may render green (G), the other of the first light-emitting layer 144 and the second light-emitting layer 154 may comprises a phosphorescent light-emitting material layer comprising a host such as CBP and an iridium-based dopant (for example, dp2Ir (acac), op2Ir (acac)). However, the present disclosure is not limited thereto. Alternatively, the green (G) light-emitting layer may comprise a fluorescent light-emitting material layer comprising tris(8-hydroxyquinolinato)aluminum (Alq). In this connection, the emission wavelength from the green (G) light-emitting layer may range from 510 nm to 570 nm.

Further, when the other of the first light-emitting layer 144 and the second light-emitting layer 154 is embodied as a red (R) light-emitting material layer, the other of the first light-emitting layer 144 and the second light-emitting layer 154 may include a phosphorescent light-emitting material layer comprising a host material such as CBP, and at least one dopant selected from a group consisting of bis(1-phenylisoquinoline)acetylacetonate iridium (PIQIr(acac)), bis((1-phenylquinoline)acetylacetonate iridium (PQIr(acac)), and octaethylporphyrin platinum (PtOEP). However, the present disclosure is not limited thereto.

Alternatively, the red (R) light-emitting layer may include a fluorescent light-emitting material layer that comprises 1,3,4-oxadiazole:Tris(dibenzoylmethane)mono(1,10-phentathroline)europium(III) (PBD:Eu(DBM)3(Phen)) or perylene and its derivatives. In this connection, the emission wavelength from the red (R) light-emitting layer may range from 600 nm to 650 nm.

Alternatively, when the other of the first light-emitting layer 144 and the second light-emitting layer 154 is embodied as a yellow (Y) light-emitting material layer, the other of the first light-emitting layer 144 and the second light-emitting layer 154 may be composed of a single yellow-green (YG) light-emitting material layer or a double layer of a yellow-green (YG) light-emitting material layer and green (G) light-emitting material layer. In one example, the yellow (Y) light-emitting material layer may comprise a host material selected from a group consisting of CBP, bis(2-methyl-8-quinolinolate)-4-(phenylphenolato)aluminium (B Alq), and a yellow-green phosphorescent dopant that emits yellow-green light. In this connection, the emission wavelength from the yellow (Y) light-emitting layer may range from 510 nm to 590 nm.

In an alternative embodiment, in order to improve the red emission efficiency of the organic electroluminescent device 100 having a tandem structure, each of the first light-emitting layer 144 and second light-emitting layer 145 may be embodied as a combination of two light-emitting material layers, for example, a combination of a yellow-green light-emitting material layer and a red light emission material layer, or a combination of a blue light-emitting material layer and a red light-emitting material layer.

In one example, when the other of the first light-emitting layer 144 and the second light-emitting layer 154 is embodied as a yellow-green (YG) light-emitting material layer, the other of the first light-emitting layer 144 and the second light-emitting layer 154 may be composed of a single yellow-green (YG) light-emitting material layer or a combination of a yellow-green light-emitting material layer and a green (G) light-emitting material layer. When the yellow-green (YG) light-emitting layer 154 is composed of a single layer structure of a yellow-green light-emitting material layer, the yellow-green light-emitting material layer may comprise a host material selected from a group consisting of CBP and BAlq, and a yellow-green phosphorescent dopant that emits yellow-green. However, the present disclosure is not limited thereto.

Alternatively, when the other of the first light-emitting layer 144 and the second light-emitting layer 154 is embodied as a yellow light-emitting material layer, the other of the first light-emitting layer 144 and the second light-emitting layer 154 may comprise a host material selected from a group consisting of CBP and BAlq, and a phosphorescent dopant that emits yellow. However, the present disclosure is not limited thereto.

In one example, the first electron-transporting layer 146 and the second electron-transporting layer 156 facilitate electrons transport in the first light emission sub-stack 140 and the second light emission sub-stack 150, respectively. Each of the first and second electron-transporting layers 146 and 156 may comprise one selected from a group consisting of oxadiazole, triazole, phenanthroline, benzoxazole, benzothiazole, benzimidazole, triazine and derivatives thereof.

In one example, each of the first and second electron-transporting layers 146 and 156 may comprise at least one selected from a group consisting of Alq3, 2-biphenyl-4-yl-5-(4-tbutylphenyl)-1,3,4-oxadiazole (PBD), spiro-PBD, lithiumquinolate (Liq), 2-[4-(9,10-Di-2-naphthalenyl-2-anthracenyl)phenyl]-1-phenyl-1Hbenzimidazol, 3-(biphenyl-4-yl)-5-(4-tertbutylphenyl)-4-phenyl-4H-1,2,4-triazole (TAZ), 4,7-diphenyl-1,10-phenanthroline (Bphen), tris(phenylquinoxaline) (TPQ), 1,3,5-Tri[(3-pyridyl)-phen-3-yl] benzene (TmPyPB) and/or 1,3,5-tris(N-phenylbenzimiazole-2-yl)benzene (TPBI).

Alternatively, each of the first and second electron-transporting layers 146 and 156 may be doped with an alkali metal or an alkaline earth metal compound. The metal components that may be employed as the dopants for each of the first and second electron-transporting layers 146 and 156 may include alkali metals such as lithium (Li), sodium (Na), potassium (K), and cesium (Cs), and/or alkaline earth metals such as magnesium (Mg), strontium (Sr), barium (Ba), and radium (Ra). However, the present disclosure is not limited thereto. The alkali metal or alkaline earth metal compound may be added in a ratio of approximately 1 to 20% by weight. The present disclosure is not limited thereto.

Each of the first and second electron-transporting layers 146 and 156 may have a thickness of 1 to 150 nm. When the thickness of each of the first and second electron-transporting layers 146 and 156 is 1 nm or greater, this may prevent the electrons transporting property from being degraded. When the thickness of each of the first and second electron-transporting layers 146 and 156 is 150 nm or smaller, this may prevent a driving voltage rise due to an increase in the thickness of each of the first and second electron-transporting layers 146 and 156. The first and second electron-transporting layers 146 and 156 may be of the same material or of different materials.

The electron-injecting layer 158 serves to facilitate the injection of the electrons. The electron-injecting layer 158 may comprise alkali halide-based materials such as LiF, NaF, KF, RbF, CsF, FrF, BeF$_2$, MgF$_2$, CaF$_2$, SrF$_2$, BaF$_2$ and RaF$_2$ and/or organic materials such as Liq (lithium quinolate), lithium benzoate, sodium stearate, Alq3, BAlq, PBD, spiro-PBD, and TAZ.

A thickness of the electron-injecting layer 158 may be in a range of 0.5 to 50 nm. When the electron-injecting layer 158 is 0.5 nm or larger thick, this may prevent electrons injection characteristics from being degraded. When the thickness of the electron-injecting layer 158 is 50 nm or smaller, this may prevent the driving voltage from rising due to an increase in the thickness of the electron-injecting layer 158.

According to an exemplary embodiment of the present disclosure, in the organic electroluminescent device 100 having a tandem structure, the charge-generating layer (CGL) 160 to increase current efficiency in each light-emitting layer and to distribute the charge smoothly may be disposed between the first light emission sub-stack 140 and the second light emission sub-stack 150. That is, the charge-generating layer 160 is located between the first light emission sub-stack 140 and the second light emission sub-stack 150, and the first light emission sub-stack 140 and the second light emission sub-stack 150 are connected with each other via the charge-generating layer 160. The charge-generating layer 160 may be embodied as a PN-junction charge-generating layer composed of a vertical stack of a N-type charge-generating layer 162 and the P-type charge-generating layer 164.

The N-type charge-generating layer 162 is located between the first electron-transporting layer 146 and the second hole-transporting layer 152. The P-type charge-generating layer 164 is located between the N-type charge-generating layer 162 and the second hole-transporting layer 152. The charge-generating layer 160 generates charges and divides charges into holes and electrons to provide electrons and holes to the first and second light emission sub-stacks 140 and 150 respectively.

That is, the N-type charge-generating layer 162 supplies electrons to the first electron-transporting layer 146 of the first light emission sub-stack 140. Then, the first electron-transporting layer 146 supplies electrons to the first light-emitting layer 144 adjacent the first electrode 110. Meanwhile, the P-type charge-generating layer 164 supplies holes to the second hole-transporting layer 152 of the second light emission sub-stack 150. Then, the second hole-transporting layer 152 supplies holes to the second light-emitting layer 154 adjacent to the second electrode 120.

In this connection, the P-type charge-generating layer 164 may be made of a metal or an organic host material doped with a P-type dopant. In this connection, the metal may include one selected from a group consisting of Al, Cu, Fe, Pb, Zn, Au, Pt, W, In, Mo, Ni and Ti and alloys of at least two thereof. Further, the P-type dopant and the host material may employ materials known well to the skilled person to the art. In one example, the P-type dopant may include one selected from a group consisting of F4-TCNQ, iodine, FeCl$_3$, FeF$_3$ and SbCl$_5$. Further, the host material may include at least one selected from a group consisting of NPB, TPD, N,N,N',N'-tetranaphthalenyl-benzidine (TNB) and HAT-CN.

Alternatively, the N-type charge-generating layer 162 may comprise, as a dopant, a metal compound such as an alkali metal or alkaline earth metal compound. The alkali metal or alkaline earth metal may be added at a ratio of about 1 to 30% by weight based on a weight of the organic compound according to the present disclosure. However, the present disclosure is not limited thereto.

The N-type charge-generating layer 162 may be doped with an alkali metal or alkaline earth metal compound to improve electrons injection ability into the first electron-transporting layer 146. Specifically, when an alkali metal or an alkaline earth metal is used as a dopant for the N-type charge-generating layer 162, the alkali metal or an alkaline earth metal used as the dopant bonds with the organic compound in accordance with the present disclosure to form a gap state. Thus, a difference between energy levels of the N-type charge-generating layer 162 and the P-type charge-generating layer 164 is reduced, and, thus, electrons injection ability from the N-type charge-generating layer 162 to the first electron-transporting layer 146 is improved.

Figure 2:
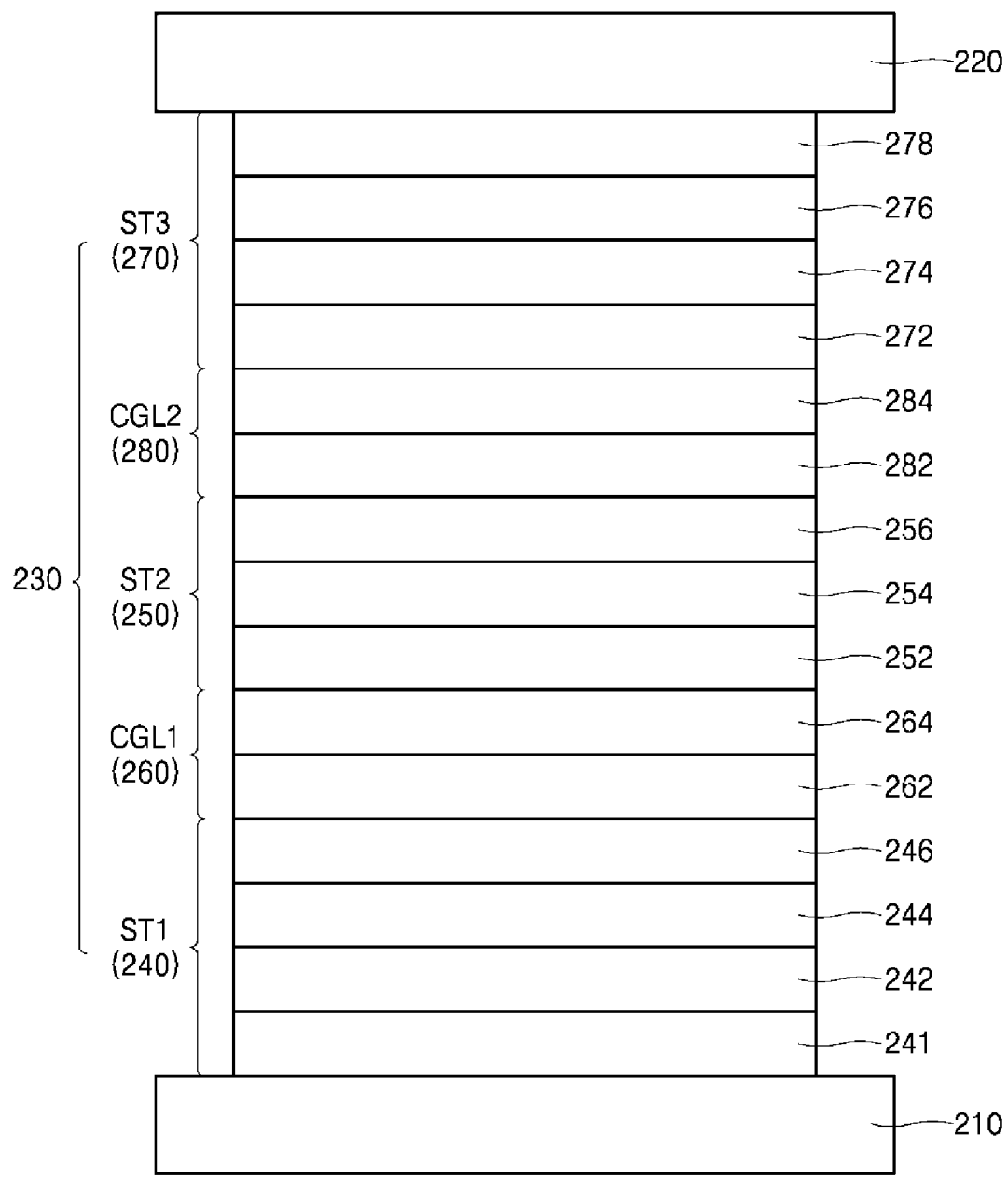
FIG. 2 shows a schematic cross-sectional view of an organic electroluminescent device having a tandem structure having three light emission sub-stacks and comprising a compound represented by Chemical Formula 1 according to another embodiment of the present disclosure.

In FIG. 2, the organic electroluminescent device 200 includes a first electrode 210 and a second electrode 220 facing away from each other, and an organic light-emitting layer 230 positioned between the first electrode 210 and the second electrode 220. The organic light-emitting layer 230 may include a vertical stack of a first light emission sub-stack (ST1) 240, a second light emission sub-stack (ST2) 250, a third light emission sub-stack (ST3) 270, a first charge-generating layer (CGL1) 260, and a second charge-generating layer (CGL2) 280. Alternatively, at least four light emission sub-stacks and at least three charge-generating layers may be disposed between the first and second electrodes 210 and 220.

As described above, the first electrode 210 may act as an anode for injecting holes, and may be made of any one of a conductive material having a high work function, for example, ITO, IZO, or ZnO. The second electrode 220 may act as a cathode for injecting electrons and may be made of any conductive material having a low work function, for example, aluminum (Al), magnesium (Mg), or aluminum-magnesium alloy (AlMg).

The first and second charge-generating layers 260 and 280 are located between the first and second light emission sub-stacks 240 and 250 and between the second and third light emission sub-stacks 250 and 270, respectively. The first light emission sub-stack 240, first charge-generating layer 260, second light emission sub-stack 250, second charge-generating layer 280 and third light emission sub-stack 270 are sequentially stacked on the first electrode 210. That is, the first light emission sub-stack 240 is positioned between the first electrode 210 and the first charge-generating layer 260. The second light emission sub-stack 250 is positioned between the first charge-generating layer 260 and the second charge-generating layer 280. The third light emission sub-stack 270 is located between the second electrode 220 and the second charge-generating layer 280.

The first light emission sub-stack 240 may include a vertical stack of the hole-injecting layer 241, the first hole-transporting layer 242, the first light-emitting layer 244, and the first electron-transporting layer 246 on the first electrode 210. In this connection, the hole-injecting layer 241 and the first hole-transporting layer 242 are located between the first electrode 210 and the first light-emitting layer 244. The hole-injecting layer 241 is located between the first electrode 210 and the first hole-transporting layer 242. Further, the first electron-transporting layer 246 is located between the first light-emitting layer 244 and the first charge-generating layer 260.

The hole-injecting layer 241, the first hole-transporting layer 242, the first light-emitting layer 244, and the first electron-transporting layer 246 may be respectively identical with the hole-injecting layer 141, the first hole-transporting layer 142, the first light-emitting layer 144 and the first electron-transporting layer 146. Thus, a description thereof will be omitted. For example, the first light-emitting layer 244 may be embodied as a blue (B) light-emitting material layer. In this connection, the emission wavelength from the first light emission sub-stack 240 may range from 440 nm to 480 nm.

The second light emission sub-stack 250 may include a vertical stack of the second hole-transporting layer 252, the second light-emitting layer 254, and the second electron-transporting layer 256. The second hole-transporting layer 252 is located between the first charge-generating layer 260 and the second light-emitting layer 254. The second electron-transporting layer 256 is located between the second light-emitting layer 254 and the second charge-generating layer 280.

The second hole-transporting layer 252, the second light-emitting layer 254 and the second electron-transporting layer 256 may be respectively identical with the second hole-transporting layer 152, the second light-emitting layer 154 and the second electron-transporting layer 156. Thus, a description thereof will be omitted. For example, the second light-emitting layer 254 may be embodied as a yellow-green (YG) or yellow (Y) light-emitting material layer. In this connection, the emission wavelength from the second light emission sub-stack 250 may range from 510 nm to 590 nm or range from 460 nm to 510 nm.

The third light emission sub-stack 270 may include a vertical stack of a third hole-transporting layer 272, a third light-emitting layer 274, a third electron-transporting layer 276, and an electron-injecting layer 278. The third hole-transporting layer 272 is located between the second charge-generating layer 280 and the third light-emitting layer 274. The third electron-transporting layer 276 is located between the third light-emitting layer 274 and the second electrode 220. The electron-injecting layer 278 is located between the third electron-transporting layer 276 and the second electrode 220.

The third hole-transporting layer 272, the third electron-transporting layer 276, and the electron-injecting layer 278 may be respectively identical with the second hole-transporting layer 152, the second electron-transporting layer 156, and the electron-injecting layer 158. Thus, a description thereof will be omitted. The third light-emitting layer 274 may be identical with the first light-emitting layer 144 or the second light-emitting layer 154. For example, the third light-emitting layer 274 may be embodied as a blue (B) light-emitting material layer. In this connection, the emission wavelength from the third light emission sub-stack 270 may range from 440 nm to 480 nm. In another alternative embodiment, the third light-emitting layer 274 may be embodied as a yellow-green (YG) or yellow (Y) light-emitting material layer. In this case, the emission wavelength from the third light emission sub-stack 270 may range from 460 nm to 590 nm.

In one implementation according to the present disclosure, at least one of the first light-emitting layer, the second light-emitting layer and the third light-emitting layer comprises blue dopants comprising the compound having chemical formula 1 as described above and the compound having chemical formula 2 as described above.

The first charge-generating layer 260 is located between the first light emission sub-stack 240 and the second light emission sub-stack 250. The second charge-generating layer 280 is located between the second light emission sub-stack 250 and the third light emission sub-stack 270. Each of the first and second charge-generating layers 260 and 280 may embodied as a PN-junction charge-generating layer composed of a vertical stack of each of the N-type charge-generating layers 262 and 282 and each of the P-type charge-generating layers 264 and 284.

In the first charge-generating layer 260, the N-type charge-generating layer 262 is located between the first electron-transporting layer 246 and the second hole-transporting layer 252. The P-type charge-generating layer 264 is located between the N-type charge-generating layer 262 and the second hole-transporting layer 252.

Further, in the second charge-generating layer 280, the N-type charge-generating layer 282 is located between the second electron-transporting layer 256 and the third hole-transporting layer 272. The P-type charge-generating layer 284 is located between the N-type charge-generating layer 282 and the third hole-transporting layer 272.

Each of the first and second charge-generating layers 260 and 280 generates charges and/or divides the charges into electrons and holes to supply the electrons and holes into each of the first to third light emission sub-stacks 240, 250 and 270.

That is, in the first charge-generating layer 260, the N-type charge-generating layer 262 supplies electrons to the first electron-transporting layer 246 of the first light emission sub-stack 240. The P-type charge-generating layer 264 supplies holes to the second hole-transporting layer 252 of the second light emission sub-stack 250.

Further, in the second charge-generating layer 280, the N-type charge-generating layer 282 supplies electrons to the second electron-transporting layer 256 of the second light emission sub-stack 250. The P-type charge-generating layer 284 supplies holes to the third hole-transporting layer 272 of the third light emission sub-stack 270.

In this connection, each of the P-type charge-generating layers 264 and 284 may be made of a metal or an organic host material doped with a P-type dopant. In this connection, the metal may include one or more selected from a group consisting of Al, Cu, Fe, Pb, Zn, Au, Pt, W, In, Mo, Ni, Ti and alloys of at least two thereof. Further, the P-type dopant and the host material may include materials conventionally employed by the skilled person to the art. For example, the P-type dopant may include a material selected from a group consisting of F4-TCNQ, iodine, $FeCl_3$, $FeF_3$ and $SbCl_5$. Further, the host material may include at least one material selected from the group consisting of NPB, TPD, TNB and HAT-CN.

Alternatively, each of the N-type charge-generating layer 262, 282 may comprise, as a dopant, a metal compound including an alkali metal or alkaline earth metal.

For example, each of the N-type charge-generating layers 262 and 282 may comprise at least one material selected from a group consisting of LiQ, LiF, NaF, KF, RbF, CsF, FrF, $BeF_2$, $MgF_2$, $CaF_2$, $SrF_2$, $BaF_2$ and $RaF_2$ in addition to the organic compound according to the present disclosure. However, the present disclosure is not limited thereto.

The n-type charge-generating layers 262 and 282 may be doped with an alkali metal or an alkaline earth metal compound to improve electrons injection ability into the electron-transporting layers 246 and 256.

The organic electroluminescent device according to the present disclosure may be applied to an organic light emitting display device and an illumination device using an organic electroluminescent device. In one example, FIG. 3 is a schematic cross-sectional view of an organic light emission display device according to an exemplary embodiment of the present disclosure.

Figure 3:
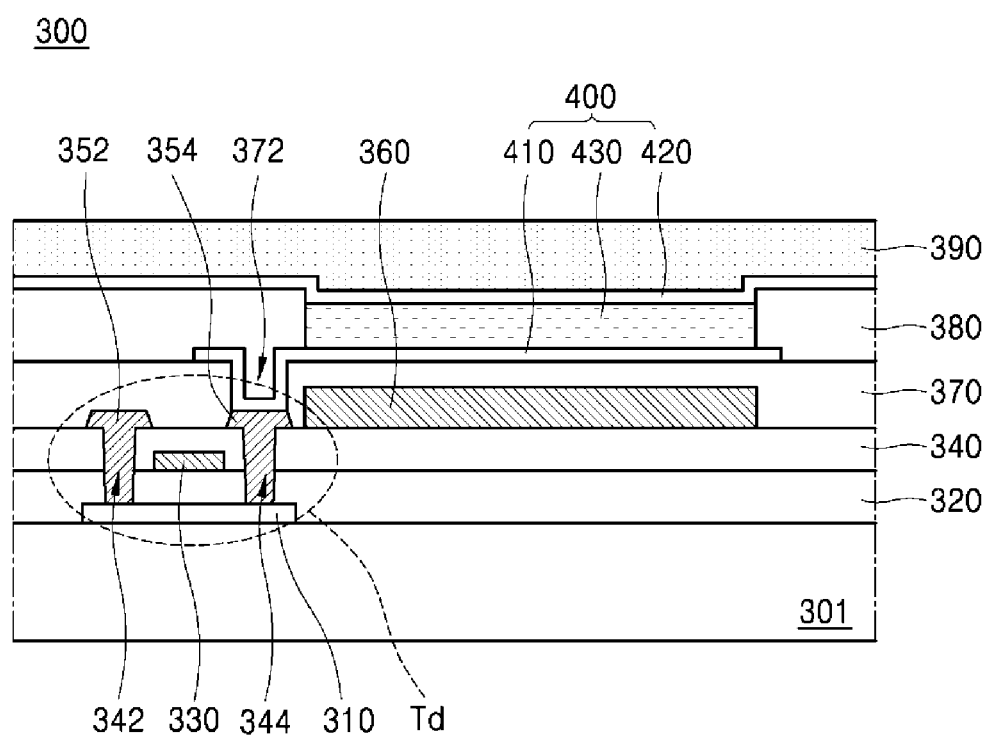
FIG. 3 is a cross-sectional view schematically showing an organic light emission display device having an organic electroluminescent device according to still another embodiment of the present disclosure.

As shown in FIG. 3, the organic light emission display device 300 may comprise a substrate 301, an organic electroluminescent device 400, and an encapsulation film 390 covering the organic electroluminescent device 400. On the substrate 301, a driving thin-film transistor Td as a driving element and an organic electroluminescent device 400 connected to the driving thin-film transistor Td are disposed.

Although not shown, the following components may be disposed on the substrate 301: a gate line and a data line defining a pixel region and intersecting each other; a power line extending parallel to and spaced from either the gate line or the data line; a switching thin-film transistor connected to the gate line and data line; and a storage (capacitor) connected to one electrode of the switching thin-film transistor and the power line.

The driving thin-film transistor Td is connected to the switching thin-film transistor. The driving thin-film transistor Td includes a semiconductor layer 310, a gate electrode 330, a source electrode 352, and a drain electrode 354.

The semiconductor layer 310 is formed on the substrate 301 and is made of an oxide semiconductor or polycrystalline silicon. When the semiconductor layer 310 is made of an oxide semiconductor material, a screening pattern (not shown) may not be formed beneath the semiconductor layer 310. The screening pattern prevents light from entering the semiconductor layer 310, thereby preventing the semiconductor layer 301 from being deteriorated by light. Alternatively, the semiconductor layer 310 may be made of polycrystalline silicon. In this case, impurities may be doped into both edges of the semiconductor layer 310.

On the semiconductor layer 310, a gate insulating film 320 made of an insulating material may be formed over an entire surface of the substrate 301. The gate insulating film 320 may be made of an inorganic insulating material such as silicon oxide or silicon nitride.

On the gate insulating film 320, the gate electrode 330 made of a conductive material such as metal is formed in a center region of the semiconductor layer 310. The gate electrode 330 is connected to a switching thin-film transistor.

On the gate electrode 330, an inter-layer insulating film 340 made of an insulating material is formed over the entire surface of the substrate 301. The inter-layer insulating film 340 may be made of an inorganic insulating material such as silicon oxide or silicon nitride, or an organic insulating material such as benzocyclobutene or photo-acryl.

The inter-layer insulating film 340 has contact holes 342 and 344 exposing both lateral portions of the semiconductor layer 310. The contact holes 342 and 344 are spaced apart from the gate electrode 330 and disposed on both sides of the gate electrode 330 respectively.

On the inter-layer insulating film 340, the source electrode 352 and drain electrode 354 made of a conductive material such as a metal are disposed. The source electrode 352 and drain electrode 354 are disposed about the gate electrode 330 and are spaced from each other. The source electrode 352 and drain electrode 354 contacts both sides of the semiconductor layer 310 via the contact holes 342 and 344, respectively. The source electrode 352 is connected to a power line (not shown).

The semiconductor layer 310, the gate electrode 330, the source electrode 352, and the drain electrode 354 define the driving thin-film transistor Td. The driving thin-film transistor Td has a coplanar structure in which the gate electrode 330, the source electrode 352, and the drain electrode 354 are disposed in a coplanar manner on the semiconductor layer 310.

Alternatively, the driving thin-film transistor Td may have an inverted staggered structure in which the gate electrode is located below the semiconductor layer, and the source electrode and the drain electrode are located above the semiconductor layer. In this case, the semiconductor layer may be made of amorphous silicon. In one example, the switching thin-film transistor (not shown) may have substantially the same structure as the driving thin-film transistor Td.

In one example, the organic light emission display device 300 may include a color filter 360 that absorbs light generated from the organic electroluminescent device 400. For example, the color filter 360 may absorb red (R), green (G), blue (B), and white (W) light. In this case, color filter patterns that absorb the red, green and blue light may be disposed separately on a pixel basis. Each of these color filter patterns may overlap with a corresponding organic light-emitting layer 430 of the organic electroluminescent device 400 that emits light having a corresponding wavelength. Adopting the color filter 360 may allow the organic light emission display device 300 to render a full color range.

For example, when the organic light emission display device 300 is of a bottom light emission type, the color filter 360, which absorbs light, may be located above the interlayer insulating film 340 in a region of the organic electroluminescent device 400. In an alternative embodiment, when the organic light emission display device 300 is of a top light emission type, the color filter may be located on top of the organic electroluminescent device 400, i.e., on top of the second electrode 420. In one example, the color filter 360 may have a thickness of 2 to 5 µm. In this connection, the organic electroluminescent device 400 may be embodied as an organic electroluminescent device having a tandem structure as shown in FIG. 1 and FIG. 2.

In one example, a protective layer 370 having a drain contact hole 372 exposing the drain electrode 354 of the driving thin-film transistor Td may be formed to cover the driving thin-film transistor Td.

On the protective layer 370, the first electrode 410 connected to the drain electrode 354 of the driving thin-film transistor Td via the drain contact hole 372 may be formed on a pixel region basis.

The first electrode 410 may act as an anode and may be made of a conductive material having a relatively higher work function value. For example, the first electrode 410 may be made of a transparent conductive material such as ITO, IZO or ZnO.

In one example, when the organic light emitting display device 300 is of a top light emission type, a reflective electrode or a reflective layer may be further formed below the first electrode 410. For example, the reflective electrode or reflective layer may be made of any one of aluminum (Al), silver (Ag), nickel (Ni), and aluminum-palladium-copper (APC alloy).

On the protective layer 370, a bank layer 380 covering an edge of the first electrode 410 is formed. The bank layer 380 exposes a center region of the first electrode 410 corresponding to the pixel region.

An organic light-emitting layer 430 is formed on the first electrode 410. In one example, the organic light-emitting layer 430 may have at least two light emission sub-stacks shown in FIG. 1 and FIG. 2. Accordingly, the organic electroluminescent device 400 may have a tandem structure.

A second electrode 420 is formed on the organic light-emitting layer 430. The second electrode 420 may be disposed over an entire display region and may be made of a conductive material having a relatively lower work function value and may act as a cathode. For example, the second electrode 420 may be made of any one of aluminum (Al), magnesium (Mg), and aluminum-magnesium alloy (AlMg).

The first electrode 410, the organic light-emitting layer 430 and the second electrode 420 together define the organic electroluminescent device 400.

On the second electrode 420, the encapsulation film 390 is formed to prevent external moisture from penetrating into the organic electroluminescent device 400. Although not shown, the encapsulation film 390 may have a triple layer structure in which a first inorganic layer and an organic layer and a second inorganic layer are sequentially stacked. However, the present invention is not limited thereto.

Examples of the present disclosure are provided to more fully describe the present disclosure to those skilled in the art. The Examples may be modified into several different forms. The scope of the present disclosure is not limited to the following Examples. Rather, these Examples are intended to make the present disclosure more complete and are provided to fully convey the ideal of the present disclosure to those skilled in the art.

First, hereinafter, methods for synthesizing the compounds represented by Chemical Formulas 1 and 2 will be described below as a representative example.

However, the methods for synthesizing the compounds in accordance with the present disclosure is not limited to following exemplified methods. The compounds in accordance with the present disclosure may be prepared by methods illustrated below and methods known in the art.

Synthesis Example 1

Compound 1-5 Synthesis

[Reaction Formula 1]

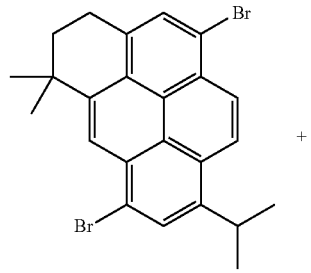

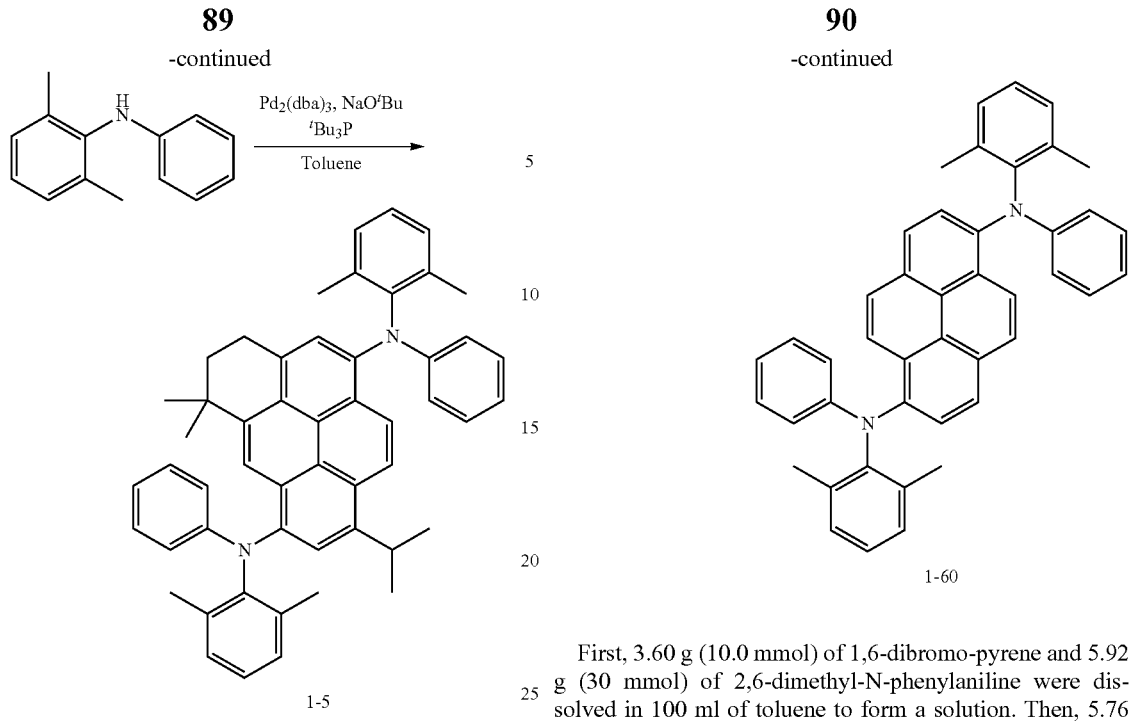

1-5

First, 4.70 g (10.0 mmol) of 1,7-dibromo-9-isopropyl-5,5-dimethyl-4,5-dihydro-3H-benzo[cd]pyrene and 8.02 g (30 mmol) of 2,6-dimethyl-N-phenylaniline were dissolved in 100 ml of toluene to form a solution. Then, 5.76 g (60.0 mmol) of t-BuONa, 0.46 g (0.5 mmol) of Pd$_2$(dba)$_3$ and 0.2 g (1.0 mmol) of t-Bu$_3$P were added to the solution which, in turn, was stirred for 6 hours under heating/reflux. After completion of the reaction, 100 ml of water was added thereto, and a toluene layer was extracted therefrom. Then, 50 ml of water was added thereto and then a further toluene layer was extracted therefrom. The extracted solution was treated with MgSO$_4$ to remove residual water and then was concentrated. Then, the concentrated solution was then column-purified with n-hexane/methylene chloride (MC), thereby to yield 3.23 g of the compound 1-5 at 46% yield.

MS (MALDI-TOF) m/z: 702 [M]+

Synthesis Example 2

Compound 1-60 Synthesis

[Reaction Formula 2]

1-60

First, 3.60 g (10.0 mmol) of 1,6-dibromo-pyrene and 5.92 g (30 mmol) of 2,6-dimethyl-N-phenylaniline were dissolved in 100 ml of toluene to form a solution. Then, 5.76 g (60.0 mmol) of t-BuONa, 0.46 g (0.5 mmol) of Pd$_2$(dba)$_3$ and 0.2 g (1.0 mmol) of t-Bu$_3$P were added to the solution which, in turn, was stirred for 6 hours under heating/reflux. After completion of the reaction, 100 ml of water was added thereto, and a toluene layer was extracted therefrom. Then, 50 ml of water was added thereto and then a further toluene layer was extracted therefrom. The extracted solution was treated with MgSO$_4$ to remove residual water and then was concentrated. Then, the concentrated solution was then column-purified with n-heptane/methylene chloride, thereby to yield 3.14 g of the compound 1-60 at 53% yield.

MS (MALDI-TOF) m/z: 592 [M]+

Synthesis Example 3

Compound 1-70 Synthesis

[Reaction Formula 3]

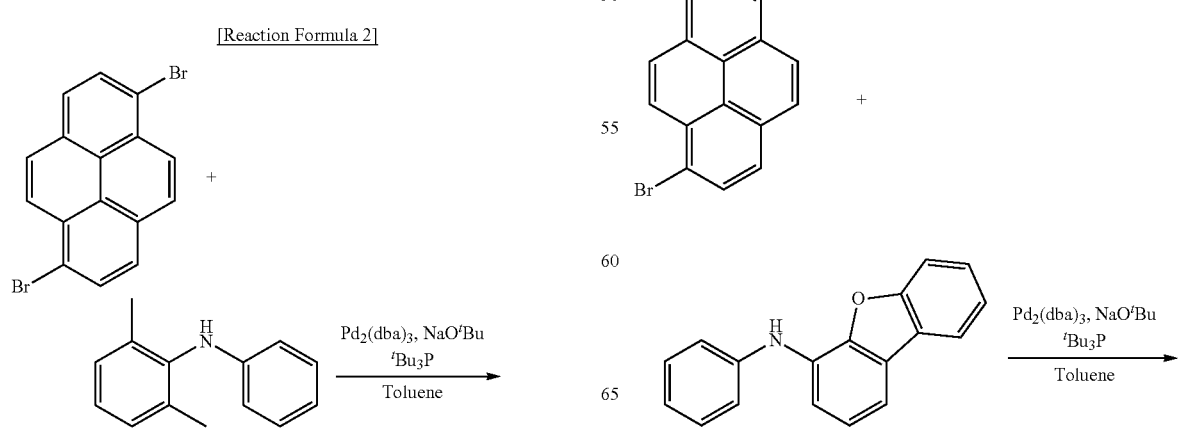

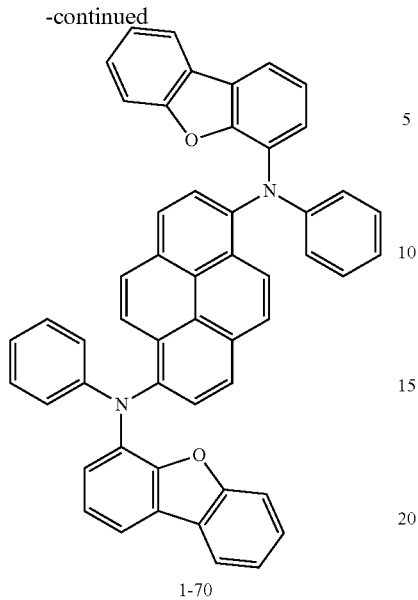

1-70

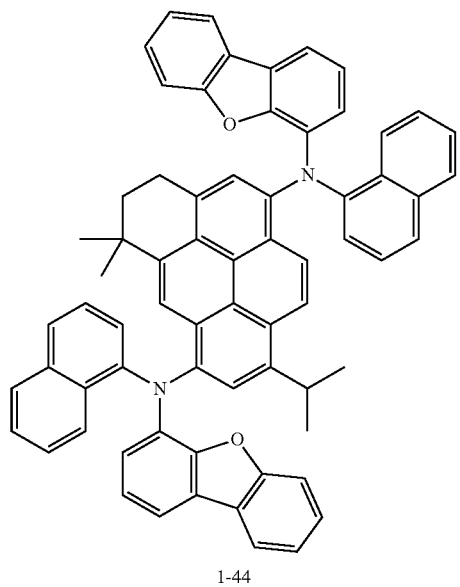

1-44

First, 3.60 g (10.0 mmol) of 1,6-dibromo-pyrene and 7.78 g (30 mmol) of N-phenyldibenzo[b, d]furan-4-amine were dissolved in 100 ml of toluene to form a solution. Then, 5.76 g (60.0 mmol) of t-BuONa, 0.46 g (0.5 mmol) of $Pd_2(dba)_3$ and 0.2 g (1.0 mmol) of $t-Bu_3P$ were added to the solution which, in turn, was stirred for 6 hours under heating/reflux. After completion of the reaction, 100 ml of water was added thereto, and a toluene layer was extracted therefrom. Then, 50 ml of water was added thereto and then a further toluene layer was extracted therefrom. The extracted solution was treated with $MgSO_4$ to remove residual water and then was concentrated. Then, the concentrated solution was then column-purified with n-heptane/methylene chloride, thereby to yield 3.80 g of the compound 1-70 at 53% yield.

MS (MALDI-TOF) m/z: 716 [M]+

Synthesis Example 4

Compound 1-44 Synthesis

[Reaction Formula 4]

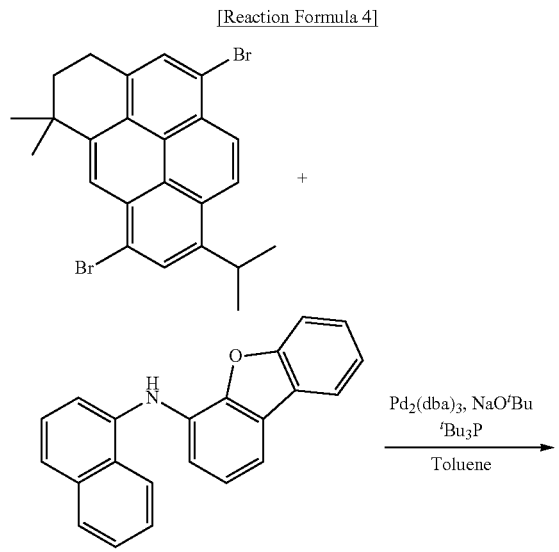

First, 4.70 g (10.0 mmol) of 1,7-dibromo-9-isopropyl-5, 5-dimethyl-4,5-dihydro-3H-benzo[cd]pyrene and 9.28 g (30 mmol) of N-(naphthalen-1-yl)dibenzo[b, d]furan-4-amine were dissolved in 100 ml of toluene to form a solution. Then, 5.76 g (60.0 mmol) of t-BuONa, 0.46 g (0.5 mmol) of $Pd_2(dba)_3$ and 0.2 g (1.0 mmol) of $t-Bu_3P$ were added to the solution which, in turn, was stirred for 6 hours under heating/reflux. After completion of the reaction, 100 ml of water was added thereto, and a toluene layer was extracted therefrom. Then, 50 ml of water was added thereto and then a further toluene layer was extracted therefrom. The extracted solution was treated with $MgSO_4$ to remove residual water and then was concentrated. Then, the concentrated solution was then column-purified with n-heptane/methylene chloride, thereby to yield 4.17 g of the compound 1-44 at 52% yield.

MS (MALDI-TOF) m/z: 926 [M]+

Synthesis Example 5

Compound 1-99 Synthesis

[Reaction Formula 5]

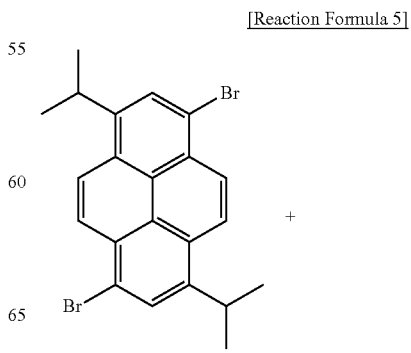

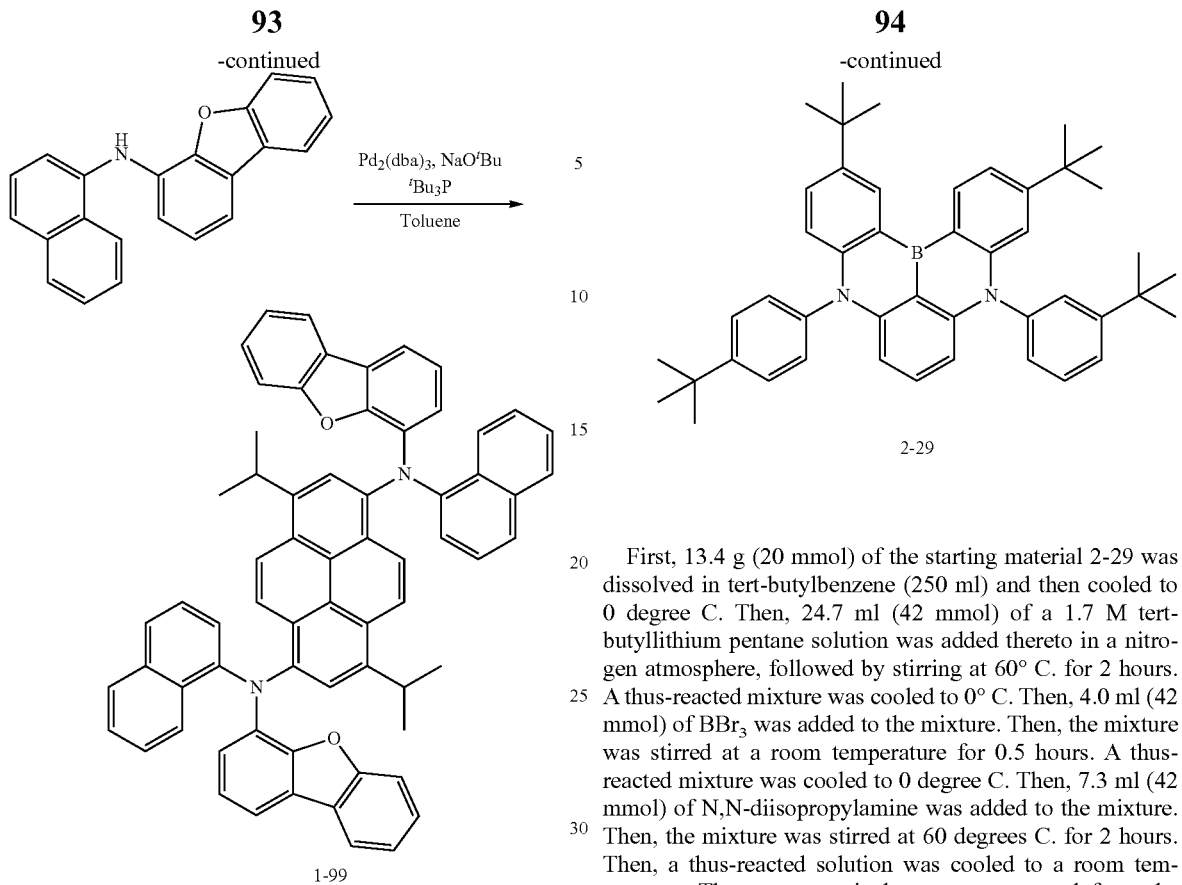

First, 3.60 g (10.0 mmol) of 1,6-dibromo-3,6-diisopropyl-pyrene and 9.28 g (30 mmol) of N-(naphthalen-1-yl)dibenzo[b,d]furan-4-amine were dissolved in 100 ml of toluene to form a solution. Then, 5.76 g (60.0 mmol) of t-BuONa, 0.46 g (0.5 mmol) of Pd$_2$(dba)$_3$ and 0.2 g (1.0 mmol) of t-Bu$_3$P were added to the solution which, in turn, was stirred for 6 hours under heating/reflux. After completion of the reaction, 100 ml of water was added thereto, and a toluene layer was extracted therefrom. Then, 50 ml of water was added thereto and then a further toluene layer was extracted therefrom. The extracted solution was treated with MgSO$_4$ to remove residual water and then was concentrated. Then, the concentrated solution was then column-purified with n-heptane/methylene chloride, thereby to yield 4.68 g of the compound 1-99 at 52% yield.

MS (MALDI-TOF) m/z: 900 [M]+

Synthesis Example 6

Compound 2-29 Synthesis

[Reaction Formula 6]

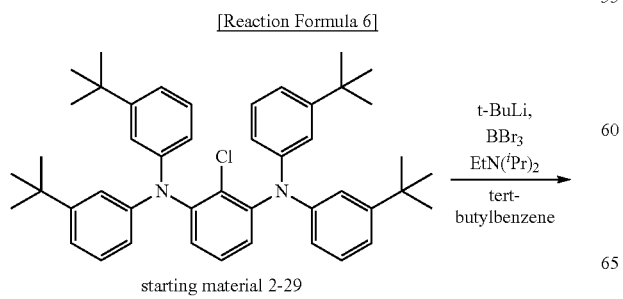

First, 13.4 g (20 mmol) of the starting material 2-29 was dissolved in tert-butylbenzene (250 ml) and then cooled to 0 degree C. Then, 24.7 ml (42 mmol) of a 1.7 M tert-butyllithium pentane solution was added thereto in a nitrogen atmosphere, followed by stirring at 60° C. for 2 hours. A thus-reacted mixture was cooled to 0° C. Then, 4.0 ml (42 mmol) of BBr$_3$ was added to the mixture. Then, the mixture was stirred at a room temperature for 0.5 hours. A thus-reacted mixture was cooled to 0 degree C. Then, 7.3 ml (42 mmol) of N,N-diisopropylamine was added to the mixture. Then, the mixture was stirred at 60 degrees C. for 2 hours. Then, a thus-reacted solution was cooled to a room temperature. Then, an organic layer was extracted from the solution using ethyl acetate and purified water. The solvent was removed from the extracted organic layer which in turn was purified using silica gel based column chromatography (methylene chloride/heptane). Then, the purified extracted organic layer was recrystallized and purified using a methylene chloride/methanol mixed solvent, thereby to obtain 4.51 g of the compound 2-29 at 35% yield.

MS (MALDI-TOF) m/z: 644 [M]+

Synthesis Example 7

Compound 2-51 Synthesis

[Reaction Formula 7]

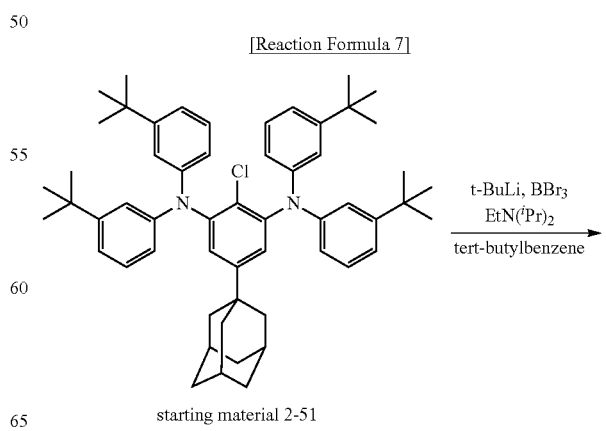

-continued

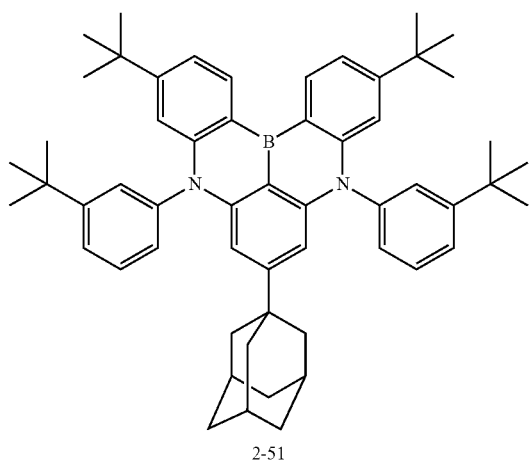

2-51

-continued

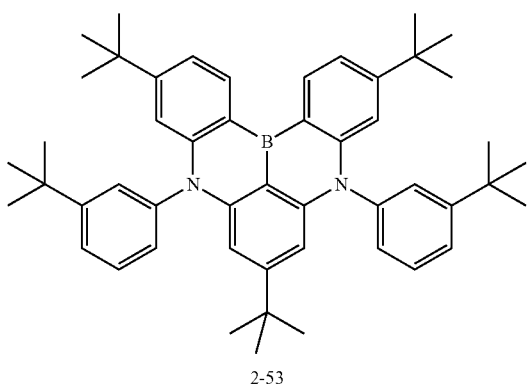

2-53

First, 16.1 g (20 mmol) of the starting material 2-51 was dissolved in t-butyllithium pentane solution 24.7 ml (42 mmol) and then stirred at 60° C. for 2 hours. A thus-reacted mixture was cooled to 0° C. Then, 4.0 ml (42 mmol) of BBr$_3$ was added to the mixture. Then, the mixture was stirred at a room temperature for 0.5 hours. A thus-reacted mixture was cooled to 0 degree C. Then, 7.3 ml (42 mmol) of N,N-diisopropylamine was added to the mixture. Then, the mixture was stirred at 60 degrees C. for 2 hours. Then, a thus-reacted solution was cooled to a room temperature. Then, an organic layer was extracted from the solution using ethyl acetate and purified water. The solvent was removed from the extracted organic layer which in turn was purified using silica gel based column chromatography (methylene chloride/heptane). Then, the purified extracted organic layer was dissolved in 24.7 ml (42 mmol) of a methylene chloride/acetone t-butyllithium pentane solution, and then stirred at 60° C. for 2 hours. Then, the purified extracted organic layer was recrystallized and purified using a methylene chloride/acetone mixed solvent, thereby to obtain 3.50 g of the compound 2-51 at 20.2% yield.

MS (MALDI-TOF) m/z: 778 [M]+

Synthesis Example 8

Compound 2-53 Synthesis

First, 14.6 g (20 mmol) of the starting material 2-53 was dissolved in tert-butylbenzene (250 ml) and then cooled to 0 degree C. Then, 24.7 ml (42 mmol) of a 1.7 M tert-butyllithium pentane solution was added thereto in a nitrogen atmosphere, followed by stirring at 60° C. for 2 hours. A thus-reacted mixture was cooled to 0° C. Then, 4.0 ml (42 mmol) of BBr$_3$ was added to the mixture. Then, the mixture was stirred at a room temperature for 0.5 hours. A thus-reacted mixture was cooled to 0 degree C. Then, 7.3 ml (42 mmol) of N,N-diisopropylamine was added to the mixture. Then, the mixture was stirred at 60 degrees C. for 2 hours. Then, a thus-reacted solution was cooled to a room temperature. Then, an organic layer was extracted from the solution using ethyl acetate and purified water. The solvent was removed from the extracted organic layer which in turn was purified using silica gel based column chromatography (methylene chloride/heptane). Then, the purified extracted organic layer was recrystallized and purified using a methylene chloride/acetone mixed solvent, thereby to obtain 3.50 g of the compound 2-53 at 25% yield.

MS (MALDI-TOF) m/z: 700 [M]+

Synthesis Example 9

Compound 2-46 Synthesis

[Reaction Formula 8]

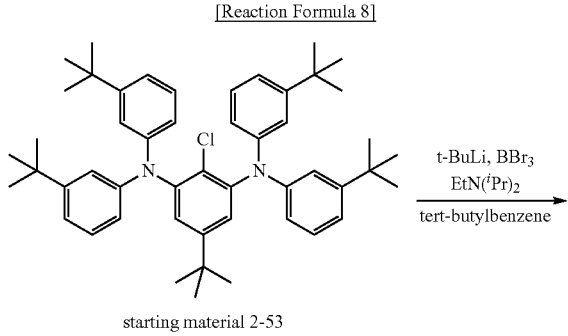

starting material 2-53 t-BuLi, BBr$_3$
EtN($^i$Pr)$_2$
tert-butylbenzene

[Reaction Formula 9]

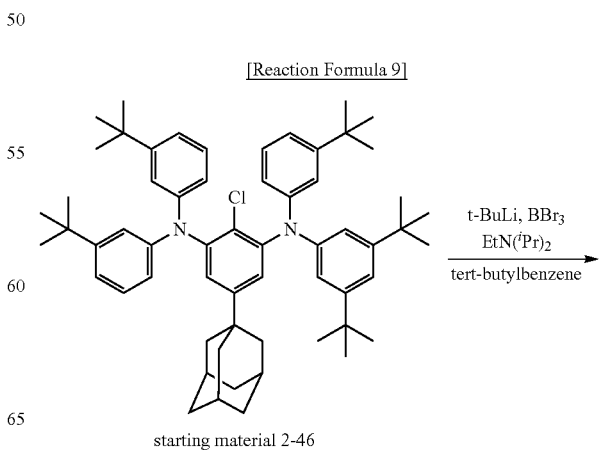

starting material 2-46 t-BuLi, BBr$_3$
EtN($^i$Pr)$_2$
tert-butylbenzene

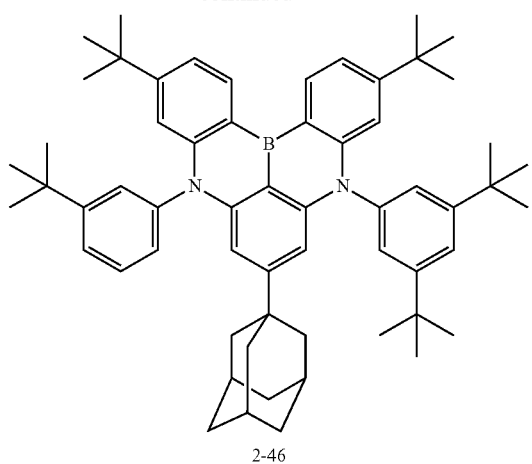

2-46

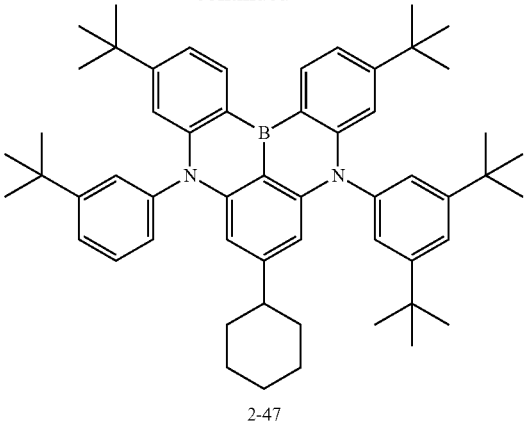

2-47

First, 17.2 g (20 mmol) of the starting material 2-46 was dissolved in tert-butylbenzene (250 ml) and then cooled to 0 degree C. Then, 24.7 ml (42 mmol) of a 1.7 M tert-butyllithium pentane solution was added thereto in a nitrogen atmosphere, followed by stirring at 60° C. for 2 hours. A thus-reacted mixture was cooled to 0° C. Then, 4.0 ml (42 mmol) of BBr₃ was added to the mixture. Then, the mixture was stirred at a room temperature for 0.5 hours. A thus-reacted mixture was cooled to 0 degree C. Then, 7.3 ml (42 mmol) of N,N-diisopropylamine was added to the mixture. Then, the mixture was stirred at 60 degrees C. for 2 hours. Then, a thus-reacted solution was cooled to a room temperature. Then, an organic layer was extracted from the solution using ethyl acetate and purified water. The solvent was removed from the extracted organic layer which in turn was purified using silica gel based column chromatography (methylene chloride/heptane). Then, the purified extracted organic layer was recrystallized and purified using a methylene chloride/acetone mixed solvent, thereby to obtain 2.00 g of the compound 2-46 at 12% yield.

MS (MALDI-TOF) m/z: 834 [M]+

Synthesis Example 10

Compound 2-47 Synthesis

[Reaction Formula 10]

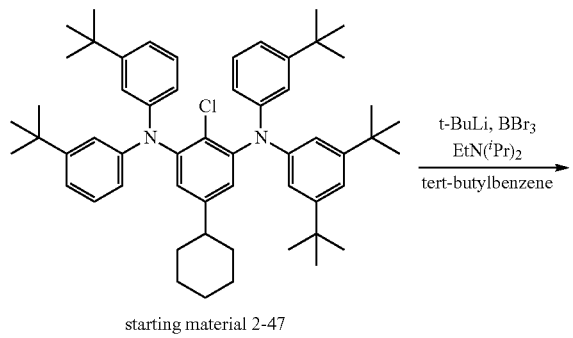

starting material 2-47

→ t-BuLi, BBr₃
EtN(ⁱPr)₂
tert-butylbenzene

First, 16.2 g (20 mmol) of the starting material 2-47 was dissolved in tert-butylbenzene (250 ml) and then cooled to 0 degree C. Then, 24.7 ml (42 mmol) of a 1.7 M tert-butyllithium pentane solution was added thereto in a nitrogen atmosphere, followed by stirring at 60° C. for 2 hours. A thus-reacted mixture was cooled to 0° C. Then, 4.0 ml (42 mmol) of BBr₃ was added to the mixture. Then, the mixture was stirred at a room temperature for 0.5 hours. A thus-reacted mixture was cooled to 0 degree C. Then, 7.3 ml (42 mmol) of N,N-diisopropylamine was added to the mixture. Then, the mixture was stirred at 60 degrees C. for 2 hours. Then, a thus-reacted solution was cooled to a room temperature. Then, an organic layer was extracted from the solution using ethyl acetate and purified water. The solvent was removed from the extracted organic layer which in turn was purified using silica gel based column chromatography (methylene chloride/heptane). Then, the purified extracted organic layer was recrystallized and purified using a methylene chloride/acetone mixed solvent, thereby to obtain 2.19 g of the compound 2-47 at 14% yield.

MS (MALDI-TOF) m/z: 782 [M]+

Example 1: Manufacturing of Organic Electroluminescent Device

An ITO (12 nm) layer as an anode of an organic electroluminescent device was deposited on a substrate. Then, patterning was performed using a photo-lithograph process to divide the substrate region into cathode and anode regions and an insulating layer region. A UV ozone treatment and a surface-treatment using O₂:N₂ plasma were executed to enhance a work-function of the anode (ITO) and to execute a descum process. Then, 1,4,5,8,9,11-hexaazatriphenylene-hexacarbonitrile (HAT-CN) as a hole-injecting layer (HIL) at 100 Å thickness was deposited on the ITO layer. Then, N4,N4,N4',N4'-tetra([1,1'-biphenyl]-4-yl)-[1,1'-biphenyl]-4,4'-diamine was vacuum deposited on the hole-injecting layer (HIL), to form a 1000 Å thick hole-transporting layer (HTL).

Then, on top of the hole-transporting layer (HTL), N-phenyl-N-(4-(spiro[benzo[de]anthracene-7,9-fluorene]-2-yl)phenyl)dibenzo[b,d]furan-4-amine as an electron-blocking layer (EBL) was deposited in a thickness of 100 angstroms. Then, on top of the electron-blocking layer (EBL), a host material of a light-emitting layer (EML) was deposited. At the same time, compound 1-5 and compound 2-29 together were doped into the host at a doping ratio of 1.5 wt % and 1.5 wt %, respectively. Thus, the light-emitting layer (EML) was formed with a thickness of 200 Å.

Then, a mixture of 2-(4-(9,10-di(naphthalene-2-yl)anthracene-2-yl)phenyl)-1-phenyl-1H-benzo[d]imidazole and LiQ in a weight ratio of 1:1 was deposited to a thickness of 260 Å as an electron-transporting layer (ETL) on the EML layer. Then, Liq was deposited on the ETL layer at 10 Å thickness and then a cathode made of Al was deposited thereon at 1000 Å thickness. Then, a seal cap was attached to the cathode with a UV curing adhesive to protect the organic electroluminescent device from atmospheric O2 or moisture. In this way, the organic electroluminescent device was fabricated.

Example 2: Manufacturing of Organic Electroluminescent Device

The organic electroluminescent device was fabricated in the same manner as in Example 1 except that dopants in the light-emitting layer EML with a thickness of 200 Å included compound 1-5 and compound 2-51 at a content of 1.5 wt % and 1.5 wt %, respectively.

Example 3: Manufacturing of Organic Electroluminescent Device

The organic electroluminescent device was fabricated in the same manner as in Example 1 except that dopants in the light-emitting layer EML with a thickness of 200 Å included the compound 1-5 and compound 2-53 at a content of 1.5 wt % and 1.5 wt %, respectively.

Example 4: Manufacturing of Organic Electroluminescent Device

The organic electroluminescent device was fabricated in the same manner as in Example 1 except that dopants in the light-emitting layer EML with a thickness of 200 Å included the compound 1-5 and compound 2-46 at a content of 1.5 wt % and 1.5 wt %, respectively.

Example 5: Manufacturing of Organic Electroluminescent Device

The organic electroluminescent device was fabricated in the same manner as in Example 1 except that dopants in the light-emitting layer EML with a thickness of 200 Å included the compound 1-5 and compound 2-47 at a content of 3 wt % and 1.5 wt %, respectively.

Example 6: Manufacturing of Organic Electroluminescent Device

The organic electroluminescent device was fabricated in the same manner as in Example 1 except that dopants in the light-emitting layer EML with a thickness of 200 Å included the compound 1-60 and compound 2-29 at a content of 1.5 wt % and 1.5 wt %, respectively.

Example 7: Manufacturing of Organic Electroluminescent Device

The organic electroluminescent device was fabricated in the same manner as in Example 1 except that dopants in the light-emitting layer EML with a thickness of 200 Å included the compound 1-60 and compound 2-51 at a content of 1.5 wt % and 1.5 wt %, respectively.

Example 8: Manufacturing of Organic Electroluminescent Device

The organic electroluminescent device was fabricated in the same manner as in Example 1 except that dopants in the light-emitting layer EML with a thickness of 200 Å included the compound 1-60 and compound 2-53 at a content of 3 wt % and 1.5 wt %, respectively.

Example 9: Manufacturing of Organic Electroluminescent Device

The organic electroluminescent device was fabricated in the same manner as in Example 1 except that dopants in the light-emitting layer EML with a thickness of 200 Å included the compound 1-60 and compound 2-46 at a content of 3 wt % and 1.5 wt %, respectively.

Example 10: Manufacturing of Organic Electroluminescent Device

The organic electroluminescent device was fabricated in the same manner as in Example 1 except that dopants in the light-emitting layer EML with a thickness of 200 Å included the compound 1-60 and compound 2-47 at a content of 3 wt % and 1.5 wt %, respectively.

Example 11: Manufacturing of Organic Electroluminescent Device

The organic electroluminescent device was fabricated in the same manner as in Example 1 except that dopants in the light-emitting layer EML with a thickness of 200 Å included the compound 1-70 and compound 2-29 at a content of 1.5 wt % and 1.5 wt %, respectively.

Example 12: Manufacturing of Organic Electroluminescent Device

The organic electroluminescent device was fabricated in the same manner as in Example 1 except that dopants in the light-emitting layer EML with a thickness of 200 Å included the compound 1-70 and compound 2-51 at a content of 1.5 wt % and 1.5 wt %, respectively.

Example 13: Manufacturing of Organic Electroluminescent Device

The organic electroluminescent device was fabricated in the same manner as in Example 1 except that dopants in the light-emitting layer EML with a thickness of 200 Å included the compound 1-70 and compound 2-53 at a content of 3 wt % and 1.5 wt %, respectively.

Comparative Example 1: Manufacturing of Organic Electroluminescent Device

The organic electroluminescent device was fabricated in the same manner as in Example 1 except that dopants in the light-emitting layer EML with a thickness of 200 Å included the compound 2-29 at a content of 3 wt %.

Comparative Example 2: Manufacturing of Organic Electroluminescent Device

The organic electroluminescent device was fabricated in the same manner as in Example 1 except that dopants in the light-emitting layer EML with a thickness of 200 Å included the compound 2-53 at a content of 1.5 wt %.

Table 1 shows device characteristic when the devices manufactured in Examples 1 to 13 and Comparative Examples 1 to 2 are driven at 10 mA/cm$^2$ and T95% lifespan versus an initial lifespan of the devices as measured at 20 mA/cm$^2$ constant current.

TABLE 1

| Examples | Drive voltage Volt | Current efficiency Cd/A | EQE (%) | Color coordinate CIEx | Color coordinate CIEy | Lifespan T95% (hrs) |
| --- | --- | --- | --- | --- | --- | --- |
| Comparative Example 1 | 3.9 | 4.2 | 6.9 | 0.139 | 0.06 | 80 |
| Comparative Example 2 | 3.89 | 4.0 | 6.8 | 0.140 | 0.058 | 85 |
| Example 1 | 4.02 | 4.2 | 6.2 | 0.139 | 0.070 | 120 |
| Example 2 | 4.01 | 4.8 | 6.3 | 0.139 | 0.080 | 140 |
| Example 3 | 3.98 | 4.8 | 6.2 | 0.140 | 0.079 | 125 |
| Example 4 | 3.9 | 4.3 | 6.0 | 0.140 | 0.060 | 115 |
| Example 5 | 3.9 | 4.3 | 6.0 | 0.140 | 0.060 | 130 |
| Example 6 | 4.0 | 4.2 | 6.2 | 0.139 | 0.070 | 110 |
| Example 7 | 4.15 | 4.8 | 6.3 | 0.139 | 0.080 | 130 |
| Example 8 | 4.1 | 4.3 | 6.0 | 0.140 | 0.060 | 110 |
| Example 9 | 4.15 | 4.3 | 6.0 | 0.140 | 0.060 | 125 |
| Example 10 | 4.2 | 4.3 | 6.0 | 0.140 | 0.060 | 120 |
| Example 11 | 4.0 | 4.2 | 6.2 | 0.139 | 0.070 | 110 |
| Example 12 | 3.8 | 4.9 | 6.4 | 0.139 | 0.080 | 120 |
| Example 13 | 3.85 | 4.5 | 6.2 | 0.140 | 0.060 | 110 |

Example 14: Manufacturing of Organic Electroluminescent Device

A light reflective layer made of Ag and an ITO (12 nm) layer as an anode of an organic electroluminescent device were deposited on a substrate. Then, patterning was performed using a photo-lithograph process to divide the substrate region into cathode and anode regions and an insulating layer region. A UV ozone treatment and a surface-treatment using $O_2$:$N_2$ plasma were executed to enhance a work-function of the anode (ITO) and to execute a descum process. Then, 1,4,5,8,9,11-hexaazatriphenylene-hexacarbonitrile (HAT-CN) as a hole-injecting layer (HIL) at 100 Å thickness was deposited on the ITO layer. Then, N4,N4, N4', N4'-tetra([1,1'-biphenyl]-4-yl)-[1,1'-biphenyl]-4,4'-diamine was vacuum deposited on the hole-injecting layer (HIL), to form a 1000 Å thick hole-transporting layer (HTL).

Then, on top of the hole-transporting layer (HTL), N-phenyl-N-(4-(spiro[benzo[de]anthracene-7,9-fluorene]-2-yl)phenyl)dibenzo[b,d]furan-4-amine as an electron-blocking layer (EBL) was deposited in a thickness of 100 angstroms. Then, on top of the electron-blocking layer (EBL), a host material of a light-emitting layer (EML) was deposited. At the same time, the compound 1-70 and compound 2-29 together were doped into the host at a doping ratio of 1.5 wt % and 1.5 wt %, respectively. Thus, the light-emitting layer (EML) was formed with a thickness of 200 Å.

Then, a mixture of 2-(4-(9,10-di(naphthalene-2-yl)anthracene-2-yl)phenyl)-1-phenyl-1H-benzo[d]imidazole and LiQ in a weight ratio of 1:1 was deposited to a thickness of 360 Å as an electron-transporting layer (ETL) on the EML layer. Then, a mixture of magnesium (Mg) and silver (Ag) at a ratio of 9:1 was deposited as a cathode at a thickness of 160 Å on the ETL layer. Next, N4,N4'-diphenyl-N4,N4'-bis(4-(9-phenyl-9H-carbazol-3-yl)phenyl-[1,1'-biphenyl]-4,4'-diamine was deposited as a capping layer (CPL) to a thickness of 63 to 65 nm on the cathode layer.

Then, a seal cap was attached to the capping layer (CPL) with a UV curing adhesive to protect the organic electroluminescent device from atmospheric $O_2$ or moisture. In this way, the organic electroluminescent device was fabricated.

Example 15: Manufacturing of Organic Electroluminescent Device

The organic electroluminescent device was fabricated in the same manner as in Example 14 except that dopants in the light-emitting layer EML with a thickness of 200 Å included the compound 1-70 and compound 2-47 at a content of 3 wt % and 1.5 wt %, respectively.

Example 16: Manufacturing of Organic Electroluminescent Device

The organic electroluminescent device was fabricated in the same manner as in Example 14 except that dopants in the light-emitting layer EML with a thickness of 200 Å included the compound 1-44 and compound 2-29 at a content of 1.5 wt % and 1.5 wt %, respectively.

Example 17: Manufacturing of Organic Electroluminescent Device

The organic electroluminescent device was fabricated in the same manner as in Example 14 except that dopants in the light-emitting layer EML with a thickness of 200 Å included the compound 1-44 and compound 2-51 at a content of 1.5 wt % and 1.5 wt %, respectively.

Example 18: Manufacturing of Organic Electroluminescent Device

The organic electroluminescent device was fabricated in the same manner as in Example 14 except that dopants in the light-emitting layer EML with a thickness of 200 Å included the compound 1-44 and compound 2-53 at a content of 3 wt % and 1.5 wt %, respectively.

Example 19: Manufacturing of Organic Electroluminescent Device

The organic electroluminescent device was fabricated in the same manner as in Example 14 except that dopants in the light-emitting layer EML with a thickness of 200 Å included the compound 1-44 and compound 2-46 at a content of 3 wt % and 1.5 wt %, respectively.

Example 20: Manufacturing of Organic Electroluminescent Device

The organic electroluminescent device was fabricated in the same manner as in Example 14 except that dopants in the light-emitting layer EML with a thickness of 200 Å included the compound 1-44 and compound 2-47 at a content of 3 wt % and 1.5 wt %, respectively.

Example 21: Manufacturing of Organic Electroluminescent Device

The organic electroluminescent device was fabricated in the same manner as in Example 14 except that dopants in the light-emitting layer EML with a thickness of 200 Å included the compound 1-99 and compound 2-29 at a content of 1.5 wt % and 1.5 wt %, respectively.

Example 22: Manufacturing of Organic Electroluminescent Device

The organic electroluminescent device was fabricated in the same manner as in Example 14 except that dopants in the light-emitting layer EML with a thickness of 200 Å included the compound 1-99 and compound 2-51 at a content of 1.5 wt % and 1.5 wt %, respectively.

Example 23: Manufacturing of Organic Electroluminescent Device

The organic electroluminescent device was fabricated in the same manner as in Example 14 except that dopants in the light-emitting layer EML with a thickness of 200 Å included the compound 1-99 and compound 2-53 at a content of 3 wt % and 1.5 wt %, respectively.

Example 24: Manufacturing of Organic Electroluminescent Device

The organic electroluminescent device was fabricated in the same manner as in Example 14 except that dopants in the light-emitting layer EML with a thickness of 200 Å included the compound 1-99 and compound 2-46 at a content of 3 wt % and 1.5 wt %, respectively.

Example 25: Manufacturing of Organic Electroluminescent Device

The organic electroluminescent device was fabricated in the same manner as in Example 14 except that dopants in the light-emitting layer EML with a thickness of 200 Å included the compound 1-99 and compound 2-47 at a content of 3 wt % and 1.5 wt %, respectively.

Comparative Example 3: Manufacturing of Organic Electroluminescent Device

The organic electroluminescent device was fabricated in the same manner as in Example 14 except that dopants in the light-emitting layer EML with a thickness of 200 Å included the compound 2-29 at a content of 3 wt %.

Comparative Example 4: Manufacturing of Organic Electroluminescent Device

The organic electroluminescent device was fabricated in the same manner as in Example 14 except that dopants in the light-emitting layer EML with a thickness of 200 Å included the compound 2-51 at a content of 2 wt %.

Table 2 shows device characteristic when the devices manufactured in the Examples 14 to 25 and Comparative Examples 3 to 4 are driven at 10 mA/cm$^2$ and T95% lifespan versus an initial lifespan of the devices as measured at 20 mA/cm$^2$ constant current.

TABLE 2

| Examples | Drive voltage Volt | Current efficiency Cd/A | EQE (%) | Color coordinate CIEx | CIEy | Lifespan T95% (hrs) |
|---|---|---|---|---|---|---|
| Comparative Example 3 | 3.72 | 5.8 | 12.8 | 0.137 | 0.049 | 90 |
| Comparative Example 4 | 3.73 | 5.1 | 12.5 | 0.143 | 0.045 | 100 |
| Example 14 | 3.71 | 5.2 | 12.3 | 0.144 | 0.046 | 130 |
| Example 15 | 3.76 | 5.0 | 11.7 | 0.143 | 0.045 | 155 |
| Example 16 | 3.74 | 5.4 | 11.9 | 0.143 | 0.047 | 160 |
| Example 17 | 3.74 | 5.1 | 12.5 | 0.143 | 0.045 | 165 |
| Example 18 | 3.76 | 5.2 | 12.0 | 0.140 | 0.044 | 145 |
| Example 19 | 3.76 | 5.0 | 11.7 | 0.143 | 0.045 | 155 |
| Example 20 | 3.8 | 5.3 | 12.1 | 0.143 | 0.045 | 170 |
| Example 21 | 3.72 | 5.7 | 12.6 | 0.137 | 0.049 | 145 |
| Example 22 | 3.8 | 5.4 | 12.3 | 0.143 | 0.045 | 160 |
| Example 23 | 3.76 | 5.2 | 12.0 | 0.140 | 0.044 | 140 |
| Example 24 | 3.8 | 5.1 | 12.5 | 0.143 | 0.045 | 155 |
| Example 25 | 3.78 | 5.3 | 12.1 | 0.143 | 0.045 | 150 |

From the above tables, the organic electroluminescent devices using two or more compounds according to Chemical Formula 1 and Chemical Formula 2 exhibit color characteristics equal or superior to those of Comparative Examples. Further, from the above tables, the organic electroluminescent devices using two or more compounds according to Chemical Formula 1 and Chemical Formula 2 exhibit a lifespan superior to those of Comparative Examples 1 to 4.

While the foregoing description has been described with reference to the embodiments of the present disclosure, various changes and modifications may be made thereto at a level of ordinary skill in the art. Accordingly, it is to be understood that such changes and modifications are included within the scope of the present disclosure, without departing from the scope of the present disclosure.

What is claimed is:

1. An organic electroluminescent device comprising an anode, a cathode, and at least one organic layer between the anode and the cathode,
   wherein the organic layer comprises a light emission layer,
   wherein the light emission layer comprises a first dopant and a second dopant,
   wherein the first dopant comprises the compound selected from the group consisting of:

1-5

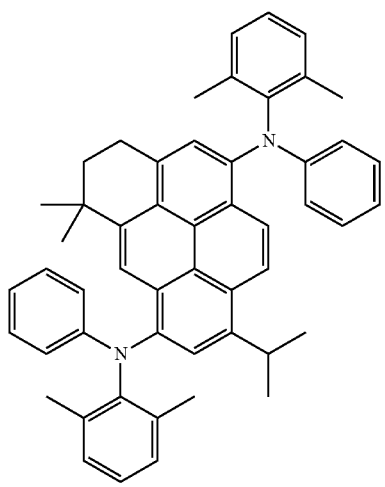

1-44
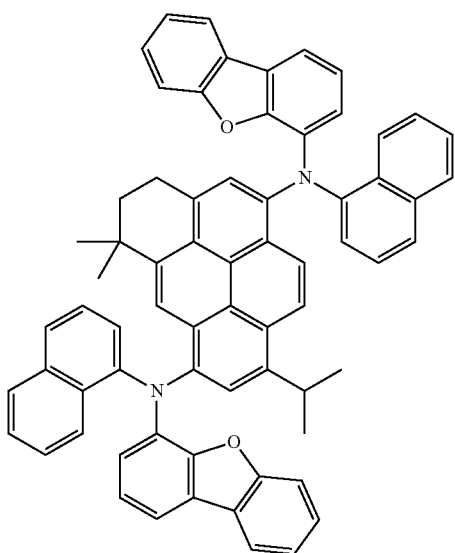
1-60
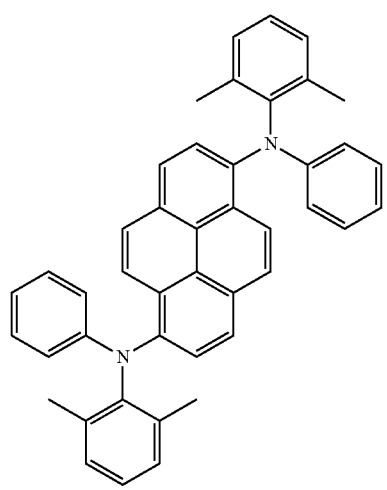
1-70
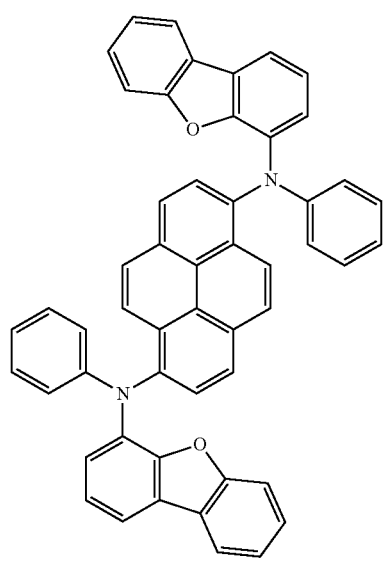
1-99
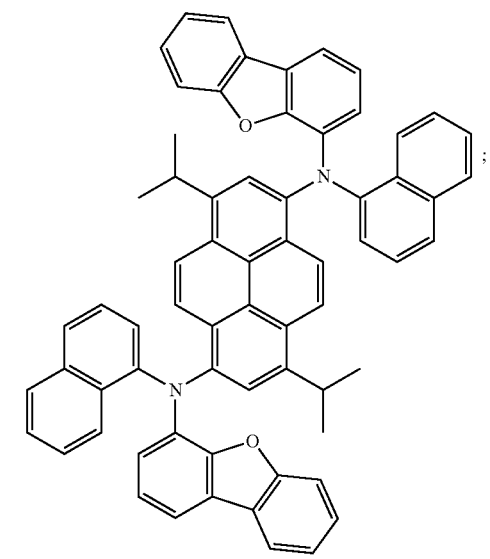
and
wherein the second dopant comprises the compound selected from the group consisting of:
2-29
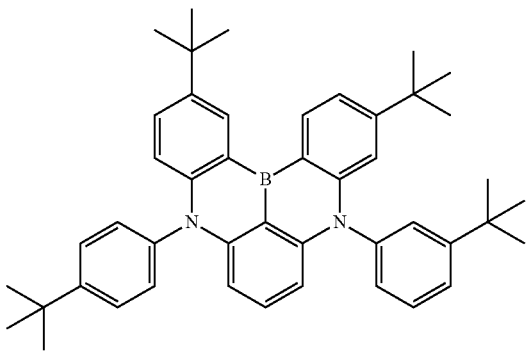
2-46
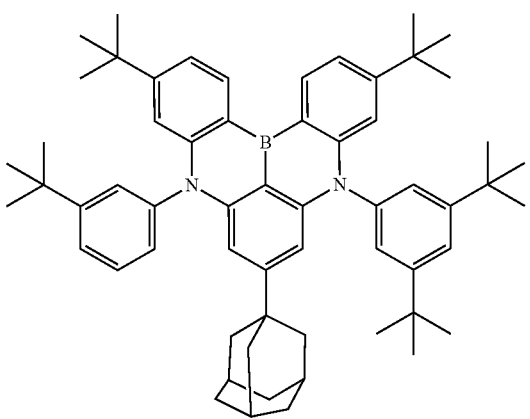

-continued 2-47
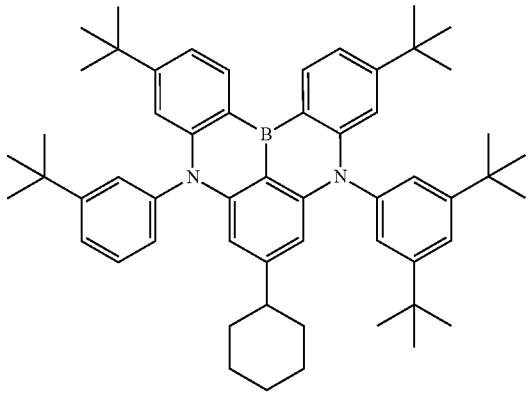

2-51
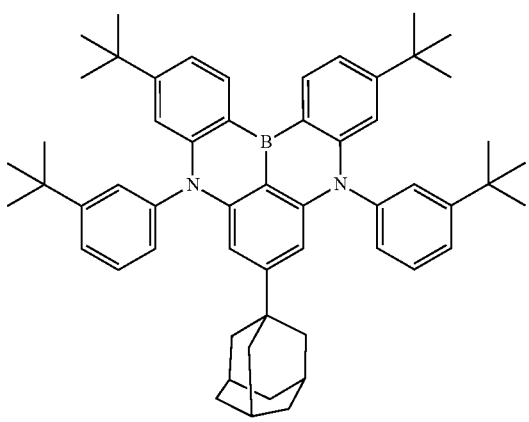

2-53
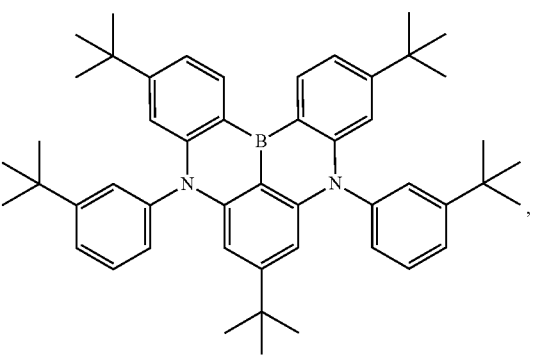

wherein the weight ratio of the first dopant to the second dopant is from 1:1 to 7:3.

2. The organic electroluminescent device of claim 1, wherein the light emission layer further comprises a host, and the host comprises a blue light-emitting host material, wherein the blue light-emitting host material includes at least one selected from the group consisting of 4,4'-bis(2,2'-diphenylvinyl)-1,1'-biphenyl (DPVBi), 9,10-di-(2-naphtyl)anthracene (ADN), 2,5,8,11-(tetra-t-butylperylene (TBADN), 2-tert-butyl-9,10-di(2-naphthyl)anthracene, 2-methyl-9,10-di(2-naphtyl)anthracene (MADN), and 2,2',2"-(1,3,5-benzinetriyl)-tris(1-phenyl-1-H-benzimidazole (TBPi).

3. The organic electroluminescent device of claim 1, wherein a content of the first dopant is in a range of 0.01 to 20 wt % based on a total weight of the light emission layer.

4. The organic electroluminescent device of claim 1, wherein a content of the second dopant is in a range of 0.01 to 20 wt % based on a total weight of the light emission layer.

5. An organic electroluminescent device comprising:
a first light emission sub-stack for rendering a first color; and
a second light emission sub-stack stacked on the first light emission sub-stack for rendering a second color,
wherein the first light emission sub-stack comprises a first light-emitting layer, and the second light emission sub-stack comprises a second light-emitting layer,
wherein at least one of the first light-emitting layer or the second light-emitting layer comprises a first dopant and a second dopant,
wherein the first dopant comprises a compound selected from the group consisting of:

1-5
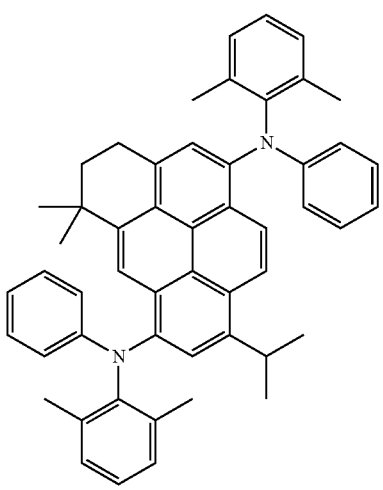

1-44
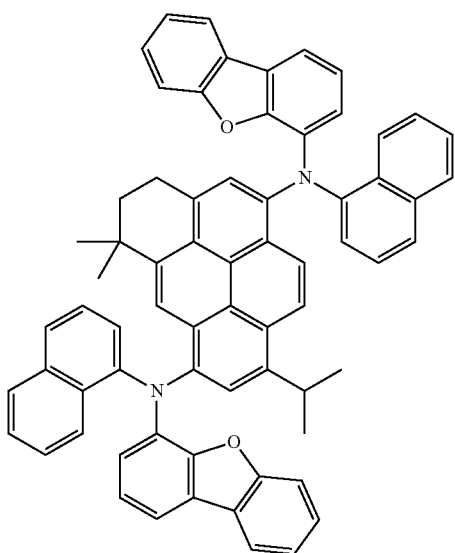
1-60
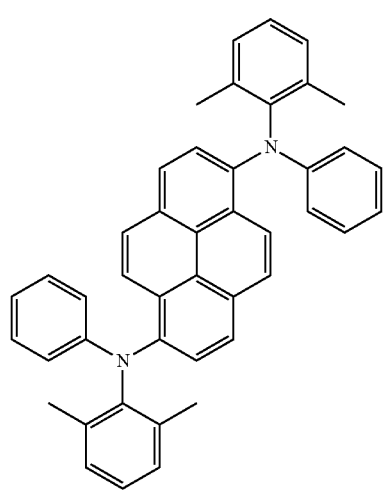
1-70
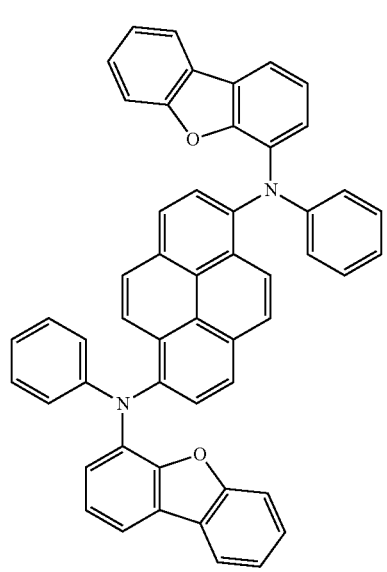
1-99
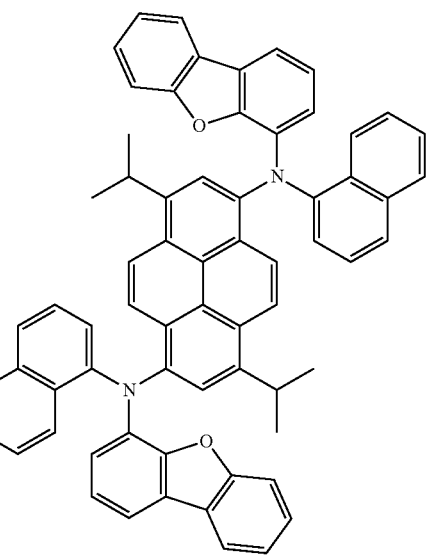
and
wherein the second dopant comprises the compound selected from the group consisting of:
2-29
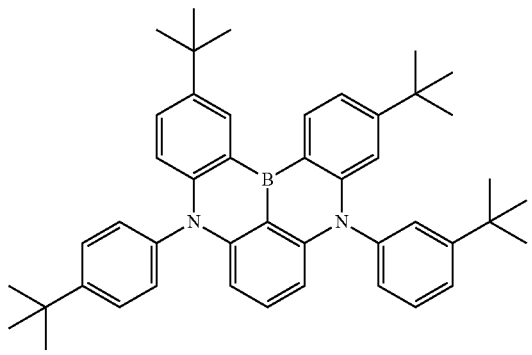

2-46

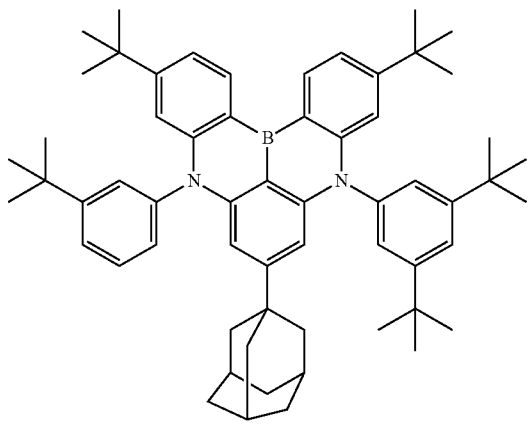

2-47

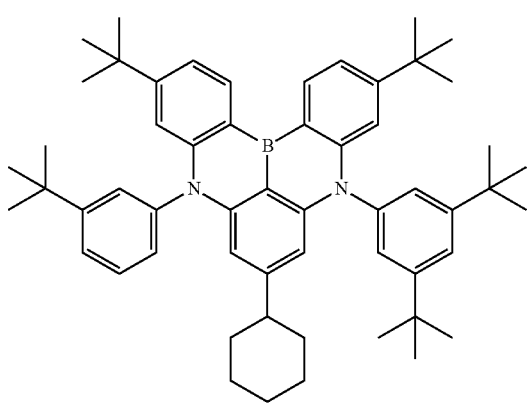

2-51

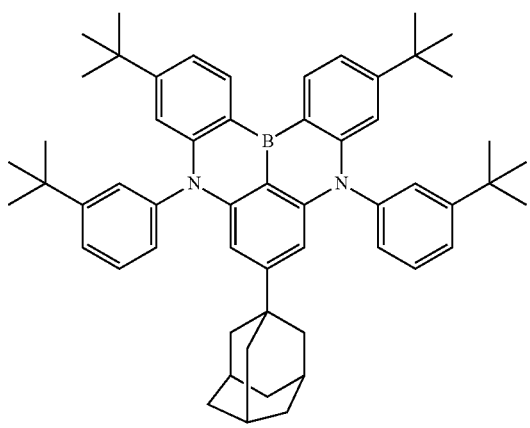

2-53

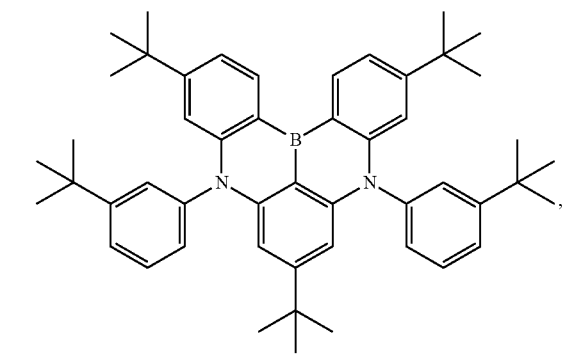

wherein the weight ratio of the first dopant to the second dopant is from 1:1 to 7:3.

6. The organic electroluminescent device of claim 5,
wherein at least one of the first light-emitting layer or the second light-emitting layer further comprises a host, and the host comprises a blue light-emitting host material, and wherein the blue light-emitting host material includes at least one selected from the group consisting of 4,4'-bis (2,2'-diphenylyinyl)-1,1'-biphenyl (DPVBi), 9,10-di-(2-naphtyl)anthracene (ADN), 2,5,8,11-(tetra-t-butylp-erylene (TBADN), 2-tert-butyl-9,10-di(2-naphthyl) anthracene, 2-methyl-9,10-di(2-naphtyl)anthracene (MADN), and 2,2',2"-(1,3,5-benzinetriyl)-tris(1-phenyl-1-H-benzimidazole (TBPi).

7. The organic electroluminescent device of claim 5, wherein the first light emission sub-stack sequentially comprises a first hole transport layer, a first light-emitting layer, and a first electron transport layer, and the second light emission sub-stack sequentially comprises a second hole transport layer, a second light-emitting layer and a second electron transport layer.

* * * * *